(12) United States Patent
Fors et al.

(10) Patent No.: US 11,692,065 B2
(45) Date of Patent: Jul. 4, 2023

(54) PHENAZINE COPOLYMERS AND USES THEREOF

(71) Applicant: CORNELL UNIVERSITY, Ithaca, NY (US)

(72) Inventors: Brett P. Fors, Ithaca, NY (US); Héctor D. Abruña, Ithaca, NY (US); Cara Gannett, Cicero, NY (US); Brian Peterson, Ithaca, NY (US); Luxi Shen, Stoneham, MA (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 17/599,328

(22) PCT Filed: Mar. 30, 2020

(86) PCT No.: PCT/US2020/025829
§ 371 (c)(1),
(2) Date: Sep. 28, 2021

(87) PCT Pub. No.: WO2020/205796
PCT Pub. Date: Oct. 8, 2020

(65) Prior Publication Data
US 2022/0153931 A1 May 19, 2022

Related U.S. Application Data

(60) Provisional application No. 62/826,125, filed on Mar. 29, 2019.

(51) Int. Cl.
*C08G 73/06* (2006.01)
*C08K 5/18* (2006.01)
(Continued)

(52) U.S. Cl.
CPC ............ *C08G 73/0694* (2013.01); *C08K 5/18* (2013.01); *H10K 85/111* (2023.02); *H10K 50/82* (2023.02)

(58) Field of Classification Search
CPC .................. C08G 73/0694; C08K 5/18; H01L 51/0035; H01L 51/5221
See application file for complete search history.

(56) References Cited

U.S. PATENT DOCUMENTS 6,096,234 A 8/2000 Nakanishi et al.
6,569,361 B1 * 5/2003 Berneth .................. C09K 9/02
359/275

(Continued)

FOREIGN PATENT DOCUMENTS

CN 110628022 A 12/2019
CN 110767906 A 2/2020

(Continued)

OTHER PUBLICATIONS

Chhattre, S., et al., "Phenazine-containing poly(phenylenevinylene): a new polymer with impressive field emission properties," Journal of Polymer Research, (2018) 25: 61.

(Continued)

*Primary Examiner* — Shane Fang
(74) *Attorney, Agent, or Firm* — Paul J. Roman, Jr.; Johnson, Marcou, Isaacs & Nix, LLC

(57) ABSTRACT

Provided are phenazine copolymers and methods of making and using phenazine copolymers. The phenazine copolymers may be made from one or more phenazine precursors and one or more co-monomer precursors, one or more phenazine precursors and one or more cross-linking precursors, or one or more phenazine precursors and both one or more cross-linking precursors and one or more co-monomer precursors. The phenazine copolymers may be used in/on (Continued)

cathodes. The cathodes may be used in a variety of devices, such as, for example, batteries or supercapacitors.

13 Claims, 41 Drawing Sheets

(51) Int. Cl.
*H10K 85/10* (2023.01)
*H10K 50/82* (2023.01)

(56) References Cited

U.S. PATENT DOCUMENTS

| | | | |
|---|---|---|---|
| 10,208,244 | B2 | 2/2019 | Yamada et al. |
| 2010/0148635 | A1 | 6/2010 | Kwon et al. |
| 2014/0212768 | A1 | 7/2014 | Zhong et al. |
| 2015/0132667 | A1* | 5/2015 | Sato ............... H01M 4/602 |
| | | | 429/340 |
| 2016/0351815 | A1 | 12/2016 | Papagni et al. |
| 2017/0250442 | A1 | 8/2017 | Maranas et al. |
| 2018/0248190 | A1 | 8/2018 | Pan et al. |
| 2018/0260673 | A1 | 9/2018 | Johnson et al. |
| 2018/0321565 | A1* | 11/2018 | Erno ............... G02F 1/1516 |
| 2018/0366757 | A1 | 12/2018 | Wei et al. |
| 2020/0388847 | A1* | 12/2020 | Zhao ............... C07D 403/14 |
| 2022/0105498 | A1* | 4/2022 | Wang ............... B01J 23/8913 |

FOREIGN PATENT DOCUMENTS

| | | |
|---|---|---|
| DE | 4325591 A1 | 2/1995 |
| JP | 5488799 B2 | 5/2014 |
| WO | 2014189122 A1 | 11/2014 |
| WO | 2019218347 A1 | 11/2019 |

OTHER PUBLICATIONS

Lee, M., et al., "Multi-elecron redox phenazine for ready-to-charge organic batteries," Green Chemistry 19 2017, abstract only.
Gannett, C., et al., "Cross-linking Effects on Performance Metrics of Phenazine-Based Polymer Cathodes," ChemSusChem 2020, 13.
Obrezkov, F., et al., "High-Energy and High-Power-Density Potassium Ion Batteries Using Dihydrophenazine-Based Polymer as Active Cathode Material," J. Phys. Chem. Lett. 2019, 10.
Tian, B., et al., "Amino group enhanced phenazine derivatives as electrode materials for lithium storage," Chem Commun., 2017, 53, 2914.
Van, F., et al., "Polyethyleneoxide-dihydrophenazine block copolymer as a cathode material for lithium-polymer batteries," Electrochimica, vol. 43, Nos. 14-15, 1998.
Vitaku. E., et al., "Phenazine-Based Covalent Organic Framework Cathode Materials with High Energy and Power Densities," J. Am. Chem. Soc., 2020, 142, 16-20.
Izumi, A et al., Synthesis of A New Class of n-Dopable and Photoluminescent Conjugated Polymers Having Phenazine Units in the Main Chain, Macromolecules 33, pp. 8918-8920, 2000; p. 8919, scheme 2, see structure 3b.
Inzelt, G, Conducting Polymers—A New Era in Electrochemistry, Springer-Verlag, pp. 1-21 (pp. 1-264), 2008; p. 21, first paragraph, see structure.
Niitani, T et al., Star-Shaped Polymer Electrolyte with Microphase Separation Structure for All-Solid-Slate Lithium Batteries, Journal of the Electrochemical Society, 156(7), pp. A577-A583, 2009; abstract; page A577, col. 2, second paragraph; p. A580, second col. first paragraph.
Levin, OV et al., Composite LiFeP04/poly-3,4-ethylenedioxythiophene Cathode for Lithium-Ion Batteries with Low Content of Non-Electroactive Components, International Journal of Electrochemical Science 10, pp. 8175-8189, 2015; abstract; p. 8177, first paragraph.
Hennaoui, F et al., Green Synthesis of Copolymer Electrolytes for Lithium Batteries Catalyzed by an Ecocatalyst Maghnite-H+, Journal of Chemical and Pharmaceutical Research, 9(6), pp. 228-234, 2017; abstract; p. 228, first paragraph; p. 229, first paragraph.

* cited by examiner

PHENAZINE COPOLYMERS AND USES THEREOF

CROSS REFERENCE TO RELATED APPLICATIONS

This application is a U.S. national phase entry of International Application No. PCT/US2020/025829 filed Mar. 30, 2020, which claims priority to U.S. Provisional Application No. 62/826,125, filed on Mar. 29, 2019, the disclosures of each of which is are incorporated herein by reference.

STATEMENT REGARDING FEDERALLY SPONSORED RESEARCH

This invention was made with government support under contract no. 1719875 awarded by the National Science Foundation. The government has certain rights in the invention.

BACKGROUND OF THE DISCLOSURE

Organic materials offer advantages over traditional metal oxide cathodes in electrical energy storage applications. Due to the high natural abundance of the constituting elements (e.g., C, N, S, O) and the ability to easily tune the structure, organic materials are expected to be much more economically and environmentally practical than their metal oxide counterparts. Additionally, organic cathodes can tolerate much faster charge/discharge rates and achieve higher power densities. Traditionally employed inorganic oxide cathodes undergo kinetically slow (de)/intercalation events which limit their rate performance. Conversely, charge balancing counter ions encounter much less resistance through amorphous organic cathodes due to the relatively weak intermolecular forces in these materials. This allows organic materials to accommodate fast ion transport, allowing faster charging and discharging rates. Furthermore, because organic electrode materials store charge through faradic processes, the operating voltage can be tuned to higher values by adjusting chemical structure and composition. Lastly, and perhaps most advantageous, is the compatibility of p-type organic cathode materials with a range of anode materials. Since p-type materials balance charge with anions from the electrolyte, they are not dependent on the cations present in solution, enabling the use of a wider variety of anode materials (sodium, potassium, etc.).

SUMMARY OF THE DISCLOSURE

The present disclosure provides phenazine copolymers. The present disclosure also provides methods of making phenazine copolymers and methods of using phenazine copolymers.

In an aspect, the present disclosure provides copolymers comprising a plurality of phenazine units. The copolymers are referred to as phenazine copolymers.

The phenazine copolymers may comprise a plurality of phenazine units; and a plurality of co-monomer units or a plurality of cross-linking units or both a plurality of co-monomer units and a plurality of cross-linking units. The phenazine units are covalently bonded to a co-monomer unit and/or a cross-linking unit.

In an aspect, the present disclosure provides methods of making phenazine copolymers. Non-limiting examples of methods are provided herein. A phenazine copolymer may be made by a method of the present disclosure.

In an aspect, the present disclosure provides cathodes. The cathodes can be used in devices such as, for example, batteries, superconductors, and the like. The cathodes comprise one or more phenazine copolymer of the present disclosure. Non-limiting examples of cathodes are provided herein.

In an aspect, the present disclosure provides devices. The devices comprise one or more phenazine copolymer of the present disclosure, which may be part of one or more cathode, and/or one or more phenazine copolymer formed by a method of the present disclosure, which may be part of one or more cathode.

BRIEF DESCRIPTION OF THE FIGURES

For a fuller understanding of the nature and objects of the disclosure, reference may be made to the following detailed description taken in conjunction with the accompanying figures.

DETAILED DESCRIPTION OF THE DISCLOSURE

Figure 1:
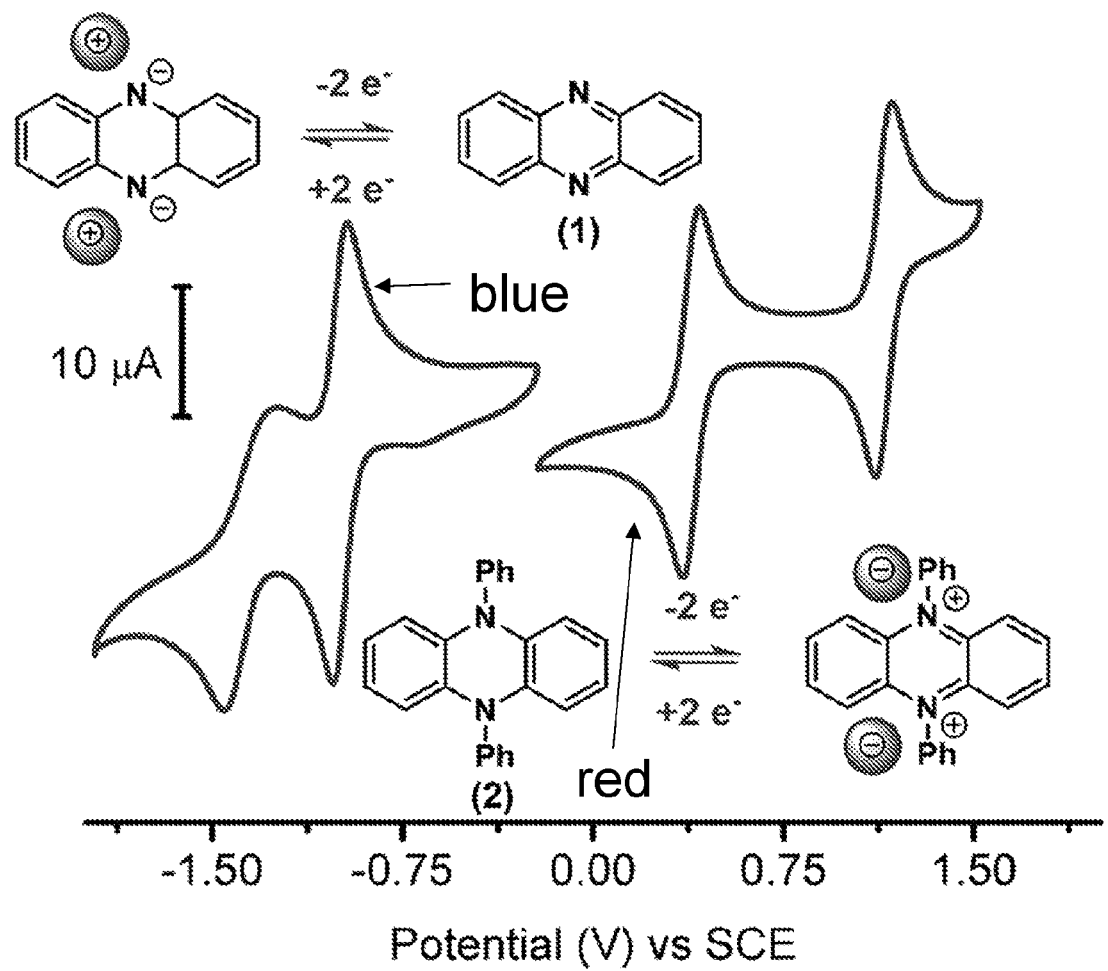
FIG. 1 shows neutral and reduced states of phenazine (1) and the neutral and oxidized states of N,N'-diphenylphenazine (2). CV's at a glassy carbon electrode of 1 mM solutions of 1 (blue) and 2 (red) in 0.1M TBAP in acetonitrile at 50 mV/s.

Although the subject matter will be described in terms of certain examples, other examples, including examples that do not provide all of the benefits and features set forth herein, are also within the scope of this disclosure. Various structural, logical, process step, and electronic changes may be made without departing from the scope of the disclosure.

The present disclosure provides phenazine copolymers. The present disclosure also provides methods of making phenazine copolymers and methods of using phenazine copolymers.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

As used herein, unless otherwise indicated, the terms "group" or "unit" refers to a chemical entity that is monovalent (i.e., has one terminus that can be covalently bonded to another chemical species), or divalent or polyvalent (i.e., has two or more termini that can be covalently bonded to other chemical species). The term "group" also includes radicals (e.g., monovalent and multivalent radicals, such as, for example, divalent radicals, trivalent radicals, and the like). Illustrative examples of groups include, but are not limited to:

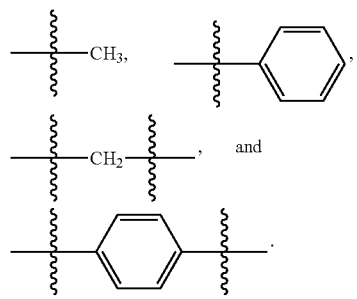

As used herein, unless otherwise indicated, the term "alkyl group" refers to branched or unbranched saturated hydrocarbon groups. Examples of alkyl groups include, but are not limited to, methyl groups, ethyl groups, propyl groups, butyl groups, isopropyl groups, tert-butyl groups, and the like. For example, an alkyl group can be a $C_1$ to $C_{12}$ alkyl group, including all integer numbers of carbons and ranges of numbers of carbons therebetween ($C_1$, $C_2$, $C_3$, $C_4$, $C_5$, $C_6$, $C_7$, $C_8$, $C_9$, $C_{10}$, $C_{11}$, or $C_{12}$). An alkyl group may be unsubstituted or substituted with one or more substituent(s). Examples of substituents include, but are not limited to, various substituents such as, for example, halogens (—F, —Cl, —Br, and —I), aliphatic groups (e.g., alkyl groups, alkenyl groups, and alkynyl groups), aryl groups, alkoxide groups, carboxylate groups, carboxylic acids, ether groups, and the like, and combinations thereof.

As used herein, unless otherwise indicated, the term "heteroalkyl group" refers to branched or unbranched saturated hydrocarbon groups comprising at least one heteroatom. Examples of suitable heteroatoms include, but are not limited to, nitrogen, oxygen, sulfur, phosphorus, halogens, and combinations thereof. A heteroalkyl group may be unsubstituted or substituted with one or more substituent(s). Examples of substituents include, but are not limited to, various substituents such as, for example, halogens (—F, —Cl, —Br, and —I), aliphatic groups (e.g., alkenes, alkynes), aryl groups, alkoxides, carboxylates, carboxylic acids, ether groups, and the like, and combinations thereof.

As used herein, unless otherwise indicated, the term "aryl group" refers to $C_5$ to $C_{12}$ aromatic or partially aromatic carbocyclic groups, including all integer numbers of carbons and ranges of numbers of carbons therebetween ($C_5$, $C_6$, $C_7$, $C_8$, $C_9$, $C_{10}$, $C_{11}$, or $C_{12}$). An aryl group can also be referred to as an aromatic group. The aryl groups may be or comprise polyaryl groups such as, for example, fused ring or biaryl groups. An aryl group may be unsubstituted or substituted with one or more substituent(s). Examples of substituents include, but are not limited to, substituents such as, for example, halogens (—F, —Cl, —Br, and —I), aliphatic groups (e.g., alkenes, alkynes, and the like), aryl groups, alkoxides, carboxylates, carboxylic acids, ether groups, and the like, and combinations thereof. Examples of aryl groups include, but are not limited to, phenyl groups, biaryl groups (e.g., biphenyl groups and the like), and fused ring groups (e.g., naphthyl groups and the like).

As used herein, unless otherwise indicated, the term "heteroaryl group" refers to a monovalent monocyclic or polycyclic aromatic group of 5 to 18 (5, 6, 7, 8, 9, 10, 11, 12, 13, 14, 15, 16, 17, or 18) ring atoms or a polycyclic aromatic group, containing one or more ring heteroatom(s) independently chosen from N, O, S, and combinations thereof, and the remaining ring atoms are C. Heteroaryl groups include polycyclic (e.g., bicyclic) heteroaromatic groups where the heteroatom is N, O, S, or a combination thereof. The aromatic group may be substituted independently with one or more substituents described herein. The substituents may be substituted. Examples of heteroaryl groups include, but are not limited to, benzothiophene, furyl, thienyl, pyrrolyl, pyridyl, pyrazinyl, pyrazolyl, pyridazinyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, benzoimidazolyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two fused rings, heteroaryl groups herein defined may have an unsaturated or partially saturated ring fused with a fully saturated ring.

As used herein, V refers to volt(s); s refers to second(s); and h refers to hour(s).

In an aspect, the present disclosure provides copolymers comprising a plurality of phenazine units. The copolymers are referred to as phenazine copolymers.

The phenazine copolymers may comprise a plurality of phenazine units; and a plurality of co-monomer units (e.g., aryl-halide coupling units) or a plurality of cross-linking units or both a plurality of co-monomer units and a plurality of cross-linking units. The phenazine units are covalently bonded to a co-monomer unit and/or a cross-linking unit.

The phenazine copolymers may be described as follows:

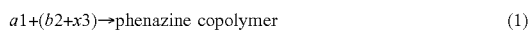

$$a1+(b2+x3) \rightarrow \text{phenazine copolymer} \quad (1)$$

$$b+3/2x=a \quad (2),$$

or

$$b+(n/2)x=a \quad (10),$$

where 1 is the phenazine units and/or 2 is the co-monomer units and/or 10 is the cross-linking units and/or a is the amount of the phenazine units and/or b is the amount of the co-monomer units and/or x is the amount of the cross-linking units and/or n is the number of reactive sites in the cross-linking unit. The ratios of phenazine units to co-monomers and/or cross-linking monomer units may be determined by equations (1) and/or (2) and/or (3). In various examples, a is greater than 0, b is greater than or equal to zero (e.g., b is greater than 0), x is greater than or equal to zero (e.g., x is greater than 0), and n is greater than or equal to 3. For example, when a is equal to 1, b is 0.7 to 1.1 (e.g., 0.9), and x is 0.05 to 0.08 (e.g., 0.067). In various other examples, when b is equal to 1, a is 0.8 to 1.2 (e.g., 1) and x is 0.05 to 0.08 (e.g., 0.067). In various examples, a is 1, b is 0 to 1 (e.g., 0.25 to 0.50) and x is 0 to 0.66 (e.g., 0.33 to 0.50).

A phenazine copolymer comprise various phenazine units. A phenazine copolymer may comprise one or more or all of the same phenazine unit(s) (e.g., phenazine unit(s) that are structurally the same). A phenazine copolymer may comprise two or more structurally distinct phenazine unit(s). A phenazine unit may have the following structure:

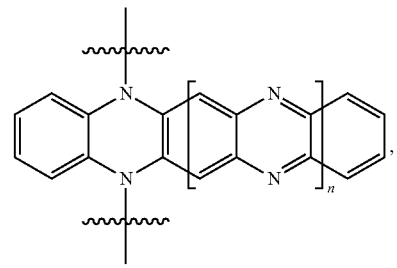

where n is 0 to 100, including every integer value and range therebetween (e.g., n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range or a range with bounds chosen therefrom);

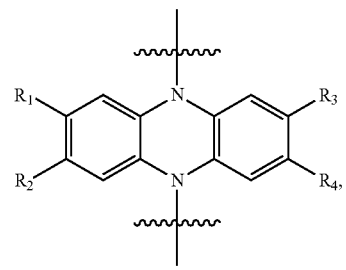

where $R_1$, $R_2$, $R_3$, and $R_4$ are independently at each occurrence chosen from —H, —F, —Cl, —I, —CH=O, and the like; or

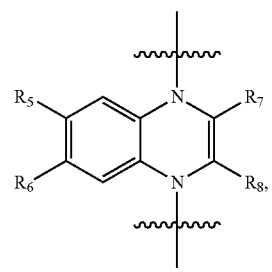

where $R_5$, $R_6$, $R_7$, and $R_8$ are independently at each occurrence chosen from —H, —F, —Cl, —I, —CH=O, and the like. A phenazine copolymer may comprise a combination of the phenazine units described herein.

Phenazine copolymers may comprise various co-monomer units. A co-monomer unit may be formed from a co-monomer comprising two polymerizable groups. A co-monomer unit may comprise one or more unreacted polymerizable groups. Co-monomer units may have the following structure:

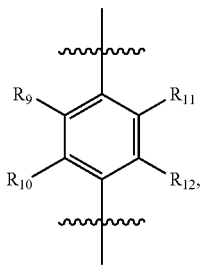

where $R_9$, $R_{10}$, $R_{11}$, and $R_{12}$ are independently at each occurrence chosen from —H, alkoxy groups (e.g., —OCH$_3$), —CN, alkyl groups (e.g., —CH$_3$, —(CH$_2$)$_n$CH$_3$ where n is 1, 2, 3, 4, 5, 6, 7, 8, 9, 10, 11, or 12)), heteroalkyl groups, such as, for example, thioether groups (e.g., —SCH$_3$), and the like; or

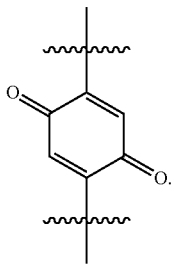

A phenazine copolymer may comprise a combination of various co-monomers.

Phenazine copolymers may comprise various cross-linking units. A cross-linking unit may be formed from a cross-linker comprising three or more reactive groups (e.g., polymerizable groups (e.g., —F, —Cl, —Br, —I, —CH═O, —OR, and the like, where —OR is —OTs (tosylate), —OMs (mesylate), or —OTf (triflate)). A cross-linking unit may comprise one or more unreacted reactive groups (e.g., polymerizable groups). The cross-linking units may comprise heteroaryl groups, aryl groups, or a combination thereof. Cross-linking units can cross-link phenazine copolymers. Cross-linking units may crosslink two or more (e.g., 2, 3, 4, etc.) phenazine units. In certain examples, in a phenazine copolymer comprising one or more cross-linking unit(s), one or some of the cross-linking unit(s) do not cross-link the phenazine copolymer, while one or some of the cross-linking unit(s) do cross-link the phenazine copolymer. Cross-linking units may have the following structure:

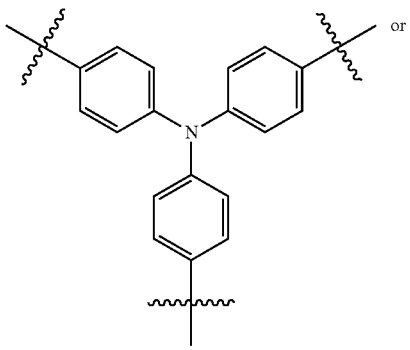

or

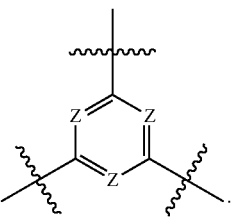

For example, when the cross-linking units in a phenazine copolymer may be formed from:

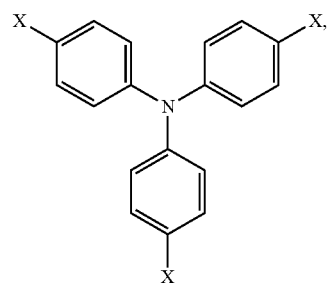

where X is independently at each occurrence chosen from a phenazine unit, a co-monomer unit, —F, —Cl, —Br, —I, —CH═O, —OR, and the like, where —OR is —OTs (tosylate), —OMs (mesylate), —OTf (triflate); or

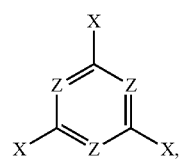

where Z is independently chosen from CH and nitrogen and X is independently at each occurrence chosen from a phenazine unit, co-monomer unit, —F, —Cl, —Br, —I, —CH═O, —OR, and the like, where —OR is —OTs (tosylate), —OMs (mesylate), —OTf (triflate). A phenazine may comprise a combination of the cross-linking units described herein.

Phenazine copolymers have various structures. A phenazine copolymer may have the following structure:

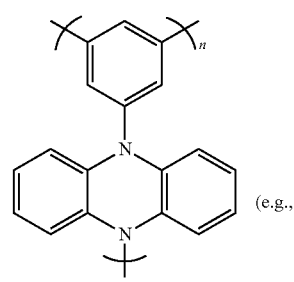

(e.g.,

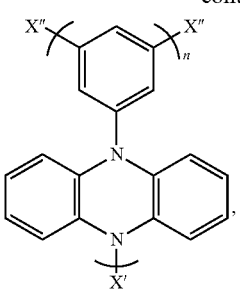

where X' is a cross-linking unit or —H and X" is a phenazine unit, —F, —Cl, —Br, —I, —CH=O, —OR, or the like, where —OR is —OTs (tosylate), —OMs (mesylate), —OTf (triflate)),

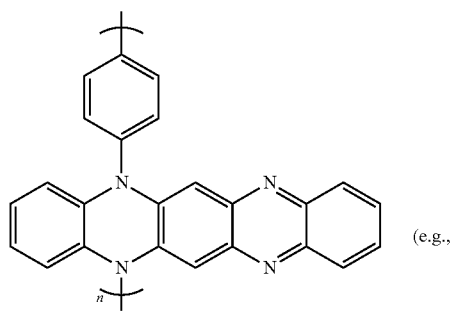 (e.g.,

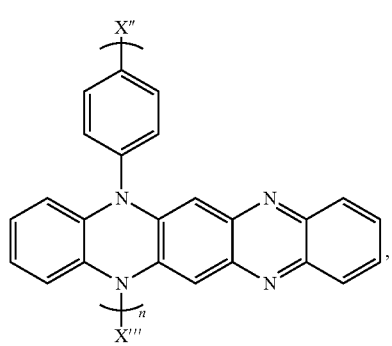, where X''' is a co-monomer unit or —H and X" is a phenazine unit, —F, —Cl, —Br, —I, —CH=O, —OR, or the like, where —OR is —OTs (tosylate), —OMs (mesylate), —OTf (triflate)),

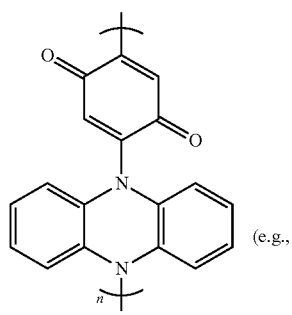 (e.g.,

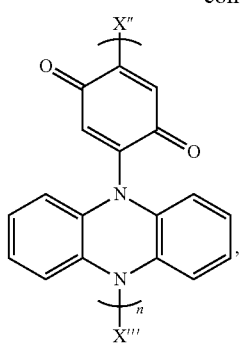, where X''' is a co-monomer unit or —H and X" is a phenazine unit, —F, —Cl, —Br, —I, —CH=O, —OR, or the like, where —OR is —OTs (tosylate), —OMs (mesylate), —OTf (triflate)),

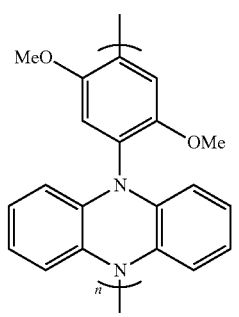

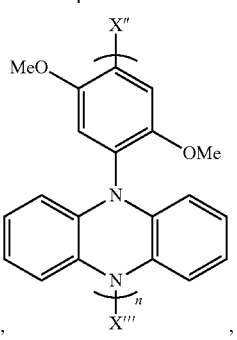

(e.q., 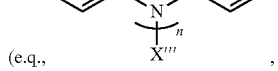, where X''' is a co-monomer unit or —H and X" is a phenazine unit, —F, —Cl, —Br, —I, —CH=O, —OR, or the like, where —OR is —OTs (tosylate), —OMs (mesylate), —OTf (triflate)),

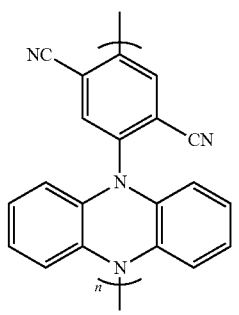

-continued

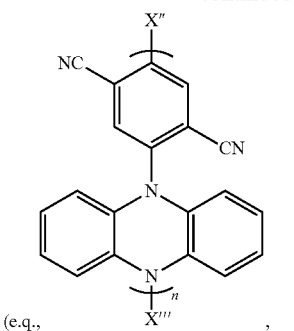

(e.q., [structure shown]), where X''' is a co-monomer unit or —H and X'' is a phenazine unit, —F, —Cl, —Br, —I, —CH=O, —OR, or the like, where —OR is —OTs (tosylate), —OMs (mesylate), —OTf (triflate)),

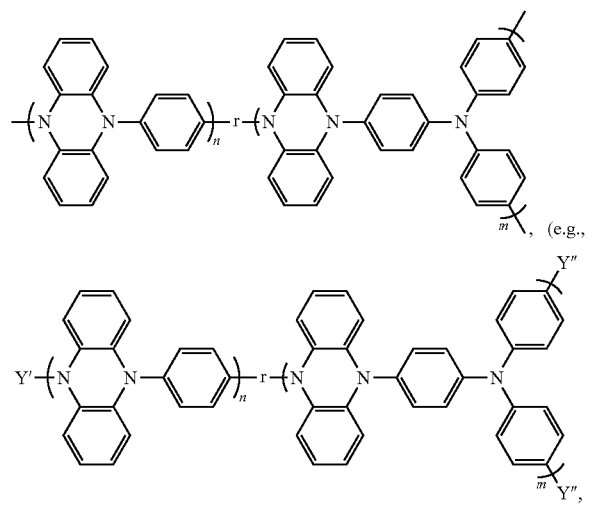

where Y' is a co-monomer unit, a cross-linking unit, or —H and Y'' is a phenazine unit, —F, —Cl, —Br, —I, —CH=O, —OR, or the like, where —OR is —OTs (tosylate), —OMs (mesylate), —OTf (triflate)),

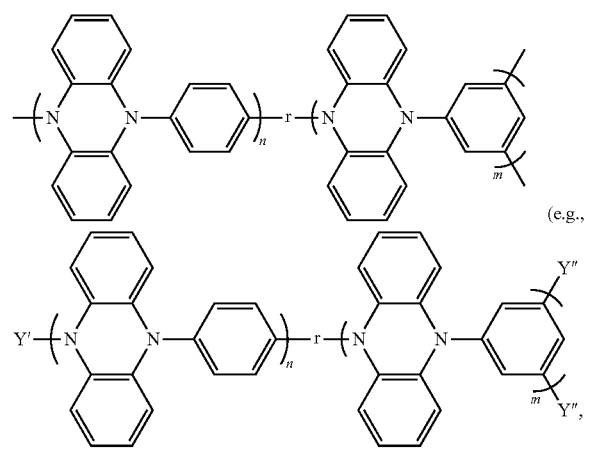

where Y' is a co-monomer unit, a cross-linking unit, or —H and Y'' is a phenazine unit, —F, —Cl, —Br, —I, —CH=O, —OR, or the like, where —OR is —OTs (tosylate), —OMs (mesylate), —OTf (triflate)), or a substituted analog (as described herein) thereof, where n is the number of repeating units, which may be determined by equations (1) and/or (2) and/or (10) described above, and r indicates random (e.g., the units may appear in random order). The number of repeating units (e.g., n, m, or a combination thereof) may be 3 to 1,000, including every integer value and range therebetween. In various examples when both n and m are present, n and/or m is 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, or a range or a range with bounds chosen therefrom. In various examples, a phenazine copolymer may comprise different cross-linking units (e.g., a first portion of the cross-linking units are:

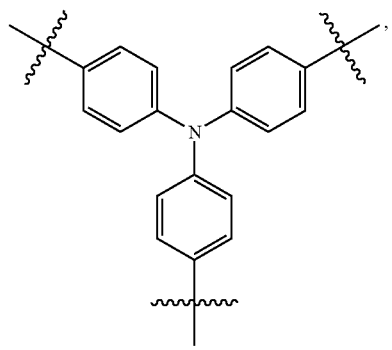

and a second portion of the cross-linking units are:

-continued

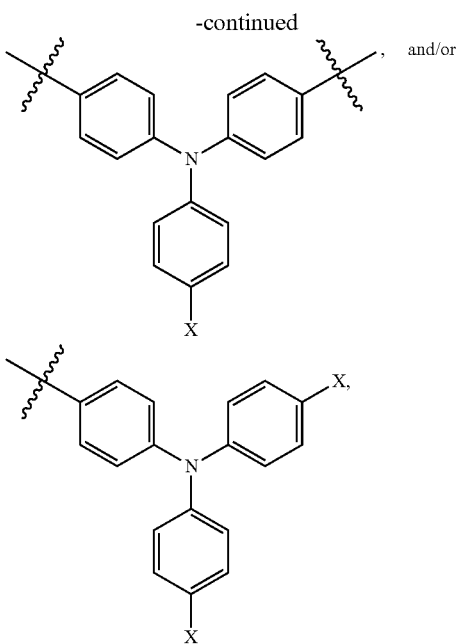

, and/or where X is independently at each occurrence chosen from a phenazine unit, —H, —F, —Cl, —Br, —I, —CH=O, and —OR, wherein —OR is —OTs (tosylate), —OMs (mesylate), —OTf (triflate)).

Cross-linking of phenazine copolymers may be defined by the amount of cross-linking precursor used to synthesize the phenazine copolymer. In various examples, the phenazine copolymer comprises 0-40 mol % (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mol %) cross-linking units derived from the following structure:

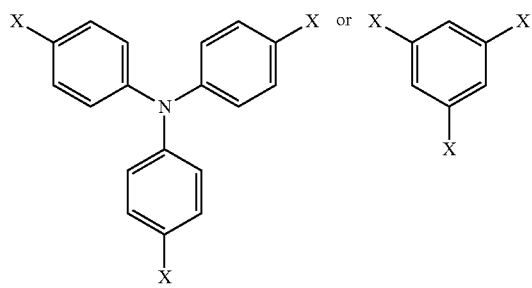

where X is independently at each occurrence chosen from a phenazine unit, —F, —Cl, —Br, —I, —CH=O, —OR, and the like, where —OR is —OTs (tosylate), —OMs (mesylate), —OTf (triflate), where mol % is based on the total moles of the phenazine copolymer. In various other examples, a phenazine copolymer comprises 25 to 33 mol % (e.g., 25, 26, 27, 28, 29, 30, 31, 32, or 33 mol %).

A phenazine copolymer may have varying degrees of crosslinking. A phenazine copolymer may be 0 to 100% crosslinked, including all integer % values and ranges therebetween.

A phenazine copolymer can have various molecular weights. The molecule weight may be described as $M_w$ and/or $M_n$. The molecular weight (e.g., $M_w$ and/or $M_n$) of a phenazine copolymer is 400 g/mol to 200,000 g/mol, including every integer g/mol value and range therebetween, or more. Molecular weight may be determined by methods known in the art. Molecular weight may be determined by gel permeation chromatography using polystyrene standards.

A phenazine copolymer can have various end groups. Non-limiting examples of end groups include a phenazine unit, a cross-linking unit, a co-monomer unit, —H, —F, —Cl, —Br, —I, —CH=O, —OR, and the like, and combinations thereof, where —OR is —OTs (tosylate), —OMs (mesylate), or —OTf (triflate). A phenazine copolymer may have end groups individually at each occurrence chosen from a phenazine unit, a cross-linking unit, a co-monomer unit, —H, —F, —Cl, —Br, —I, —CH=O, and the like, and —OR, wherein —OR is —OTs (tosylate), —OMs (mesylate), or —OTf (triflate).

Phenazine copolymers may be disordered. A phenazine copolymer may have no observable crystalline domains, has 1% or less (by weight) crystalline domains, has 2% or less (by weight) crystalline domains, has 3% or less (by weight) crystalline domains, has 4% or less (by weight) crystalline domains, has 5% or less (by weight) crystalline domains, has 6% or less (by weight) crystalline domains, has 7% or less (by weight) crystalline domains, has 8% or less (by weight) crystalline domains, has 9% or less (by weight) crystalline domains, or has 10% or less (by weight) crystalline domains). The percentage of crystalline domains is based on the total weight of the phenazine copolymer.

In an aspect, the present disclosure provides methods of making phenazine copolymers. Non-limiting examples of methods are provided herein. A phenazine copolymer may be made by a method of the present disclosure.

Phenazine copolymers may be formed by a reaction of various phenazine precursors and/or co-monomer precursors and/or cross-linking precursors. In various examples, one or more phenazine precursor(s) is reacted with one or more co-monomer precursor(s) in the presence of a catalyst (e.g., a RuPhos ligand and RuPhos Pd G2 precatalyst, and the like) and a base (e.g., sodium tert-butoxide, and the like) to form a phenazine copolymer comprising phenazine units and co-monomer units (e.g., a reaction mixture is formed comprising a catalyst, a base, and one or more phenazine precursor(s) and one or more co-monomer precursor(s) and the reaction mixture is stirred such that a phenazine copolymer is formed from the reaction of the one or more phenazine precursor(s) and one or more co-monomer precursor(s)). In various examples, one or more phenazine precursor(s), one or more co-monomer precursor(s), and one or more cross-linking precursor(s) are reacted in the presence of a catalyst (e.g., a RuPhos ligand and RuPhos Pd G2 precatalyst, and the like) and a base (e.g., sodium tert-butoxide, and the like) to form a phenazine copolymer comprising phenazine units, co-monomer units, and cross-linking units (e.g., a reaction mixture is formed comprising a catalyst, a base, one or more phenazine precursor(s), co-monomer precursor(s), and one or more cross-linking precursor(s) and the reaction mixture is stirred such that a phenazine copolymer is formed from the reaction of the one or more phenazine precursor(s) and one or more co-monomer precursor(s) and one or more cross-linking precursor(s)). In various examples, one or more phenazine precursor(s) is reacted with one or more cross-linking precursor(s) in the presence of a catalyst (e.g., a RuPhos ligand and RuPhos Pd G2 precatalyst, and the like) and a base (e.g., sodium tert-butoxide, and the like) to form a phenazine copolymer comprising phenazine units and cross-linking units (e.g., a reaction mixture is formed comprising a catalyst, a base, and one or more phenazine precursor(s) and one or more cross-linking precursor(s) and the reaction mixture is stirred such that a phenazine copolymer is formed from the reaction of the one or more phenazine precursor(s) and one or more cross-linking precursor(s)). Without intending to be bound by any particular theory, the various precursors are reacted under cross-coupling conditions (e.g., under an inert atmosphere, such as, for example, under nitrogen or argon atmosphere, using a catalyst (e.g., a RuPhos ligand and RuPhos Pd G2 precatalyst, and the like). A reaction mixture may comprise various solvents (e.g., toluene and the like). In various examples, the reaction mixture is heated (e.g., heated to an elevated temperature close to or at the boiling point of the solvent, such as, for example 110° C. for toluene).

A phenazine precursor may have the following structure:

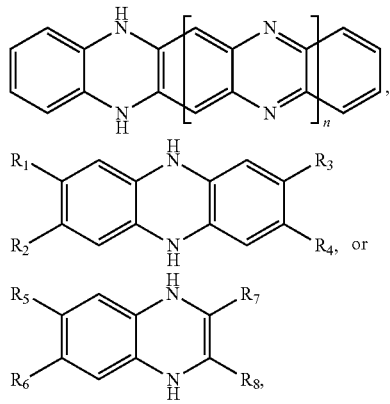

where $R_1$, $R_2$, $R_3$, $R_4$, $R_5$, $R_6$, $R_7$, and $R_8$ are independently at each occurrence chosen from —H, —F, —Cl, —I, —CH=O, and the like and n is 0 to 100, including every integer value and range therebetween (e.g., n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range or a range with bounds chosen therefrom).

A co-monomer precursor may have the following structure:

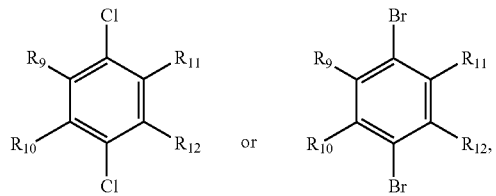

where $R_9$, $R_{10}$, $R_{11}$, and $R_{12}$ are independently at each occurrence chosen from —H, alkoxy groups (e.g., —OCH$_3$), —CN, alkyl groups (e.g., —CH$_3$, —(CH$_2$)$_n$CH$_3$ where n is 1, 2, 3, 4, 5, 6, 7, 8, 9, 10, 11, or 12)), heteroalkyl groups, such as, for example, thioether groups (e.g., —SCH$_3$), and the like; or

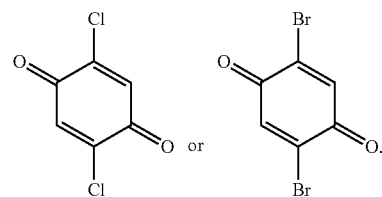 [SMILES: O=C1C=C(Cl)C(=O)C=C1Cl ; "or" ; O=C1C=C(Br)C(=O)C=C1Br]

A cross-linking precursor may have the following structure:

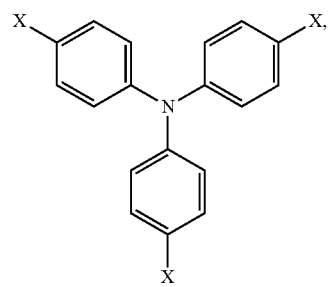

where X is independently at each occurrence chosen from —F, —Cl, —Br, —I, —CH=O, —OR, and the like, where —OR is —OTs (tosylate), —OMs (mesylate), —OTf (triflate); or

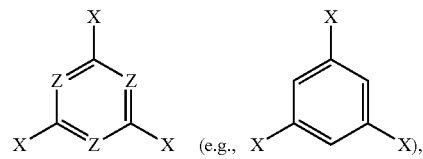

where Z is independently chosen from CH and nitrogen and X is independently at each occurrence chosen from —F, —Cl, —Br, —I, —CH=O, —OR, and the like, where —OR is —OTs (tosylate), —OMs (mesylate), —OTf (triflate). A phenazine copolymer may comprise a combination of the cross-linking units described herein.

A phenazine unit may be derived from a phenazine precursor. A co-monomer unit may be derived from a co-monomer precursor. A cross-linking unit may be derived from a cross-linking precursor.

Phenazine copolymers of the present disclosure may be made by various methods. For example, polymers may be made by electropolymerization, palladium-coupled addition polymerization, and nucleophilic aromatic substitution reactions.

In an aspect, the present disclosure provides cathodes. The cathodes can be used in devices such as, for example, batteries, superconductors, and the like. The cathodes comprise one or more phenazine copolymer of the present disclosure. Non-limiting examples of cathodes are provided herein.

A cathode may comprise one or more layers, each layer independently comprising one or more phenazine copolymer(s). The individual layers can have various thickness. An individual layer of phenazine copolymer of a cathode may have a thickness of 1-500 microns, including every 0.1 values and ranges therebetween.

Cathodes may further comprise various carbon materials. Non-limiting examples of carbon materials include Super-P® carbon, carbon paper, and the like, and combinations thereof. The carbon material may be conducting. Suitable carbon materials are known in the art.

Cathodes may further comprise various binder materials. Non-limiting examples of binder materials include polymer materials, such as, for example, thermoplastic polymers (e.g., polyvinylidene-fluoride (PVDF)). Suitable other binder materials are known in the art.

In various examples, a cathode comprises carbon materials and/or binder materials. Suitable other materials for electrodes are known in the art.

Cathodes may further comprise a current collector. The current collector may be a carbon paper current collector where the phenazine copolymer is a film or a component of a film disposed on the current collector. Various other current collectors (e.g., aluminum-based current collectors and/or copper-based current collectors) may be used.

In an aspect, the present disclosure provides devices. The devices comprise one or more phenazine copolymer of the present disclosure, which may be part of one or more cathode, and/or one or more phenazine copolymer formed by a method of the present disclosure, which may be part of one or more cathode.

A device may be a battery (e.g., a rechargeable/secondary battery, such as, for example, a lithium-ion conducting, potassium-ion conducting, magnesium-ion conducting, aluminum-ion conducting, or sodium-ion conducting rechargeable/secondary battery), such as an ion-conducting battery. Non-limiting examples of devices are provided herein. Additional non-limiting examples of suitable ion-conducting batteries include zinc-ion batteries, as well as organic-ion batteries, such as tetrabutylammonium-ion, hexafluorophosphate-ion, perchlorate-ion, tetrafluoroborate-ion, bis(trifluoromethanesulfonyl)imide-ion, bis(fluorosulfonyl)imide-ion, trifluoromethanesulfonate-ion, and bis(oxalate)borate-ion. A battery may comprise a phenazine copolymer, such as, for example, a cathode comprising a phenazine copolymer as described herein.

A battery as described herein may further comprise an anode. Non-limiting examples of anodes include metal anodes, such as, for example, a lithium metal anode, a potassium metal anode, a sodium metal anode, a magnesium metal anode, an aluminum metal anode, or the like. Anodes may be organic anodes (e.g., organic-based polymer anodes). Other non-limiting examples of anodes include organic anodes, such as, for example, poly(anthraquinones) and polymers containing Schiff bases.

A battery may comprise various additional components. Non-limiting examples of additional components include one or more electrolyte and/or one or more current collector and/or one or more additional structural components (e.g., bipolar plates, external packaging, electrical contacts/leads to connect wires, and combinations thereof).

A battery may comprise a plurality of cells (e.g., 1-500 cells, including every integer value and range therebetween). Each cell may comprise one or more cathode comprising a phenazine copolymer of the present disclosure.

A battery may comprise charge carriers that are not metal ions. The metal ions may serve as compensating ions. Examples of non-metal ion charger carriers include, but are not limited to, halides, boron-containing anions, phosphorus-containing anions, nitrogen-containing cations and anions, tetrabutylammonium, hexafluorophosphate, perchlorate, tetrafluoroborate, bis(trifluoromethanesulfonyl)imide, bis(fluorosulfonyl)imide, trifluoromethanesulfonate, and bis(oxalate)borate. Non-limiting examples non-metal ion charge carriers include $(C_4H_9)_4N^+$, $F^-$, $Cl^-$, $Br^-$, $HF_2^-$, $BH_4^-$, $OCN^-$, $HCO_2^-$, $HCO_2^-$, $BrO_3^-$, $HS^-$, $NO_3^-$, $SCN^-$, $CH_3COO^-$, $BF_4^-$, $B(CH_3)_4^-$, $B(Ph)_4^-$, $PF_6^-$, $AsF_6^-$, $ClO_4^-$, $CF_3SO_3^-$, $(CF_3SO_2)_2N^-$, $(CF_3SO_2)_2CH^-$, $(CF_3SO_2)_3C^-$, $(C_2F_5SO_2)N^-$, $(FSO_2)_2N^-$, $B(C_2O_4)_2^-$, $B(C_3O_4H_2)_2^-$, $B(C_3O_4H_2)(C_2O_4)$, $B(C_6O_4H_2)_2^-$, $B(C_6H_4O_2)_2^-$, $B(C_6F_4O_2)_2^-$, $B(C_{10}H_6O_2)_2^-$, $B(C_{12}H_8O_2)_2^-$, $B(C_7H_4O_3)_2^-$, $PF_5(CF_3)^-$, $PF_4(CF_3)_2^-$, $PF_3(CF_3)_3^-$, $PF_3(C_2F_5)_3^-$, $P(C_6H_4O_2)_3^-$, $N_5^-$, $N_5C_2^-$, $N_5C_4^-$, $N_5C_4^-$, $N_5C_4^-$, $N_5C_2^-$, $N_5C_2^-$, $N_5C_2^-$, $N_5C_{10}^-$, $N_2C_3H_3(BF_3)_2^-$, $Al(C_3HF_6O)_4^-$, $N(CN)_2^-$, and $C(CN)_3^-$.

Without intending to be bound by any particular theory, it is considered that a battery of the present disclosure may function as a dual ion battery. For example, a battery does not function by intercalation of the metal cation at the cathode. In another example, a battery functions by the interaction of cations with the anode and anions with the cathode to balance charge. (This contrasts with typical metal-ion batteries in which typically the cation is shuttled back and forth to interact with both electrodes.)

It is desirable that the phenazine copolymer be insoluble in both the charged and uncharged state in the battery electrolyte. Polymer chain length, cross-linking the polymer, and electrolyte properties maybe selected in order to prevent dissolution of the polymer.

A battery may exhibit desirable properties. For example, a battery exhibits desirable areal capacity (e.g., areal capacity of 0.1 mAh/cm² or greater and/or capacity (e.g., when discharging at 5 C to 1.5 V vs. Li/Li⁺, from cycle 50 to cycle 500, a battery exhibits a retention of capacity of at least 90%, at least 95%, or at least 98%. The central redox active unit comprising one or more phenazine group polymerized through a tertiary amine results in polymer with high redox potentials (>2.5 V vs. Li/Li⁺, desirable stability, and desirable charge transfer kinetics, translating to desirable energy and power densities with desirable cycling stability.

The steps of the method described in the various embodiments and examples disclosed herein are sufficient to carry out the methods of the present disclosure. Thus, in an embodiment, a method consists essentially of a combination of the steps of a method disclosed herein. In another embodiment, a method consists of such steps.

The following Statements describe various non-limiting examples of the present disclosure:

Statement 1. A phenazine copolymer comprising: a plurality of phenzine units; and a plurality of co-monomer units (e.g., aryl-halide coupling units) or a plurality of cross-linking units or both a plurality of co-monomer units and a plurality of cross-linking units, where the individual phenazine units are covalently bonded to a co-monomer unit and/or a cross-linking unit. For example, $$a1+(b2+x3) \rightarrow \text{phenazine copolymer}$$

$$b+3/2x=a$$

or

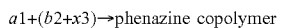

where 1 is the phenazine units and/or 2 is the co-monomer units and/or 3 is the cross-linking units and/or a is the amount of the phenazine units and/or b is the amount of the co-monomer units and/or x is the amount of the cross-linking units and/or n is the number of reactive sites in the cross-linking unit. The ratios of phenazine units to co-monomers and/or cross-linking monomer units may be determined by equations (1) and/or (2) and/or (3). In various examples, a is greater than 0, b is greater than or equal to zero (e.g., b is greater than 0), x is greater than or equal to zero (e.g., x is greater than 0), and n is greater than or equal to 3. For example, when a is equal to 1, b is 0.7 to 1.1 (e.g., 0.9), and x is 0.05 to 0.08 (e.g., 0.067). In various other examples, when b is equal to 1, a is 0.8 to 1.2 (e.g., 1) and x is 0.05 to 0.08 (e.g., 0.067). In various examples, a is 1, b is 0 to 1 (e.g., 0.25 to 0.50) and x is 0 to 0.66 (e.g., 0.33 to 0.50).

Statement 2. The phenazine copolymer according to Statement 1, where at least a portion of or all of the phenazine units have the following structure:

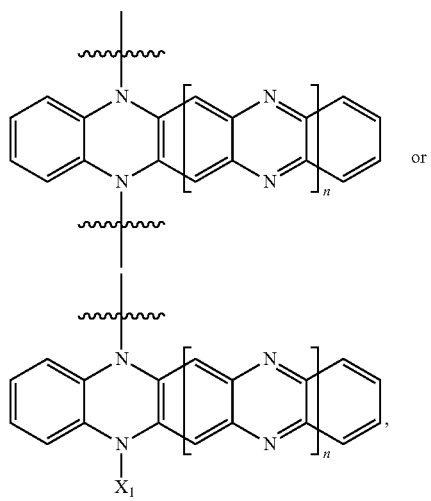

or

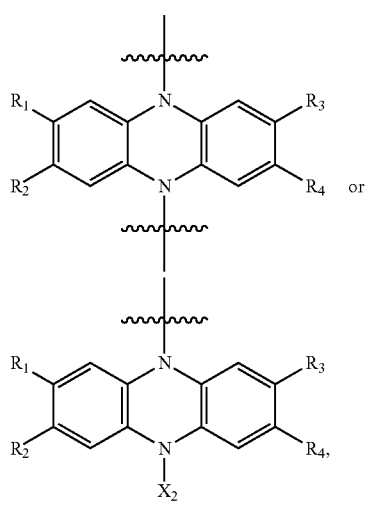

where n is 0 to 100 (e.g., n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range or a range with bounds chosen therefrom) and $X_1$ is chosen from a co-monomer unit, a cross-linking unit, and —H;

where $R_1$, $R_2$, $R_3$, $R_4$ are independently at each occurrence chosen from —F, —Cl, —Br, —I, —CH=O, and the like and $X_2$ is chosen from a co-monomer unit, a cross-linking unit, and —H;

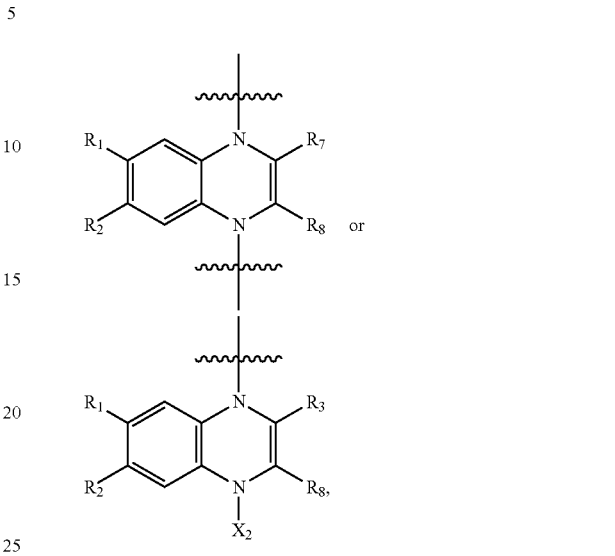

where $R_5$, $R_6$, $R_7$, $R_8$ are independently at each occurrence chosen from —F, —Cl, —Br, —I, —CH=O, and the like and $X_3$ is chosen from a co-monomer unit, a cross-linking unit, and —H; or a combination thereof.

Statement 3. The phenazine copolymer according to Statements 1 or 2, where at least a portion of or all of the co-monomer units have the following structure:

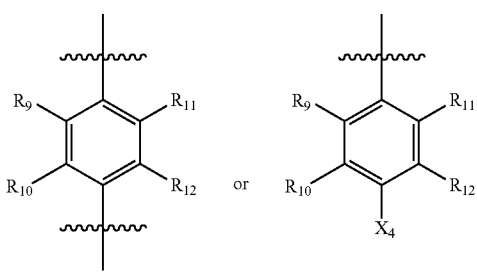

where $R_9$, $R_{10}$, $R_{11}$, $R_{12}$ are independently at each occurrence chosen from —H, —OCH$_3$, —CN, —CH$_3$, —(CH$_2$)$_n$CH$_3$, wherein n is 1 to 12 (e.g., 1, 2, 3, 4, 5, 6, 7, 8, 9, 10, 11, or 12), —SCH$_3$, and the like and $X_4$ is chosen from a phenazine unit, —H, —F, —Cl, —Br, —I, —CH=O, —OR, and the like, where —OR is —OTs (tosylate), —OMs (mesylate), —OTf (triflate); or

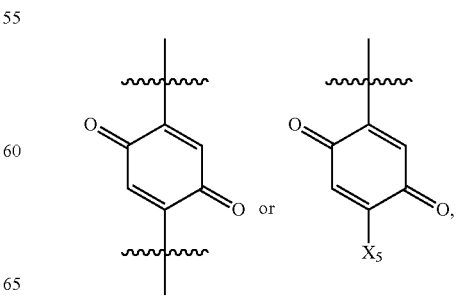

where $X_5$ is chosen from a phenazine unit, a cross-linking unit, —H, —F, —Cl, —Br, —I, —CH=O, —OR, and the like, where —OR is —OTs (tosylate), —OMs (mesylate), —OTf (triflate); or a combination thereof.

Statement 4. The phenazine copolymer according to any one of the preceding Statements, where at least a portion of or all of the cross-linking units have the following structure:

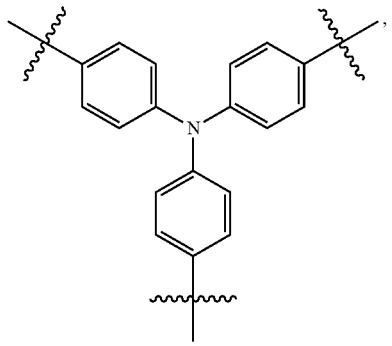,

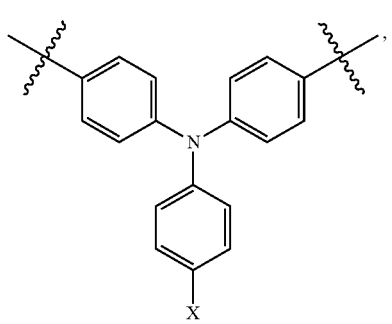,

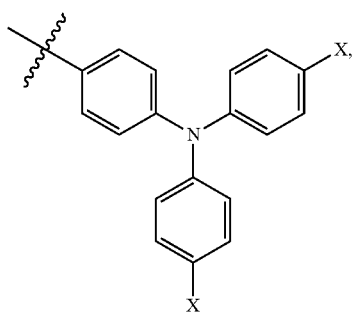, wherein X is independently at each occurrence chosen from a phenazine unit, —H, —F, —Cl, —Br, —I, —CH=O, —OR, and the like, where —OR is —OTs (tosylate), —OMs (mesylate), —OTf (triflate);

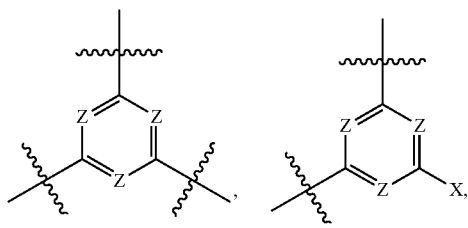

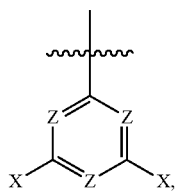

where Z is nitrogen or CH and X (e.g., Z is CH) is independently at each occurrence chosen from a phenazine unit, —H, —F, —Cl, —Br, —I, —CH=O, —OR, and the like, where —OR is —OTs (tosylate), —OMs (mesylate), —OTf (triflate); or a combination thereof.

Statement 5. The phenazine copolymer according to any one of the preceding Statements, where the phenazine copolymer has the following structure:

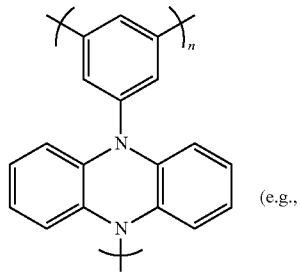 (e.g.,

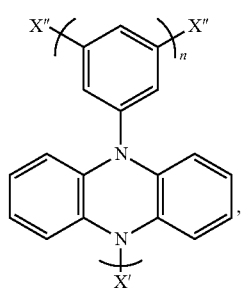, where X' is a cross-linking unit or —H and X" is a phenazine unit, —F, —Cl, —Br, —I, —CH=O, —OR, or the like, where —OR is —OTs (tosylate), —OMs (mesylate), —OTf (triflate)),

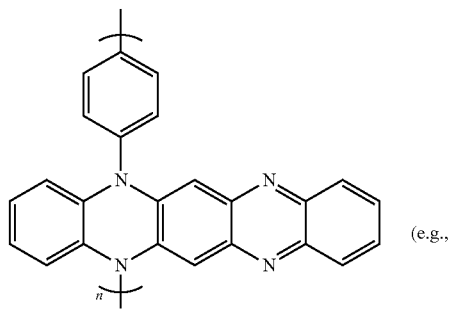 (e.g.,

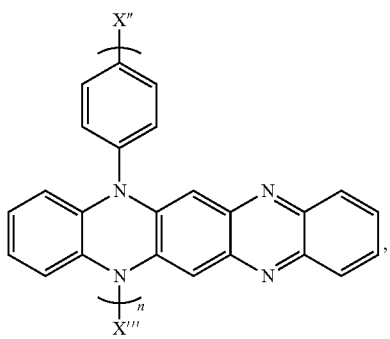

where X''' is a co-monomer unit or —H and X" is a phenazine unit, —F, —Cl, —Br, —I, —CH=O, —OR, or the like, where —OR is —OTs (tosylate), —OMs (mesylate), —OTf (triflate)),

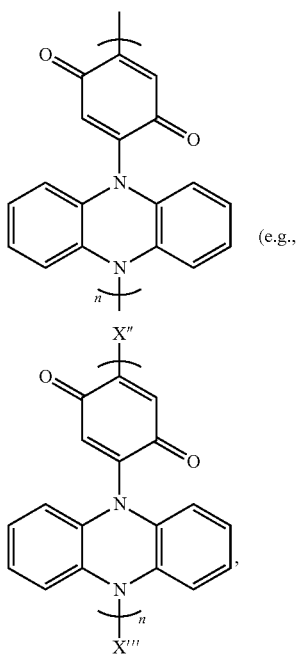

(e.g., where X''' is a co-monomer unit or —H and X" is a phenazine unit, —F, —Cl, —Br, —I, —CH=O, —OR, or the like, where —OR is —OTs (tosylate), —OMs (mesylate), —OTf (triflate)),

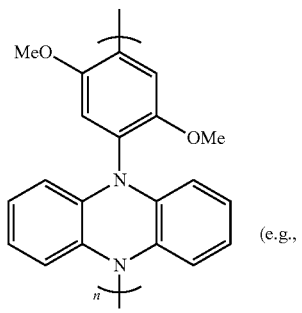

(e.g.,

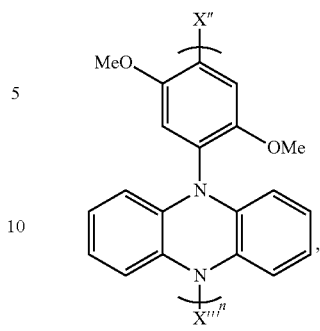

where X''' is a co-monomer unit or —H and X" is a phenazine unit, —F, —Cl, —Br, —I, —CH=O, —OR, or the like, where —OR is —OTs (tosylate), —OMs (mesylate), —OTf (triflate)),

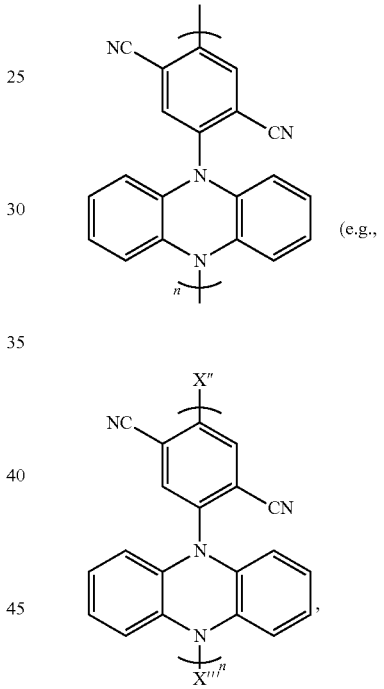

(e.g., where X''' is a co-monomer unit or —H and X" is a phenazine unit, —F, —Cl, —Br, —I, —CH=O, —OR, or the like, where —OR is —OTs (tosylate), —OMs (mesylate), —OTf (triflate)),

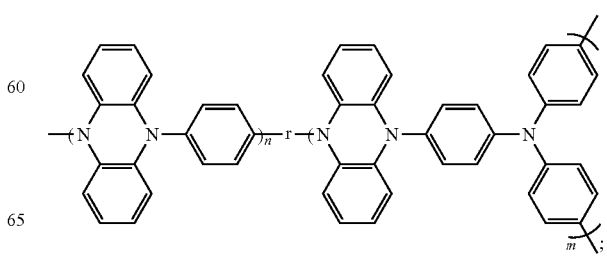

(e.g.,

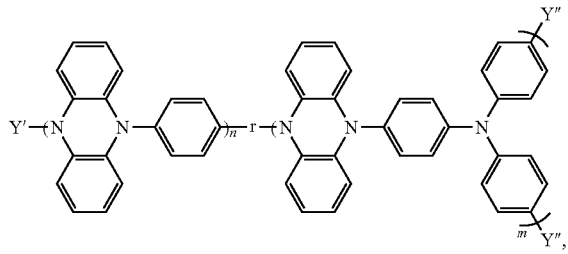

where Y' is a co-monomer unit, a cross-linking unit, or —H and Y" is a phenazine unit, —F, —Cl, —Br, —I, —CH=O, —OR, or the like, where —OR is —OTs (tosylate), —OMs (mesylate), —OTf (triflate)),

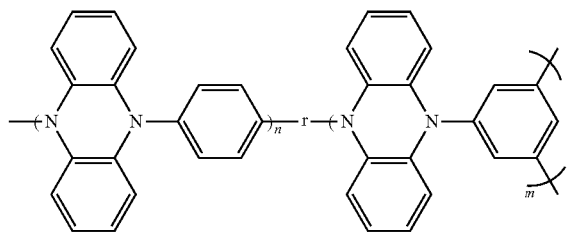

(e.g.,

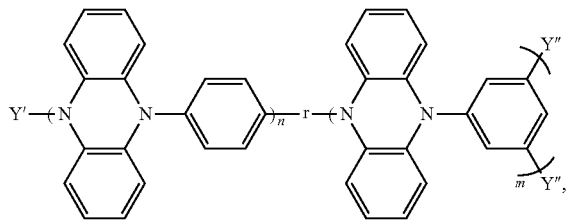

where Y' is a co-monomer unit, a cross-linking unit, or —H and Y" is a phenazine unit, —F, —Cl, —Br, —I, —CH=O, —OR, or the like, where —OR is —OTs (tosylate), —OMs (mesylate), —OTf (triflate)),
or an analog (e.g., a substituted analog) (as described herein) thereof where n is determined by equations (1) and/or (2) and/or (10). r indicates random (e.g., the units may appear in random order).

Statement 6. The phenazine copolymer according to any one of the preceding Statements, where the phenazine copolymer has a molecular weight (e.g., $M_w$ and/or $M_n$) of 400 to 200,000 g/mol and/or Statement 7. The phenazine copolymer according to any one of the preceding Statements, wherein the phenazine copolymer comprises 0 to 40 mol % one or more cross-linking unit(s) (e.g., 25 to 33 mol %).

Statement 8. The phenazine copolymer according to any one of the preceding Statements, where the phenazine copolymer has an amorphous, globular morphology. E.g., the phenazine copolymer has no observable crystalline domains.

Statement 9. The phenazine copolymer according to any one of the preceding Statements, wherein the phenazine copolymer is disordered. E.g., the phenazine copolymer has 10% or less, 9% or less, 8% or less, 7% or less, 6% or less, 5% or less, 4% or less, 3% or less, 2% or less, or 1% or less (by weight) crystalline domains.

Statement 10. A cathode comprising a phenazine copolymer according to any one of Statements 1-9. E.g., wherein the cathode comprises a layer of a composite material (e.g., having a thickness of 1-500 microns).

Statement 11. The cathode according to Statement 10, further comprising carbon material(s) (e.g., Super-P® carbon, carbon paper, and the like, and combinations thereof) and/or one or more various binder material(s) (e.g., polymer materials such as, for example, thermoplastic polymers). The carbon material(s) may be conducting. Polyvinylidenefluoride (PVDF) is a non-limiting example of a suitable binder material. Examples of suitable additional materials for electrodes (e.g., carbon materials and binder materials) are known in the art.

Statement 12. The cathode according to Statement 10 or Statement 11, where the cathode further comprises a current collector (e.g., a carbon paper current collector) and the phenazine copolymer is present as film or a component of a film disposed on the current collector. Other current collectors may be used, such as, for example, aluminum and copper.

Statement 13. A device comprising a phenazine copolymer according to any one of Statements 1-9.

Statement 14. The device according to Statement 13, where the device is a battery or a supercapacitor.

Statement 15. The device according to Statement 13 or Statement 14, where the device comprises a cathode according to any one of Statements 9-11.

Statement 16. The device according to Statement 14 or Statement 15, where the battery is an ion-conducting battery.

Statement 17. The device according to Statement 16, where the ion-conducting battery is a lithium-ion conducting battery, a potassium-ion conducting battery, a sodium-ion conducting battery, a magnesium-ion conducting battery, or an aluminum-ion conducting battery. Additional non-limiting ion conducting batteries include zinc-ion batteries as well as organic-ion batteries, such as tetrabutylammonium-ion, hexafluorophosphate-ion, perchlorate-ion, tetrafluoroborate-ion, bis(trifluoromethanesulfonyl)imide-ion, bis(fluorosulfonyl)imide-ion, trifluoromethanesulfonate-ion, and bis(oxalate)borate-ion batteries.

Statement 18. The device according to any one of Statements 14-17, where the battery further comprises an anode (e.g., a metal anode, such as, for example, a lithium metal anode, a potassium metal anode, a sodium metal anode, a magnesium metal anode, an aluminum metal anode, or the like) and/or one or more electrolyte(s) and/or one or more current collector(s) and/or one or more additional structural component(s). Organic-based polymer anodes may be used.

Statement 19. The device according to Statement 18, where the one or more additional structural component(s) is/are chosen from bipolar plates, external packaging, electrical contacts/leads to connect wires, and the like, and combinations thereof.

Statement 20. The device according to any one of Statements 14-19, where the battery comprises a plurality of cells, each cell comprising one or more cathode(s) of any one of Statements 10-12, and optionally, one or more anode(s), electrolyte(s), current collector(s), or a combination thereof.

Statement 21. The device according to Statement 20, where the battery comprises 1 to 500 cells, including all integer values and ranges therebetween.

Statement 22. The device according to any one of Statements 13-21, where charge carriers are not metal ions.

The following examples are presented to illustrate the present disclosure. They are not intended to be limiting in any matter.

Example 1

This example provides a description of polymers and batteries of the present disclosure and method of making and characterization of same.

Redox active polymers have been recognized for their potential as cathodes in electrical energy storage systems and are uniquely poised to deliver high energy and power densities. The electrochemical properties of phenazine, N,N'-dimethyl phenazine and N,N'-diphenyl phenazine were investigated and identified as promising energy storing, redox active moieties by cyclic voltammetry and linear sweep voltammetry at ultramicroelectrodes. By incorporating redox active phenazine into an insoluble material, we have developed a cathode material that stores charge at high potentials (3.5 V vs Li/Li$^+$) and delivers high energy densities. Discharge capacities (198 mAhg$^{-1}$) and capacity retention were improved by copolymerizing with tris(4-bromophenyl) amine to cross-link the polymer. The improvement is attributed to a decreased solubility of the polymer crosslinker, which is confirmed by UV-Vis spectroscopy. Owing to the facile charge transfer kinetics and amorphous nature of the material, it is able to deliver high power load facilitating charge propagation; 120 mAh g$^{-1}$ at 120 C. This polymer undergoes charge compensation through ion pairing with anions in the electrolyte solution, meaning its electrochemical performance is largely independent of the cations in solution. This concept was demonstrated by pairing the polymer in a coin cell with a sodium anode, where capacities greater than 160 mAh g$^{-1}$ were demonstrated. Herein, a phenazine-based polymer, with optimized polymer architecture, is presented which delivers high energy and power densities.

It was hypothesized that a stable high voltage polymeric material could be synthesized through careful examination of the redox active components as small molecule analogues. Through this approach, an organic material containing redox active small molecule fragments that have been structurally tuned to stabilize the oxidized states and enable facile electron transfer was designed. The material tests the upper limits of the solvent potential window, delivering high energy densities at high rates, while offering compatibility with multiple metallic anodes.

Figure 10:
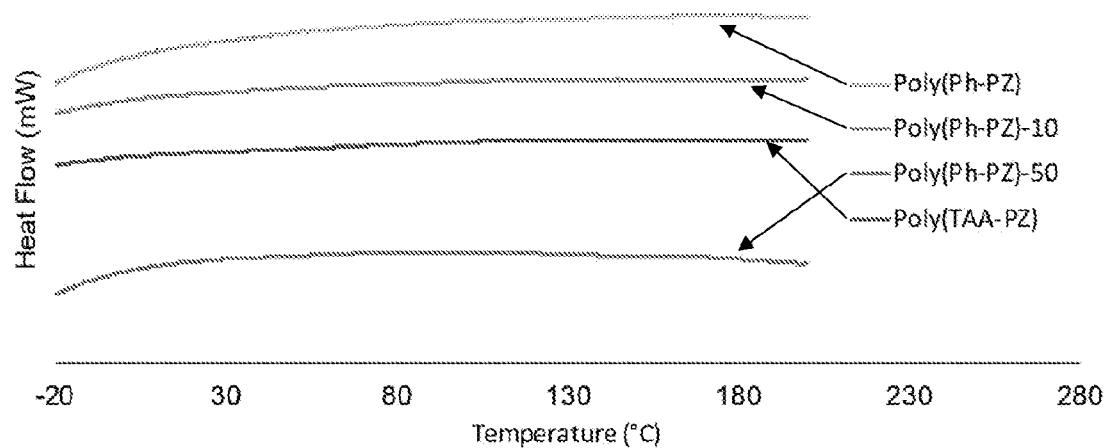
FIG. 10 shows differential scanning calorimetry (DSC) traces of the second heat of poly(Ph-PZ), poly(Ph-PZ)-10, poly(Ph-PZ)-50, and poly(TAA-PZ).
Figure 11:
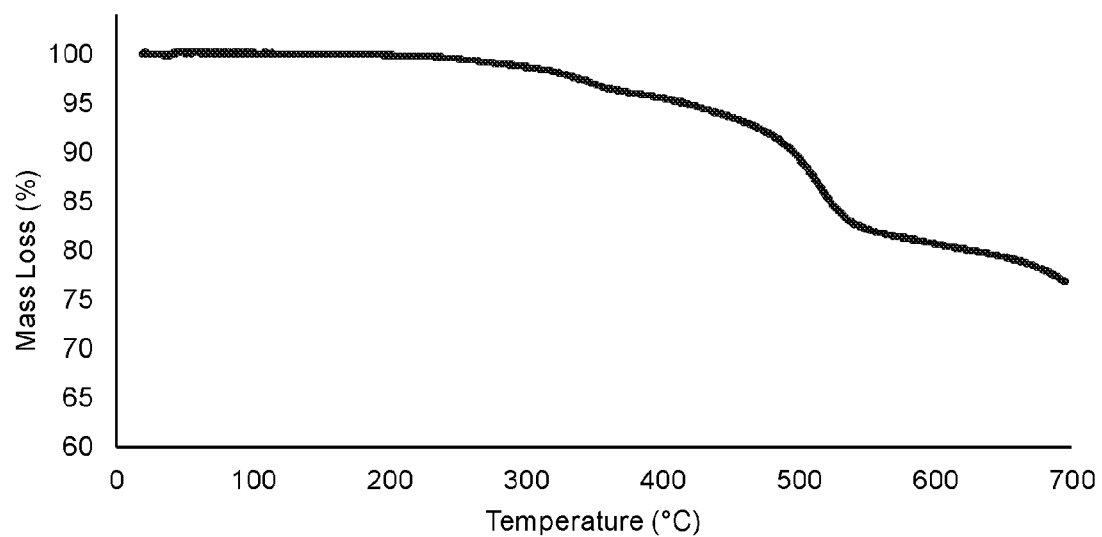
FIG. 11 shows thermogravimetric Analysis (TGA) of poly(Ph-PZ).

Phenazine (1) has been identified as a promising charge storage unit, in cathodes, capacitors, and as a redox flow catholyte. The electrochemical properties of phenazine was examined by cyclic voltammetry as shown in FIG. 1. Phenazine undergoes two reductions at a glassy carbon electrode in acetonitrile with 0.1 M tetrabutylammonium perchlorate (TBAP) electrolyte. The first reduction at −0.96 V vs SCE is reversible, while the second redox event (−1.31 V) is electrochemically irreversible as observed by the large $\Delta E_{peak}$ (Table 1) and the decreasing $i_{p,a}/i_{p,c}$ with increasing scan rate (FIG. 10). The addition of acid to the electrolyte solution improved the second redox event through the protonation of the reduced phenazine (FIG. 11). However, the $\Delta E_{peak}$ of the first redox event increased, likely due to the kinetics of the associated protonation. Based on these results, phenazine utilized as a battery electrode material should provide high capacities, at low C-rates. Therefore, the reversibility of the electron transfer steps in phenazine was sought to be improved through substitution at the nitrogen of phenazine.

By alkylating or arylating phenazine, the resulting small molecules are neutral in the reduced form. The standard potentials of both N,N'-diphenylphenazine (2), and N,N'-dimethylphenazine (3) shifted by over 1500 mV and 2000 mV from the standard potentials of the phenazine couples. Thus, incorporation of N-substituted phenazine cathode materials in electrochemical energy storage (EES) devices is expected to result in desirable operating voltages and lead to desirable energy densities.

TABLE 1

Values for peak splitting and standard rate constants for phenazine small molecule derivatives.

| Material | $\Delta E_{peak\,1}$ (0→±1) | $\Delta E_{peak\,2}$ (±1→±2) | $k^0_1$ (cm/s) | $k^0_2$ (cm/s) |
|---|---|---|---|---|
| Phenazine | 58 mV | 216 mV | $2.6 \times 10^{-2}$ | — |
| Phenazine +50 mM TFA | 107 mV | 65 mV | $1.4 \times 10^{-2}$ | $1.6 \times 10^{-2}$ |
| N,N'-dimethyl-phenazine | 86 mV | 58 mV | $9.3 \times 10^{-3}$ | $8.5 \times 10^{-3}$ |
| N,N'-diphenyl phenazine | 65 mV | 66 mV | $1.1 \times 10^{-2}$ | $9.3 \times 10^{-3}$ |

Withstanding the demands of continued battery cycling requires stability in all redox states and reversible electron transfers. Phenazine (1), N,N'-diphenylphenazine (2), and N,N'-dimethylphenazine (3) all exhibit a reversible first electron transfer. The reversibility of the second electron transfer is improved in 2 and 3 as observed by the narrowing of the $\Delta E_{peak}$ to the ideal reversible value of 58 mV (Table 1). Additionally, a convergence to unity of $i_{p,a}/i_{p,c}$ is observed in both 2 and 3 when compared to phenazine (Table 3). This suggests that the cationic and dicationic states of 2 and 3 are more stable than the reduced states of phenazine. Both the alkylated and arylated phenazine molecules show improved electrochemical stability which should translate to a long, stable cycle life and high rate capabilities when incorporated into a cathode battery material.

Figure 2:
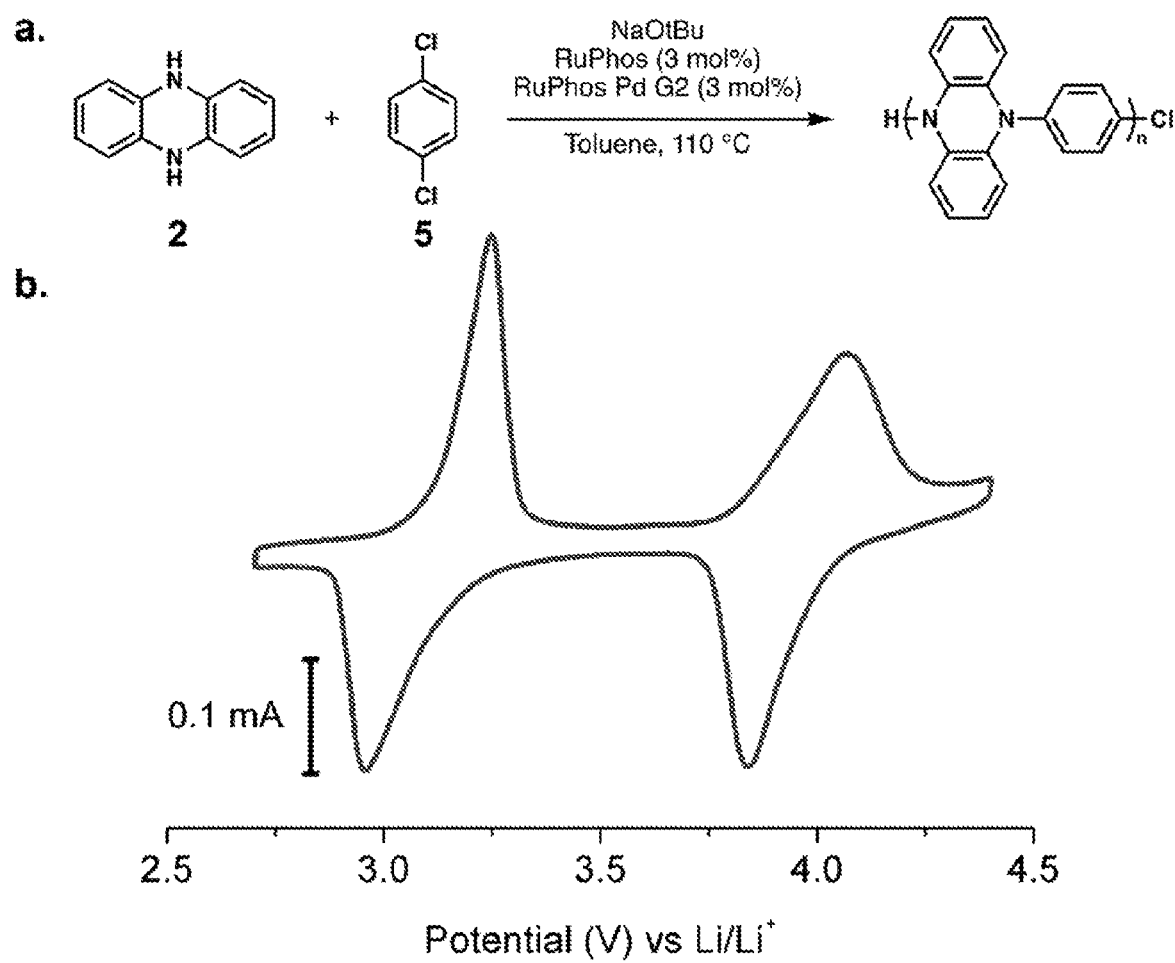
FIG. 2 shows (a.) schematic of synthesis of poly(Ph-PZ) (b.) CV of poly(Ph-PZ) in a Li metal coin cell with 1M LiPF$_6$ in EC/DEC at 2 mV/s.
Figure 3:
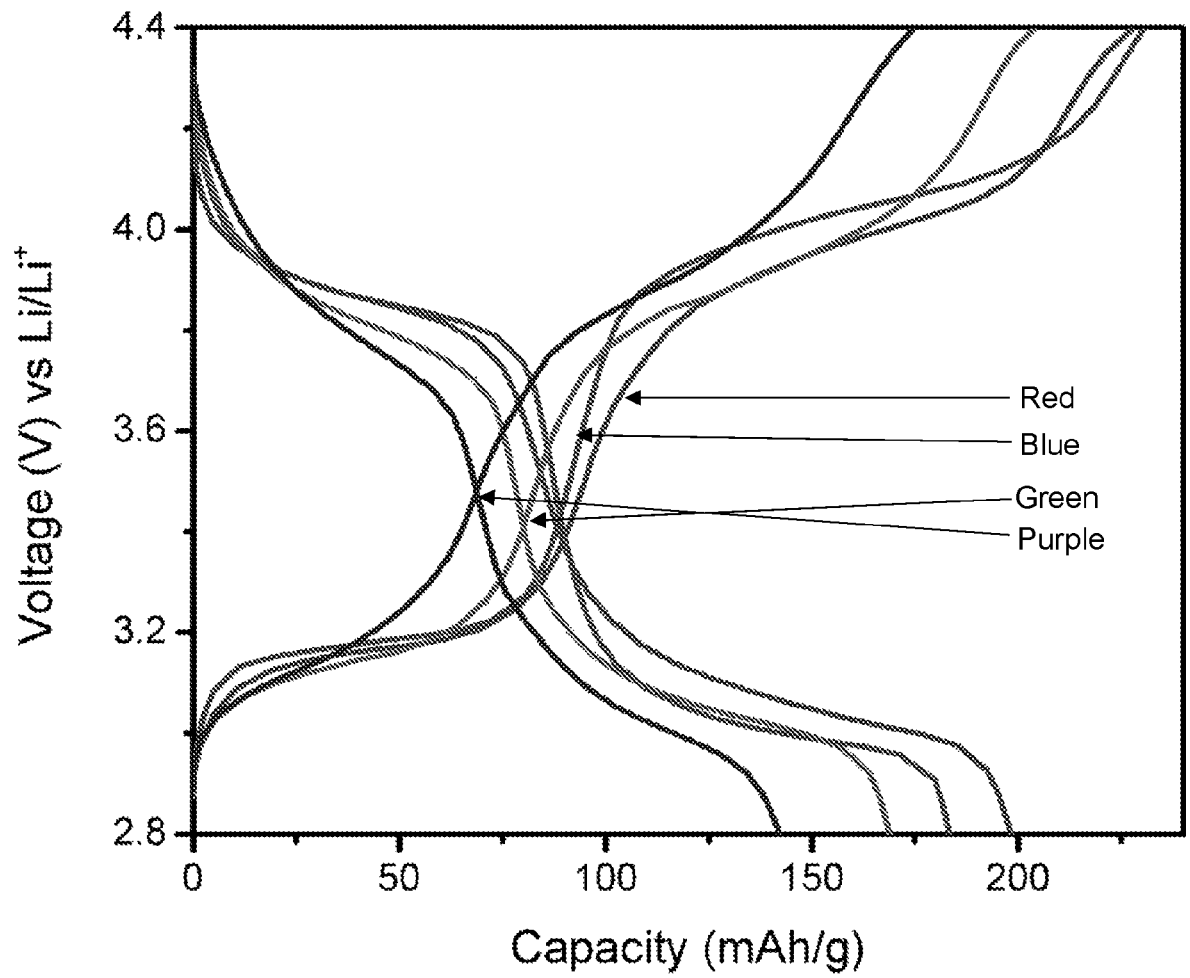
FIG. 3 shows charge/discharge profiles of poly(Ph-PZ) (blue), 10% CL poly(Ph-PZ) (red), 50% CL poly(Ph-PZ) (green), and poly(triarylamine-PZ) (purple) at 0.5 C-rate.
Figure 4:
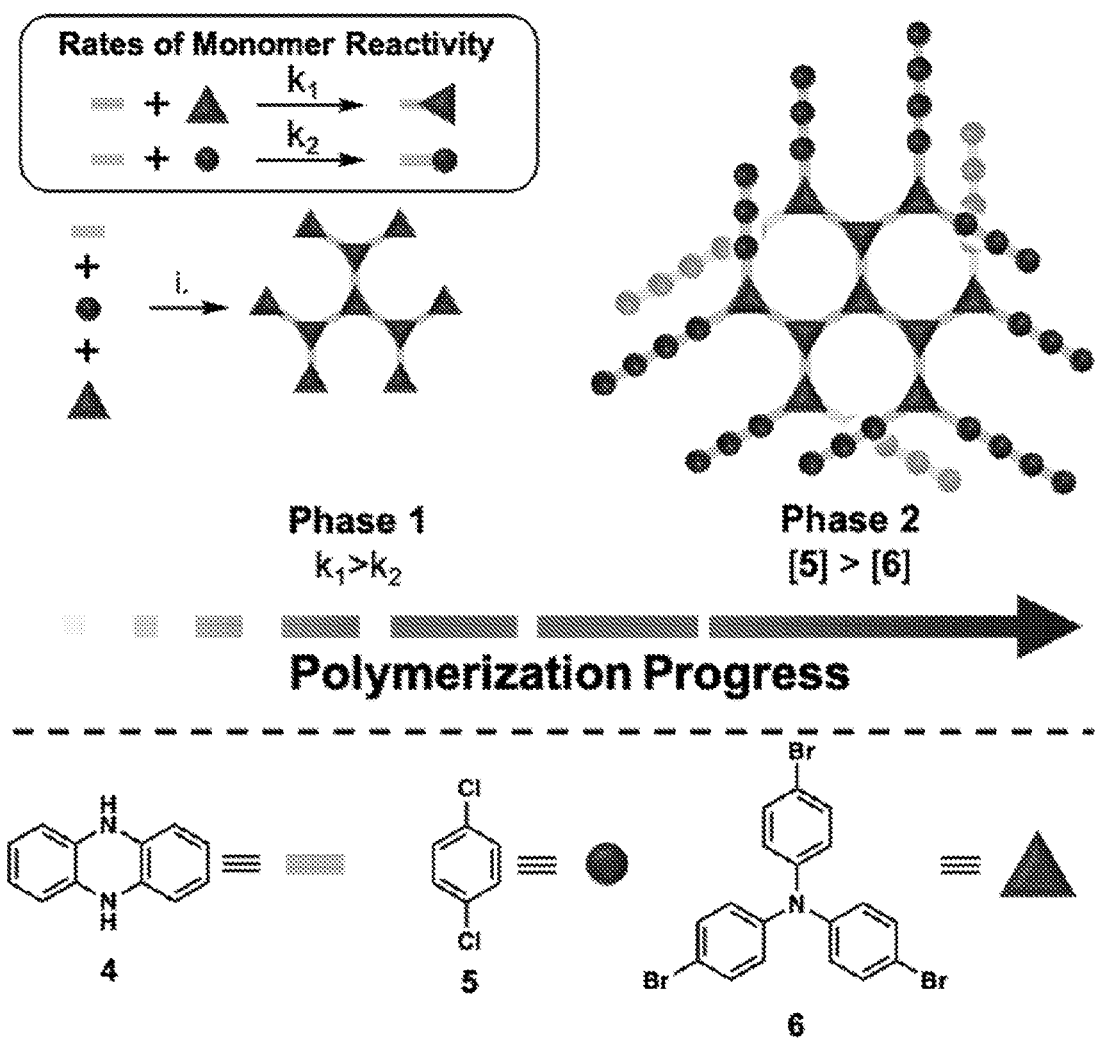
FIG. 4 shows copolymerization of 9,10-dihydrophenazine 4, dichlorobenzene 5, tris(4-bromophenyl) amine 6, to achieve a polymer with a branching core unit resulting from the fast cross-coupling between aryl-bromide 6 with diamine 4, and linear arms resulting from the cross-coupling between 4 with 5 once 6 is depleted.

A poly(phenyl phenazine), (poly(Ph-PZ)), cathode was prepared as a composite with Super P, CMK-3, poly(phenyl phenazine), and poly(vinylidene difluoride) (PVDF) in a 3:3:3:1 ratio. The material delivered a capacity of 183 mAh g$^{-1}$ at 0.5 C upon discharge, approximately 88 percent of its theoretical capacity of 209 mAh g$^{-1}$ (FIG. 3). As expected and consistent with FIG. 2, two discrete plateaus are observed in the discharge profile at 3.05 V and 3.85 V vs Li/Li$^+$, respectively.

TABLE 2

Reaction equivalents used in Buchwald-Hartwig cross-coupling reactions to obtain a branched polymer architecture.

| Polymer | 9,10-dihydro-phenazine(4) (equiv) | 1,4-dichlorobenzene (5) (equiv) | Tris(4-bromophenyl) amine (6)(equiv) |
|---|---|---|---|
| Poly(Ph-PZ) | 1.0 | 1.0 | 0 |
| Poly(Ph-PZ)-10 | 1.0 | 0.90 | 0.067 |
| Poly(Ph-PZ)-50 | 1.0 | 0.5 | 0.033 |
| Poly(TAA-PZ) | 1.0 | 0.0 | 0.667 |

The difference between experimental and theoretical discharge capacity is attributed to polymer dissolution from the electrode. It was hypothesized that altering the polymer's architecture could decrease the polymers solubility under oxidative conditions. It was envisaged that the addition of tris(4-bromophenyl) amine (6) to the polymerization would result in a branched structure (FIG. 2). Because oxidative insertion of the Pd(0) catalyst into the aryl bromide, 6, is faster than oxidative insertion into the aryl chloride, 5, polymerization between 4 and 6 will occur first, generating a branched core. Once, the concentration of 6 decreases, the rate of cross-coupling of 4 with 5 will begin to outcompete cross-coupling with 6 resulting in linear arms branching away from the core. Two monomer feed ratios were investigated to achieve this architecture and presented in Table 2. Elemental analysis of the polymers revealed that 0.0 percent bromine content and 1.19 percent chlorine content in poly(Ph-PZ)-10. This suggests that a branching structure was achieved since no aryl-bromide end groups remained. By contrast, elemental analysis of poly(Ph-PZ)-50 revealed 0.54 percent bromine content and 0.67 percent chlorine content. The presence of bromine in the poly(Ph-PZ)-50, suggests that the size of the branched core exceeded its solubility in the reaction conditions and precipitated out before assembly of the arms.

Figure 5:
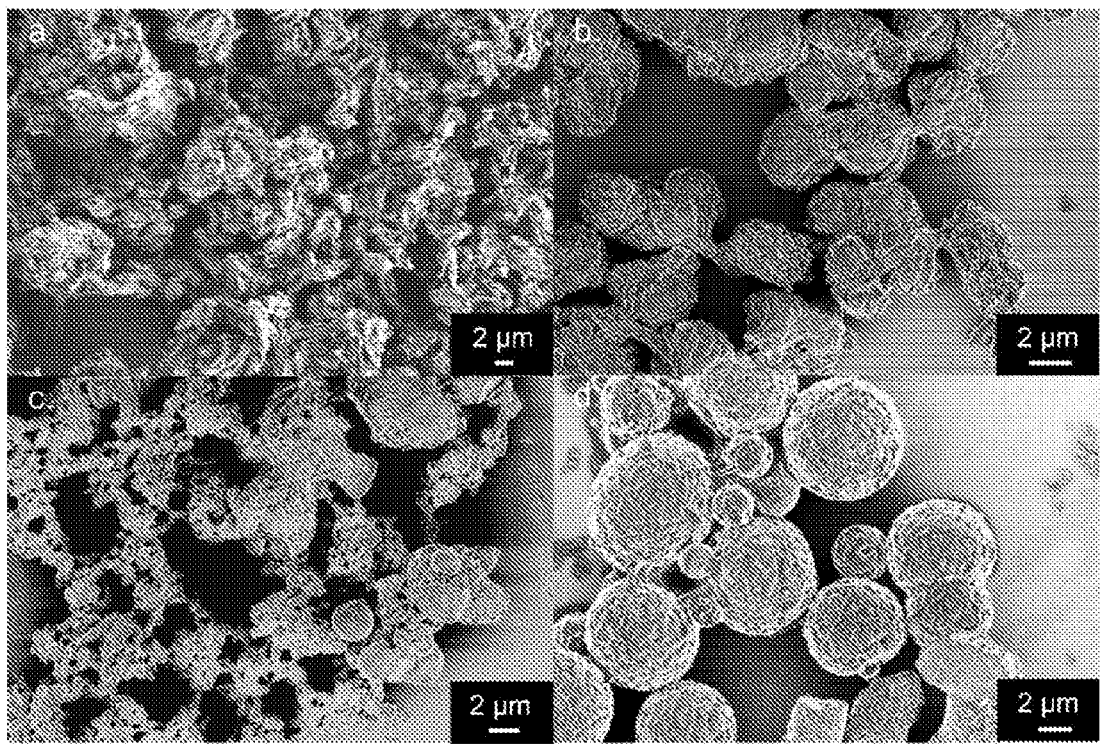
FIG. 5 shows SEM images of (a.) poly(Ph-PZ) (b.) poly(Ph-PZ)-10 (c.) poly(Ph-PZ)-50 and (d.) poly(TAA-PZ).
Figure 16:
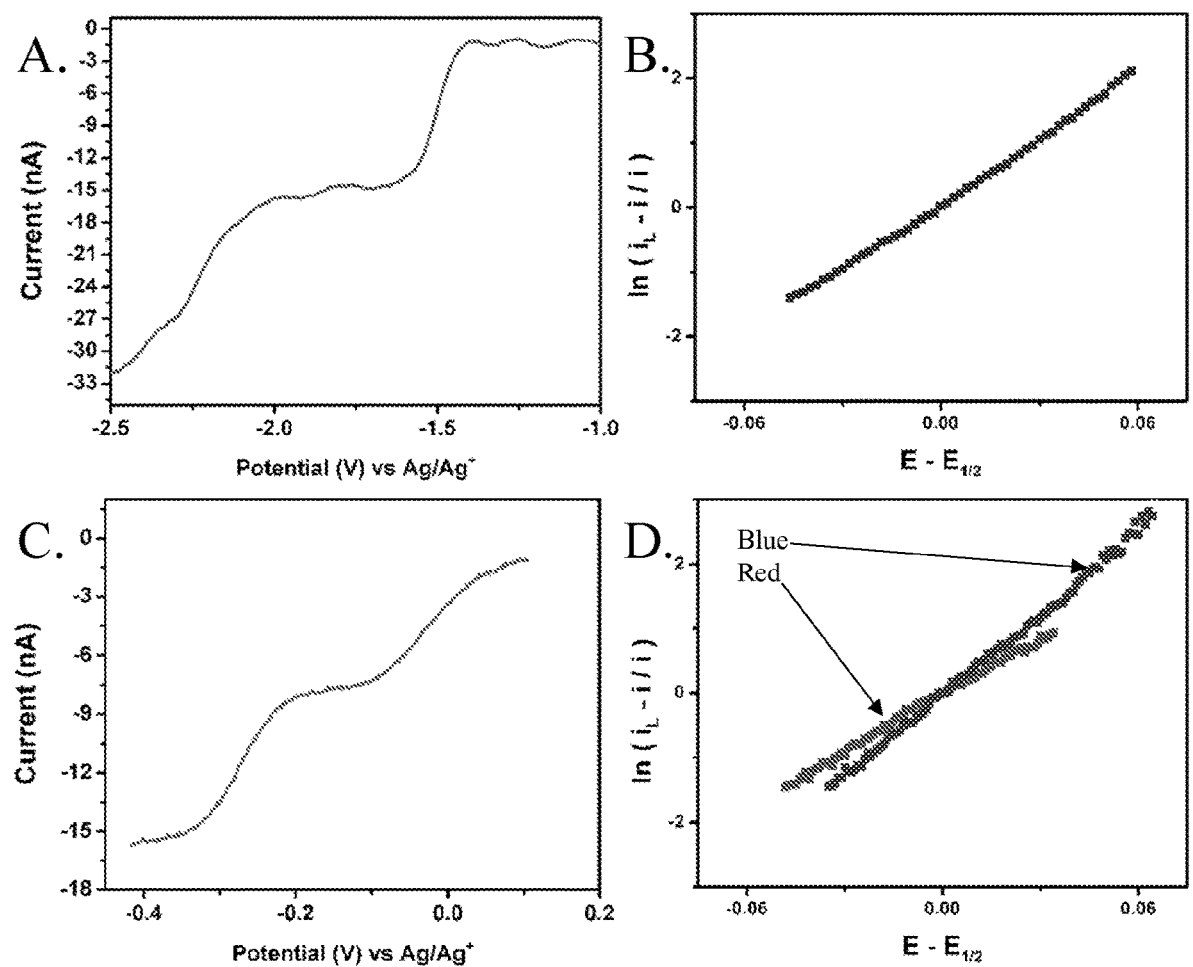
FIG. 16 shows Steady state curves at ultramicro electrodes (UME). Steady state curves (a,c,e,g) at 20 mV/s and linear fits for $k_s$ (b,d,f,h) for the first electron transfer (red) and the second electron transfer (blue) from UME studies for phenazine (a,b), phenazine with 50 mM TFA (c,d), dimethyl phenazine (e,f), and diphenyl phenazine (g,h).
Figure 16:
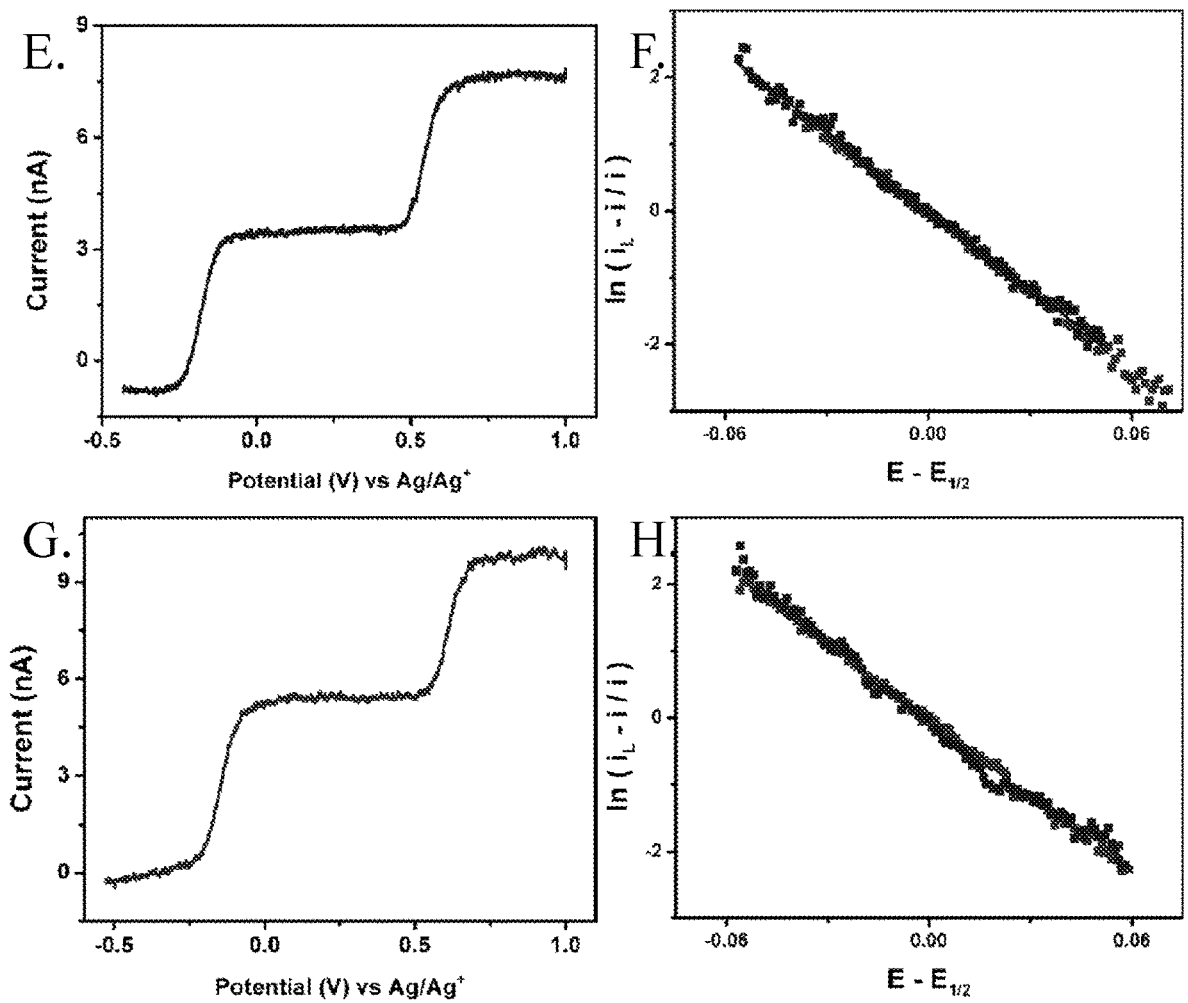
Figure 17:
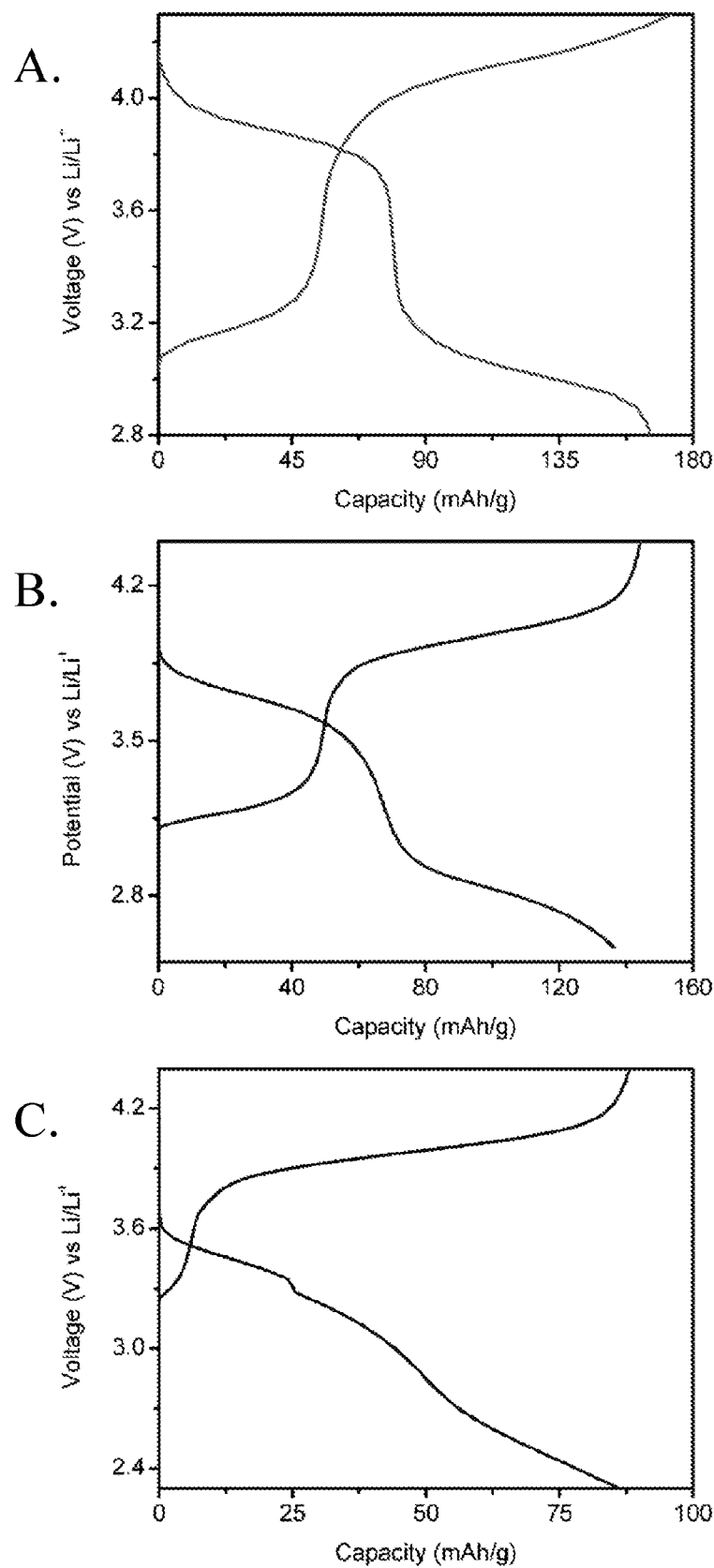
FIG. 17 shows Charge/discharge curves of poly(Ph-PZ)-10 at varying rates. Charge/discharge curves of poly(Ph-PZ)-10 in a lithium coin cell with a mass ratio of 6:1.5:1.5:1 of active material:Super P:CMK-3:PVDF at varied discharge rates: (a.) 1 C (b.) 20 C (c.) 120 C.
Figure 18:
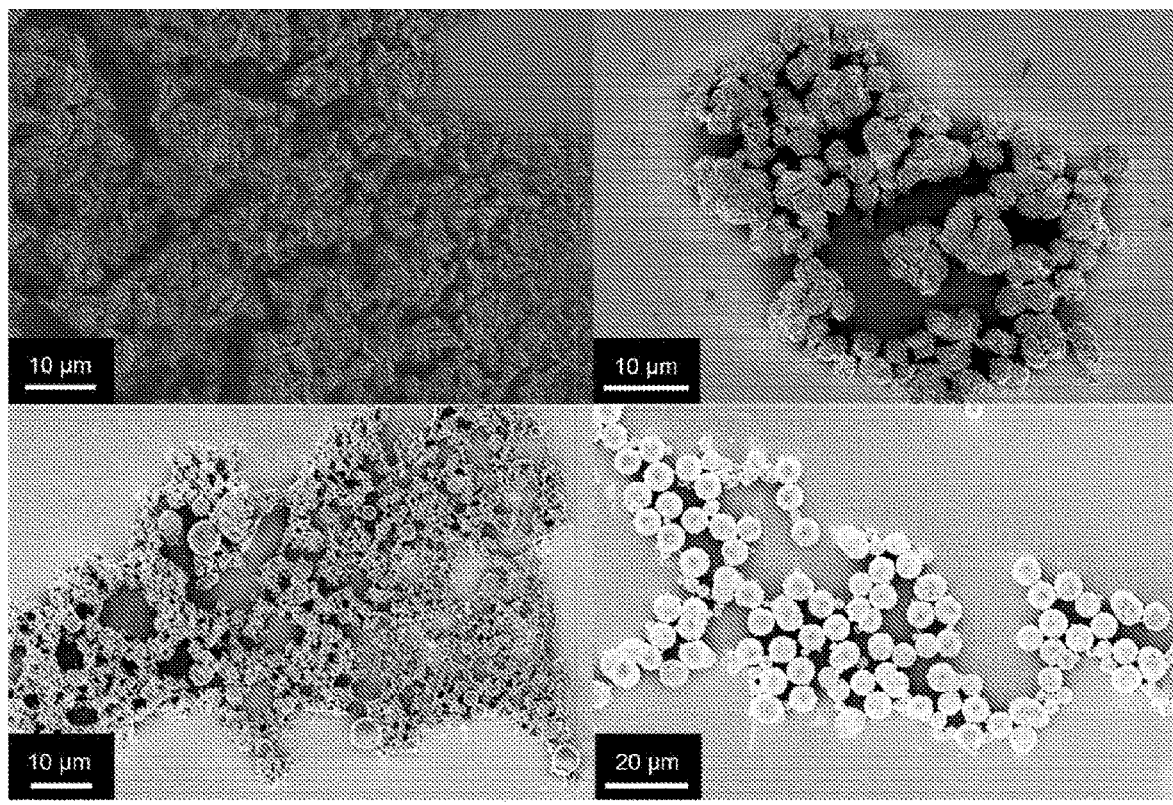
FIG. 18 shows SEM images of polymers. (a.) poly(Ph-PZ), (b.) poly(Ph-PZ)-10, (c.) poly(Ph-PZ)-50, and (d.) poly(TAA-PZ).
Figure 19:
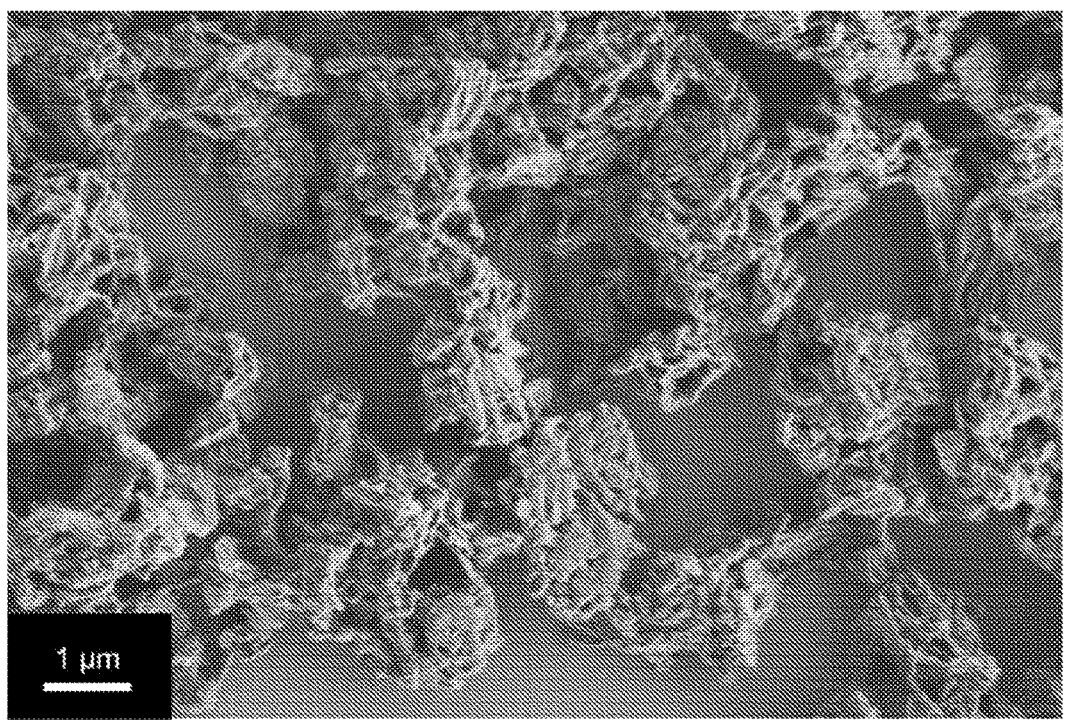
FIG. 19 shows SEM image of poly(Ph-PZ)-10 made from cross coupling 9,10-dihydro-phenazine with dibromobenzene and tris(4-bromophenyl) amine.

The morphology of the polymer architectures was investigated by scanning electron microscopy (SEM). Poly(Ph-PZ) in FIG. 5a, shows a lack of a defined morphology, although the polymer appears to be porous. FIG. 5b shows an image of poly(Ph-PZ)-10, revealing that through the addition of a small amount of 6, the morphology of the resulting polymer is dramatically changed. Poly(Ph-PZ)-10 exhibits a "bow-tie" like morphology, which is expected to provide pathways for fast ion transport. The observed morphology supports the hypothesis of a branched core with arms of 5 extending outward. When the amount of 6 added is increased in poly(Ph-PZ)-50, a new morphology developed, seen in FIG. 5c. The polymer appears as spherical particles entangled on a porous polymer skeleton. Poly(triarylamine-phenazine) (poly(TAA-PZ), shown in FIG. 5d, appears to be entirely made up of the spherical particles seen in the poly(Ph-PZ)-50 sample, implying that the polymerization of 4 with 6 favors this spherical morphology. To show that the morphology is both, an effect of the monomer used in the cross-coupling reaction, as well as the rate of polymerization, a sample of poly(Ph-PZ)-10 was made with dibromobenzene in place of 5. The obtained polymer yielded a much less defined morphology than that of poly(Ph-PZ)-10 formed with dichlorobenzene (FIG. 16).

Figure 6:
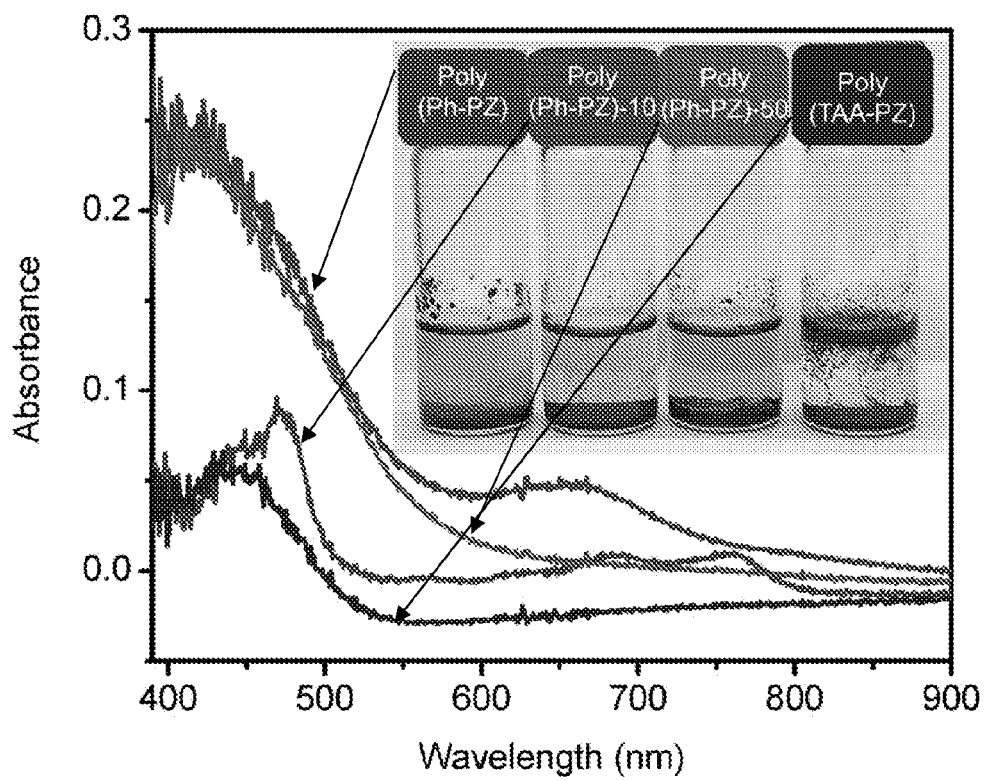
FIG. 6 shows absorbance spectra of solutions of 1M LiPF$_6$ in EC/DEC with poly(Ph-PZ), poly(Ph-PZ)-10, poly(Ph-PZ)-50, and poly(TAA-PZ) after 1 week. Inset shows pictures of solutions immediately before the absorbance spectra was taken.

To determine the effect of the polymer architecture on solubility, UV-vis spectroscopy was utilized to determine the solubility of each. Ten milligrams of each polymer were placed in separate vials and 1.5 mL of 1 M $LiPF_6$ in EC/DEC were added to each to mimic the ratio of active material to electrolyte in a typical coin-cell environment. The vials were left undisturbed for seven days and most of the material remained undissolved. To determine the extent to which any small amount of the polymers dissolved, UV-vis spectra were collected for each of the samples. The UV-Vis spectra of the solutions are overlaid in FIG. 6. Poly(Ph-PZ)-10 and poly(TAA-PZ) exhibit a lower absorbance peak and were determined to have the highest resilience to dissolution. This suggested that altering the polymer architecture influences their solubility. Thus, the capacity delivered and stability, under continued cycling, is expected to strongly depend on the obtained architecture.

Indeed, as the active cathode material in a lithium half-cell, the poly(Ph-PZ)-10 exhibited a discharge capacity of 198 mAh $g^{-1}$ (FIG. 3). Since, 10 percent of a non-active cross-linker has been incorporated in the polymer, the theoretical capacity decreased to 204 mAh $g^{-1}$. Thus, the measured capacity of the material constitutes 97 percent of its theoretical value. Due to the larger percent of the inactive cross-linker, the poly(Ph-PZ)-50 delivers a capacity of 169 mAh $g^{-1}$; 93 percent of its theoretical capacity. Similarly, the capacity of the poly(TAA-PZ) is only 142 mAh $g^{-1}$. Finding the optimal polymer architecture to minimize dissolution while minimally effecting capacity is essential to designing a high energy cathode material. At an average discharge voltage of 3.45 V, the poly(Ph-PZ)-10 exhibits one of the highest energy densities (about 700 Wh/kg of active material) of all polymeric cathodes.

Figure 7:
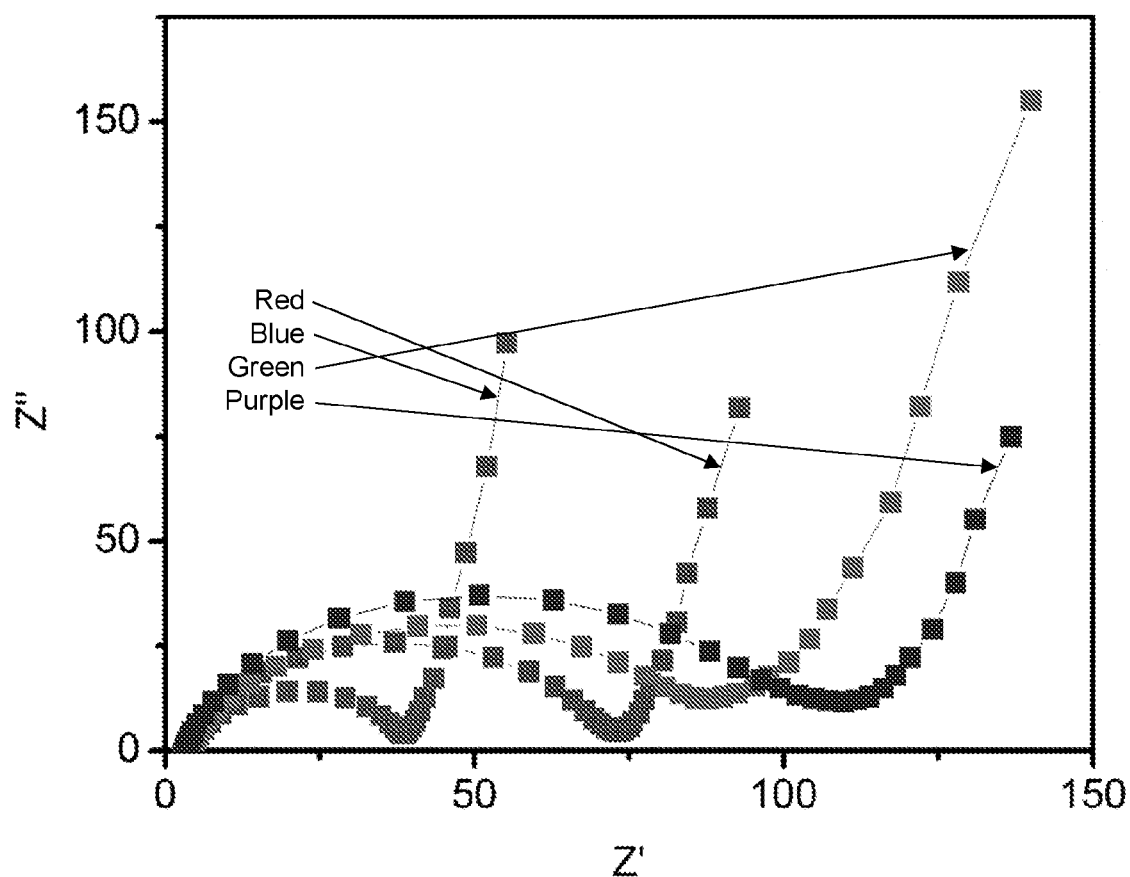
FIG. 7 shows impedance spectra of poly(Ph-PZ) (blue), poly(Ph-PZ)-10 (red), poly(Ph-PZ)-50 (green), and poly(TAA-PZ) (purple).

For high power applications, fast electron transfer and ion transport kinetics are necessary. The partially conjugated π system, dependent on charge state, is expected to enable faster electron transport through the material. Additionally, the amorphous nature of the polymer should allow for fast ion transport. To quantify these effects, electrochemical impedance spectroscopy (EIS) was used to measure the charge transfer resistance and the ion diffusion coefficients (FIG. 7). In the Nyquist plot, the diameter of the semicircle in the high frequency region is related to the charge transfer resistance in the cell. Upon increasing the percentage of 6 in the polymer, we observed an increase in the charge transfer resistance. This increase in resistance is attributed at least in part to the differences in the electrode material and its interfaces with the electrolyte and cell components. Still, all four polymers exhibited a low charge transfer resistance, enabling fast electron transport. Using the low frequency EIS data, the diffusion coefficients of the $PF_6^-$ were determined. For poly(Ph-PZ) and poly(Ph-PZ)-10 the obtained diffusion coefficients were $6.6 \times 10^{-10}$ $cm^2/s$ and $5.1 \times 10^{-10}$ $cm^2/s$, respectively. These values are orders of magnitude higher than those of commercial inorganic oxide cathodes, enabling high rate capabilities while maintaining a high utilization of the active material.

Figure 8:
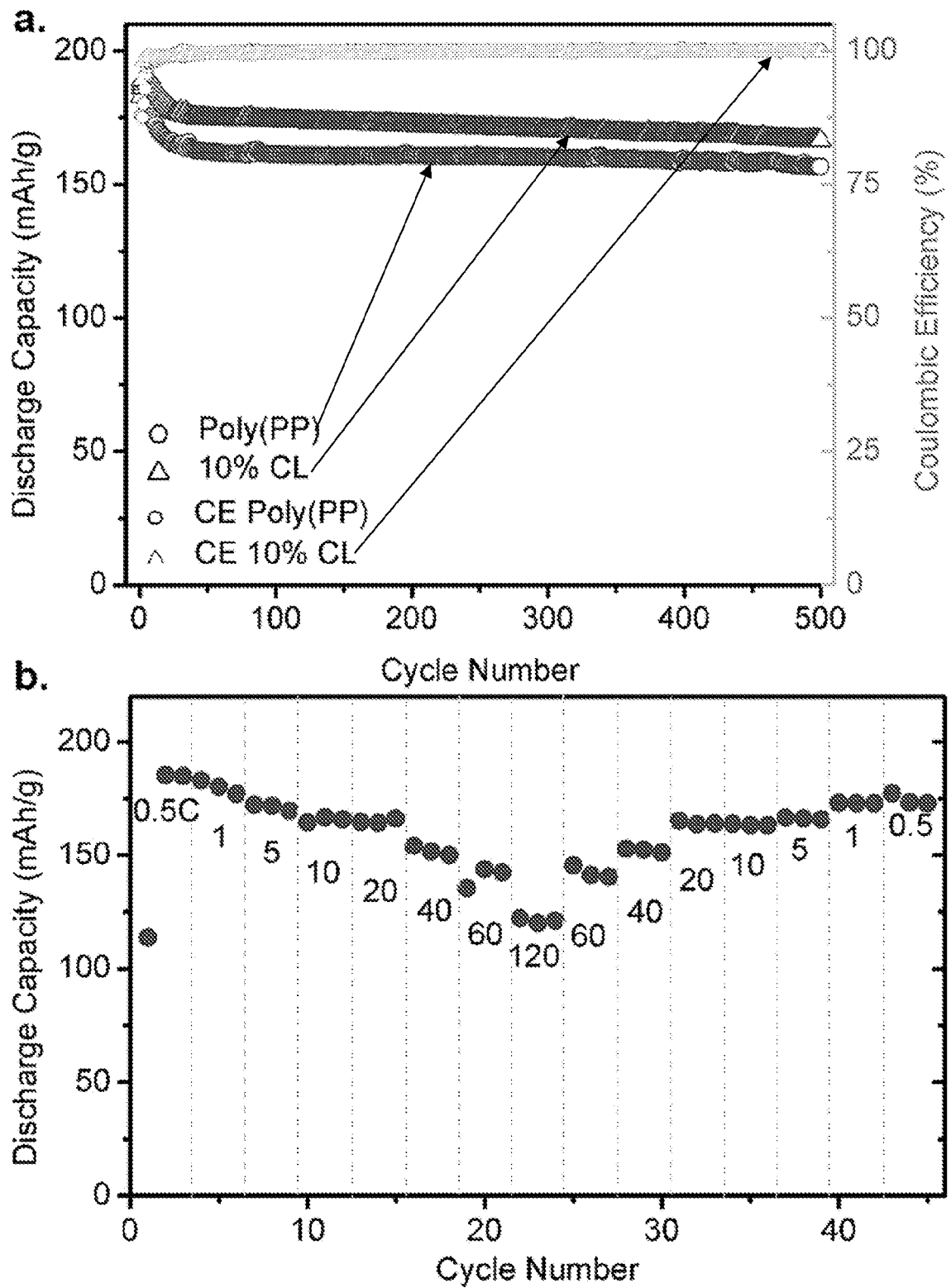
FIG. 8 shows (a.) cycling profiles of poly(Ph-PZ) and poly(Ph-PZ)-10 at 5 C for 500 cycles (b.) Rate performance of poly(Ph-PZ)-10 at different discharge C-rates.

Continued cycling of the poly(Ph-PZ) and poly(Ph-PZ)-10 at a demanding C-rate of 5, demonstrates the prolonged stability of each material (FIG. 8a). Each polymer exhibits a modest loss in discharge capacity over the first 25 cycles. Thereafter, both polymers exhibit 94% capacity retention. Notably, the poly(Ph-PZ)-10 retains 91% of its initial capacity and delivered 167 mAh $g^{-1}$ on the $500^{th}$ cycle.

The performance of poly(Ph-PZ)-10 under demanding discharge rates was analyzed. FIG. 8b plots its discharge capacity at various discharge rates. It is evident that the material excels under demanding loads, as it delivers 121 mAh $g^{-1}$ at 120 C, exhibiting facile charge transfer kinetics. Even after the material is subjected to these high discharge rates, when the discharge rate is reduced back to 0.5 C the material retains 93.5% of its initial capacity.

Figure 9:
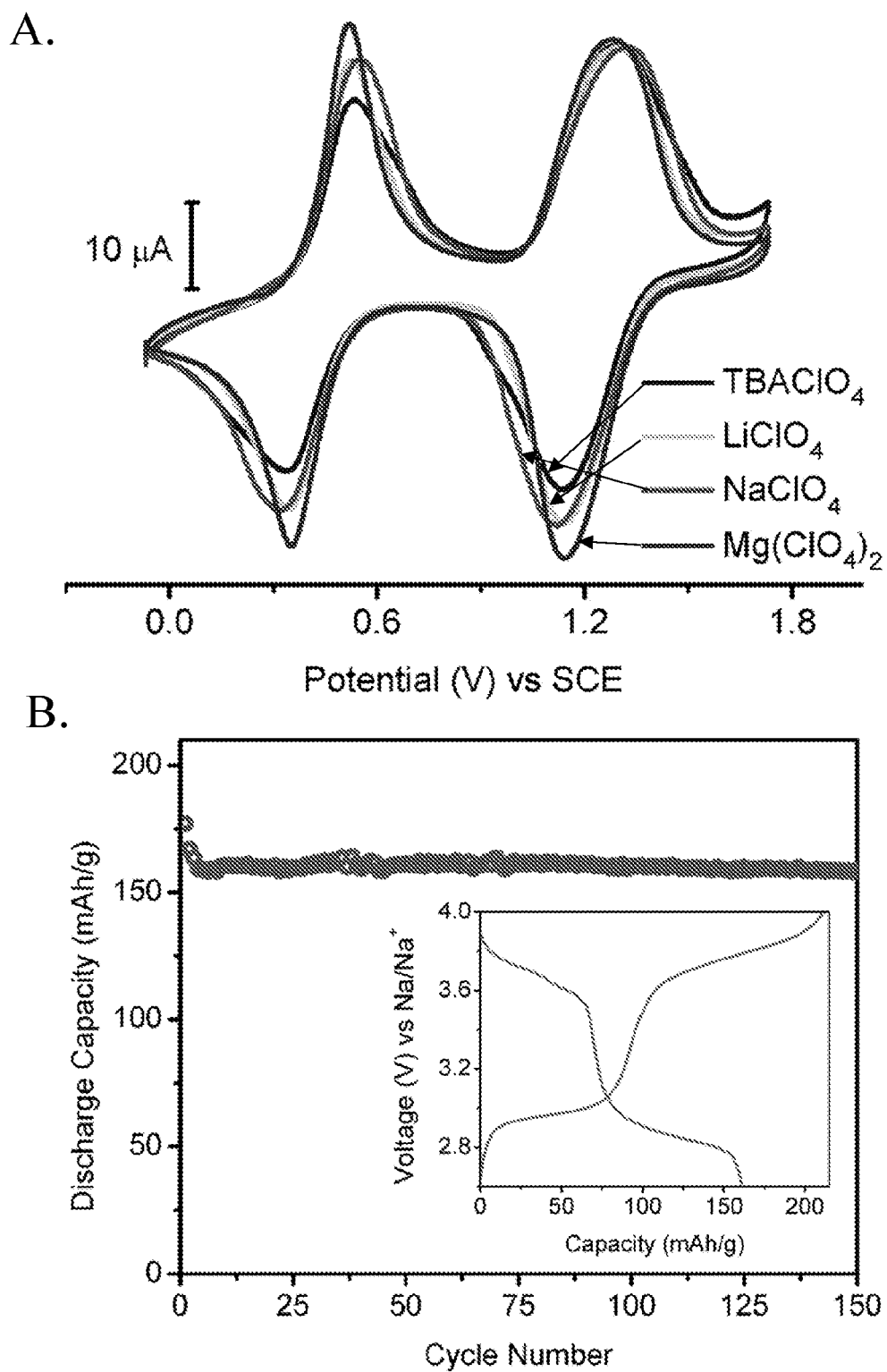
FIG. 9 shows (a.) poly(Ph-PZ)-10 in acetonitrile with various 0.1M perchlorate electrolyte salts. Scan rate 10 mV/s (b.) Cycling performance of poly(Ph-PZ)-10 in a sodium metal half-cell at 0.5 C.

Dual ion cathode materials lend themselves to use in alternative ion batteries. Since the anions are responsible for the charge compensation of poly(Ph-PZ) in its oxidized state, the material is unaffected by the use of different metal cations in solution. This means that this material can be used in a range of batteries such as sodium, magnesium, and potassium ion batteries without the performance of the cathode being affected. This effect is demonstrated by cycling poly(Ph-PZ)-10 in a variety of electrolyte salts, shown in the FIG. 9. The CV profiles remain essentially unchanged despite changing the cation in solution.

Figure 20:
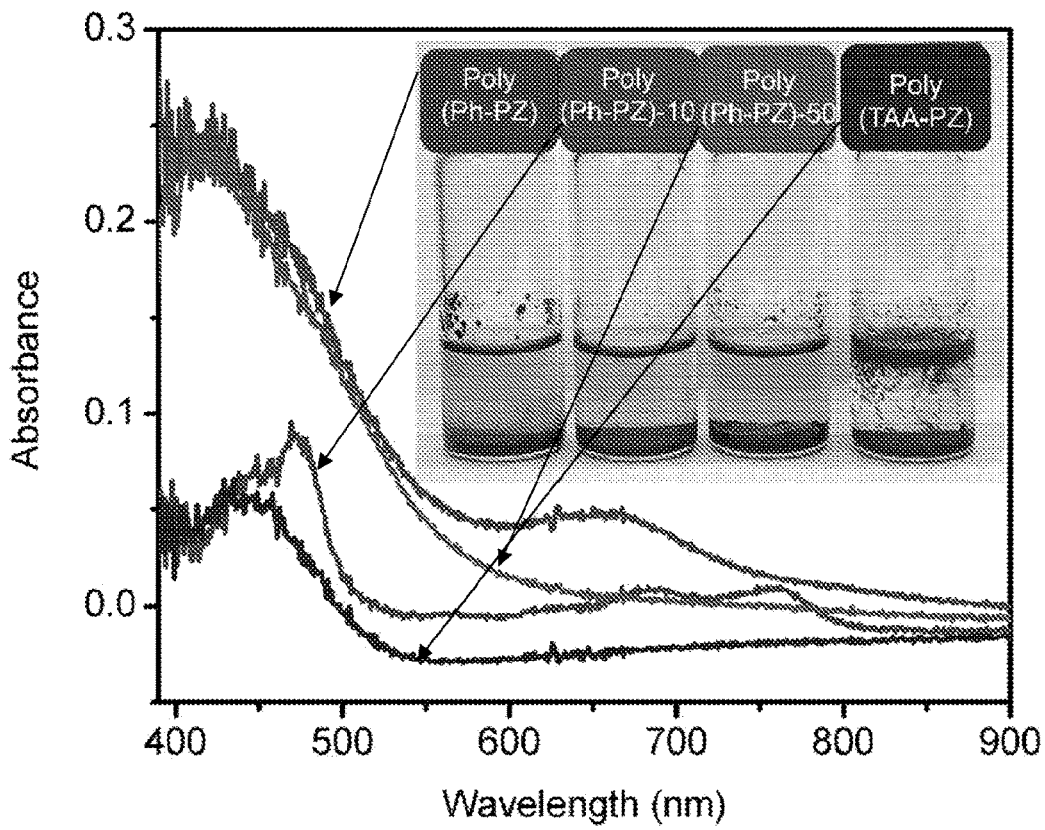
FIG. 20 shows absorbance spectra of polymer solutions. 1 M $LiPF_6$ in EC/DEC with poly(Ph-PZ), poly(Ph-PZ)-10, poly(Ph-PZ)-50, and poly(TAA-PZ) after 1 week. Inset shows pictures of solutions immediately before the absorbance spectra was taken.
Figure 21:
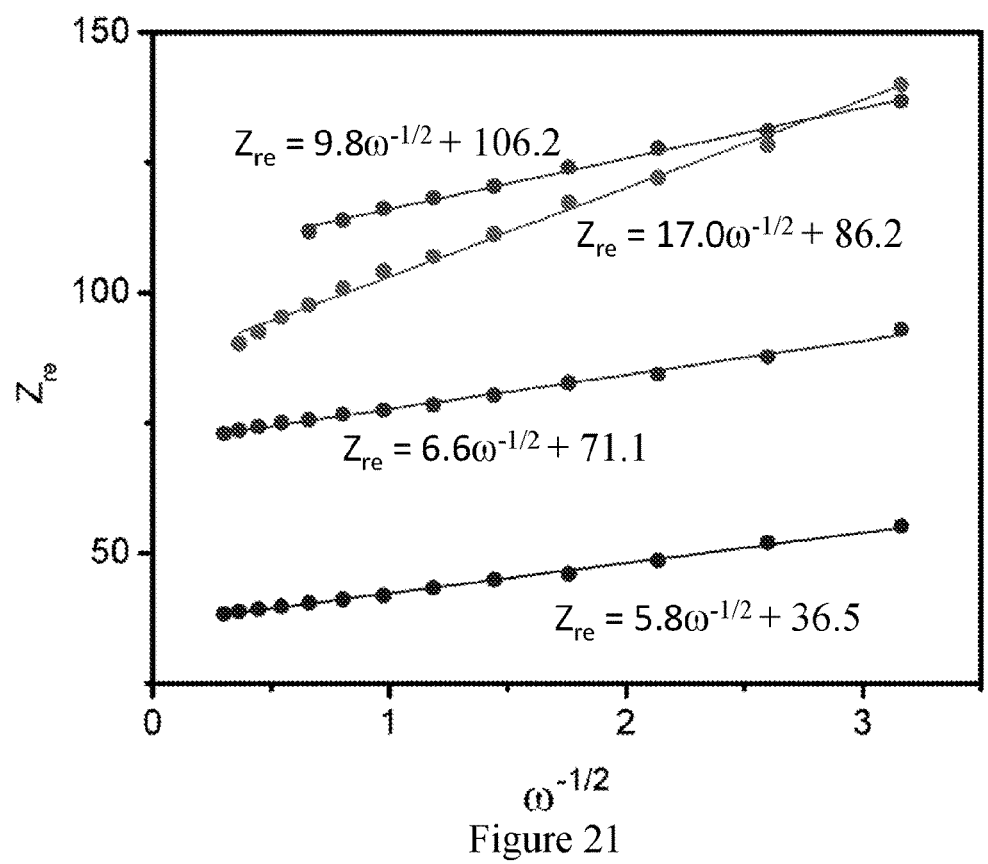
FIG. 21 shows linear fit of the low angular frequency data EIS for determination of the diffusion coefficient of $PF_6^-$ in each of the polymers at 2.8 V vs $Li/Li^+$.
Figure 22:
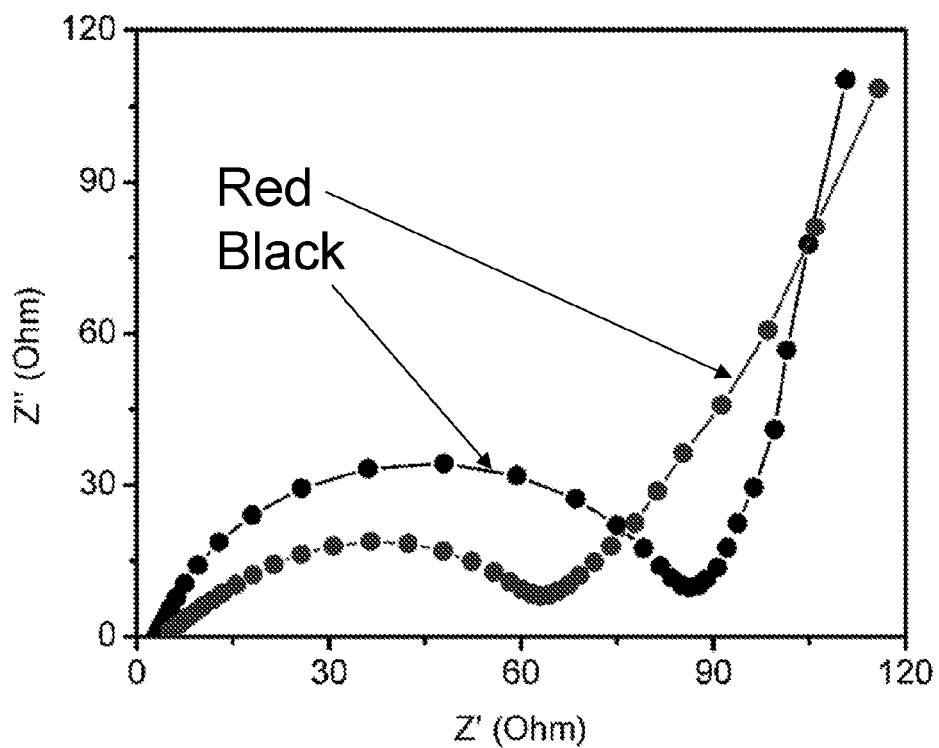
FIG. 22 shows PEIS spectra of poly(Ph-PZ)-10 coin cell before (black) and after (red) ten CV cycles, where the potential was swept from 2.7 V to 4.3 V vs $Li/Li^+$ at 1 mV/s. Each of the spectra was taken with the potential held at 2.7 V vs $Li/Li^+$.
Figure 23:
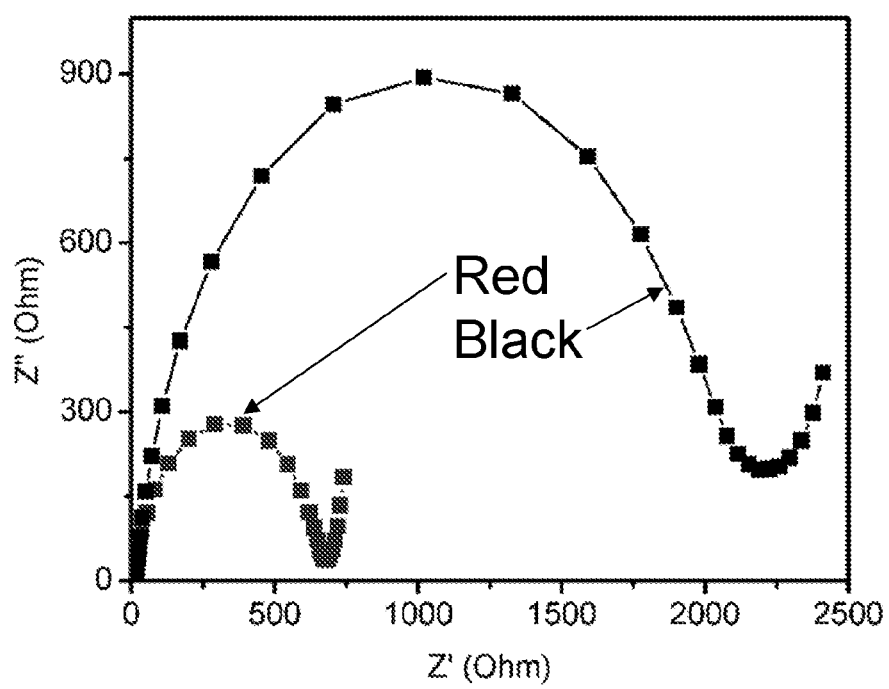
FIG. 23 shows PEIS spectra of poly(Ph-PZ)-10 in a sodium half-cell before (black) and after (red) eleven CV cycles, where the potential was swept from 2.5 V to 4.0 V vs $Na/Na^+$ at 1 mV/s. Each of the spectra was taken with the potential held at 2.5 V vs $Na/Na^+$.
Figure 24:
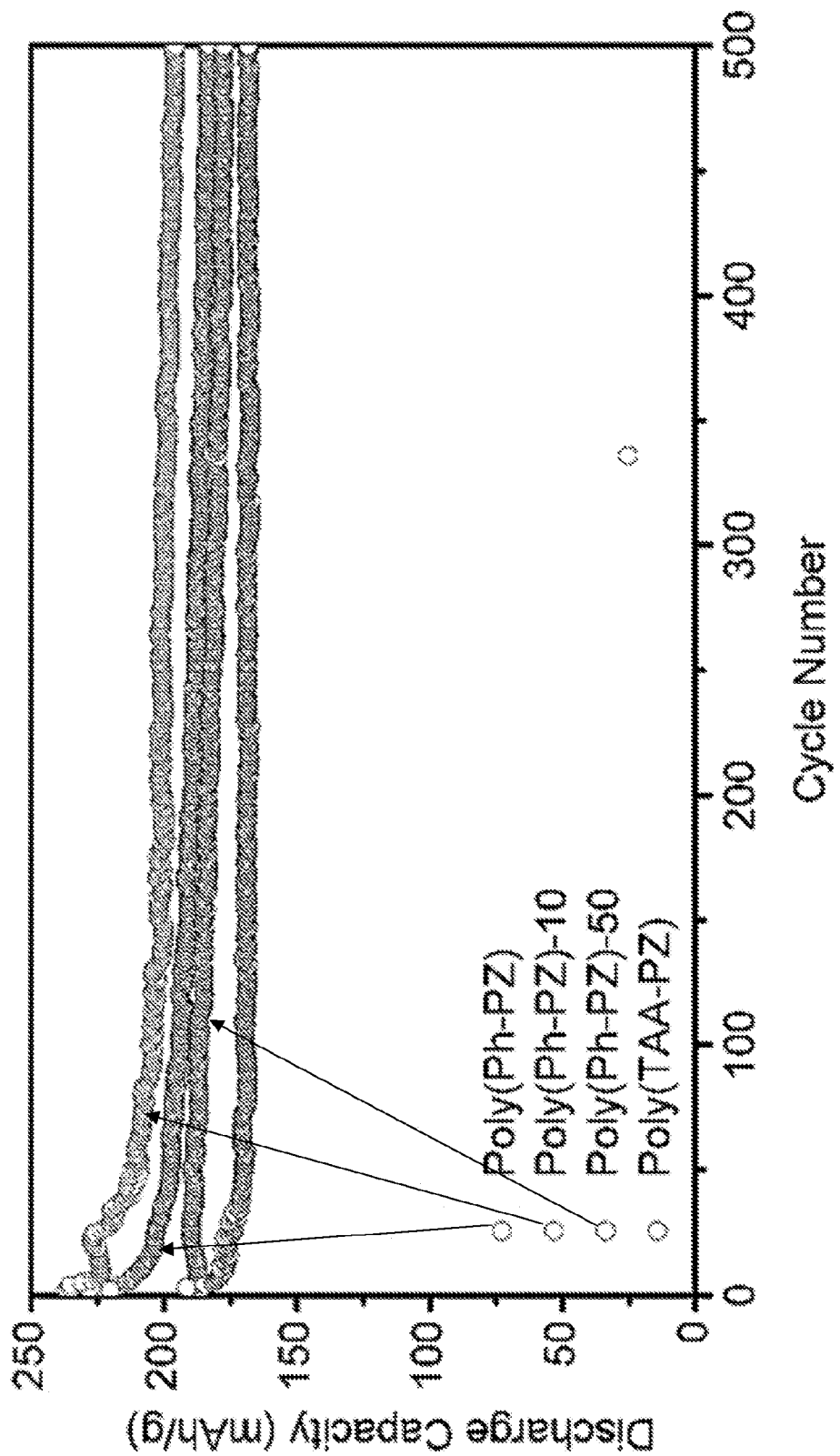
FIG. 24 shows cycle data for poly(Ph-PZ), poly(Ph-PZ)-10, poly(Ph-PZ)-50, and poly(TAA-PZ) coin cells. Cells were charged and discharged at 5 C between 1.5 V and 4.3 V vs $Li/Li^+$.
Figure 25:
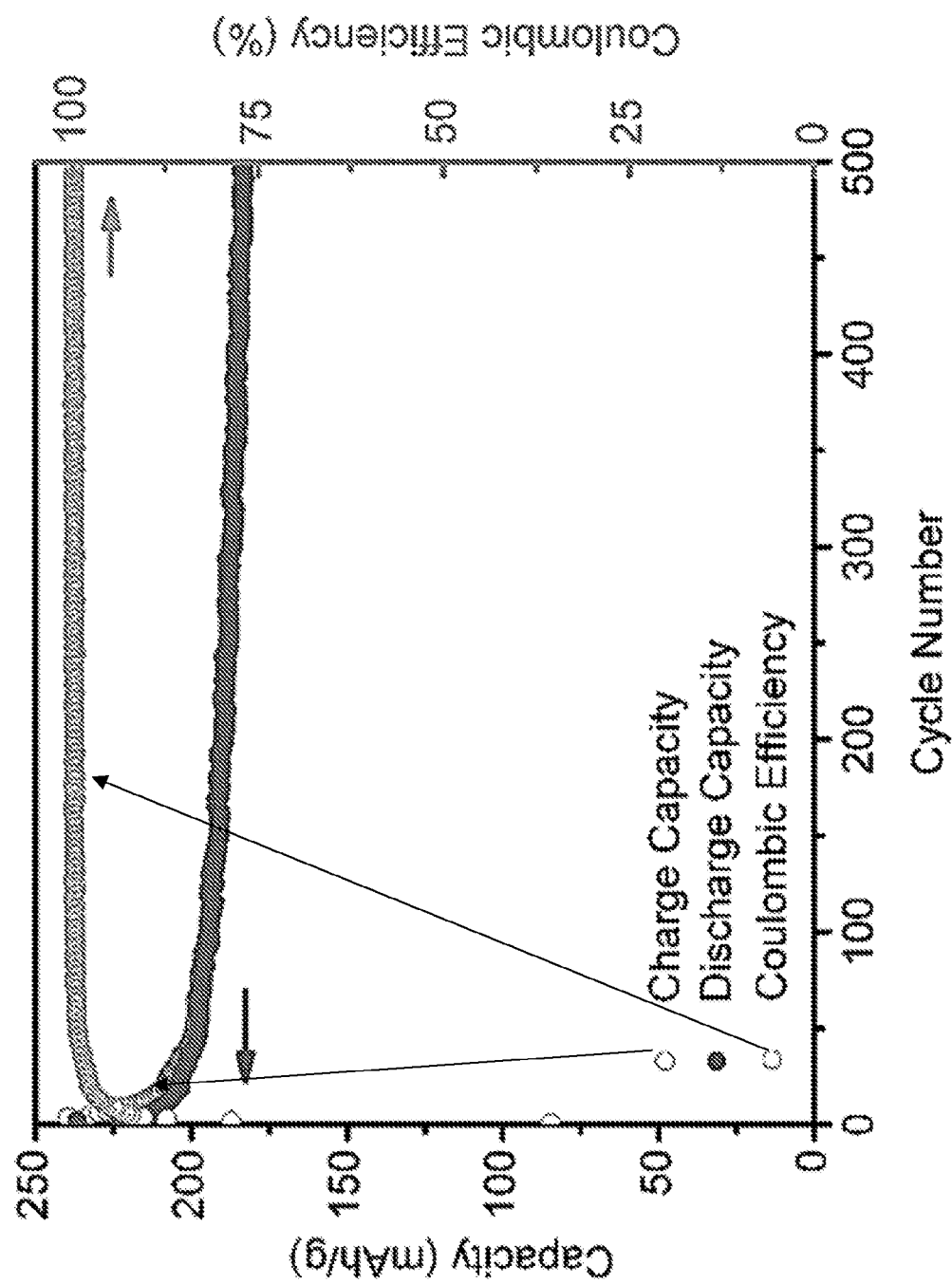
FIG. 25 shows poly(Ph-PZ) coin cell, presented in FIG. 24, with corresponding charge capacities and coulombic efficiencies. This cell is representative of the cells' performance in FIG. 25, in terms of the high, stable coulombic efficiency achieved in each of the cells. Coulombic efficiencies as high as 99.9% have been observed.
Figure 26:
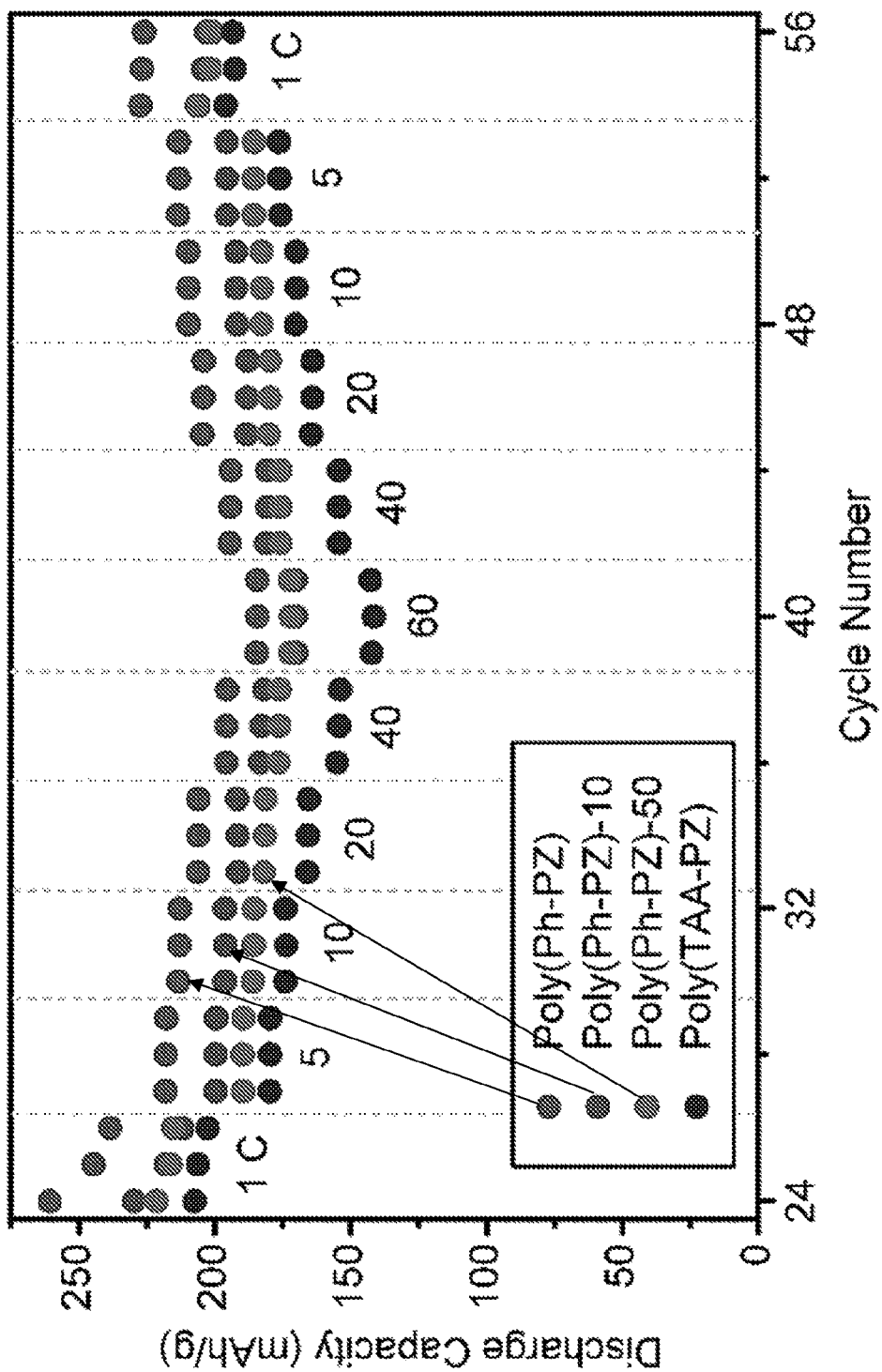
FIG. 26 shows rate performance of poly(Ph-PZ), poly(Ph-PZ)-10, poly(Ph-PZ)-50, and poly(TAA-PZ) coin cells. In these cells, a fiber glass A separator has been used instead of a celgard separator, used in the previous cells. Cells were charged to 4.3 V vs. $Li/Li^+$ at 5 C (except the data labelled 1 C, which was charged and discharged at 1 C), and discharged at the rate marked on the graph above to 1.5 V vs. $Li/Li^+$.
Figure 27:
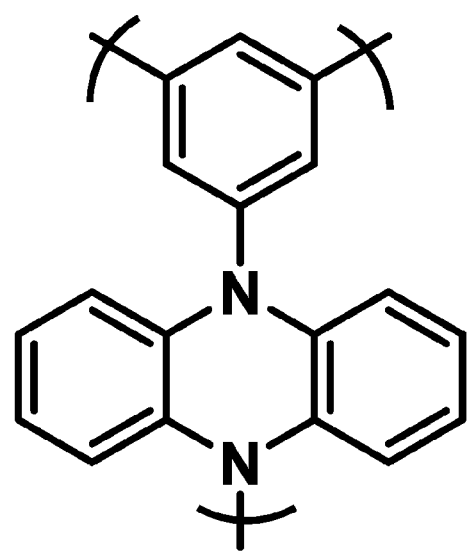
FIG. 27 shows the structure of poly(triphenyl-phenazine) (poly(TPh-PZ)). By having three branches off of the phenyl group cross-linker, the theoretical capacity of the polymer increases to 232 mAh/g.
Figure 28:
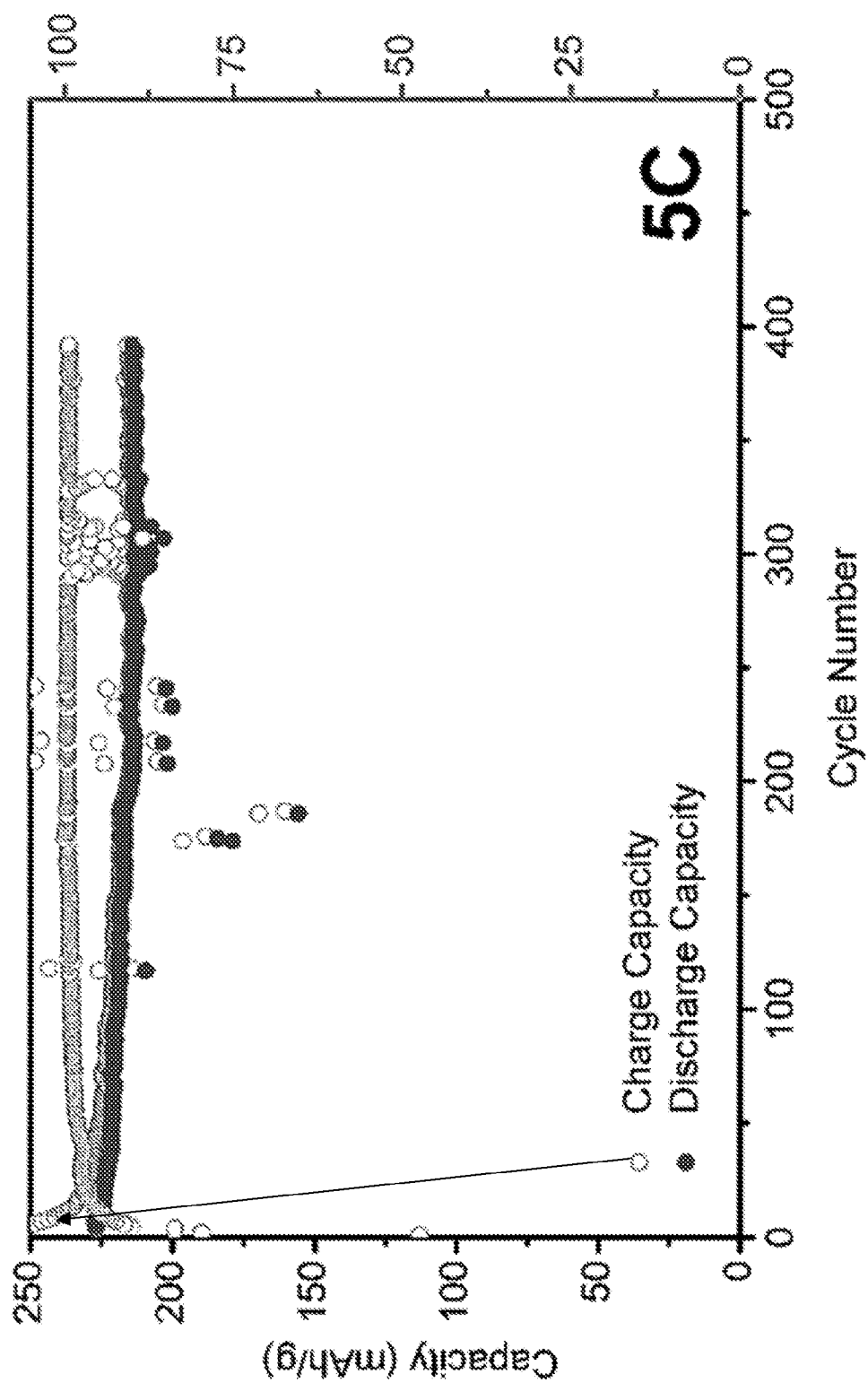
FIG. 28 shows cycling performance of poly(TPh-PZ) in a coin cell, charged and discharged at 5 C. The second redox couple for poly(TPh-PZ) is shifted to a slightly higher potential, so these cells are cycled between 1.5 V and 4.4 V vs. $Li/Li^+$. The noise in the cycling data is caused by problems in discharge cycles, which is then followed by a low capacity in the following charge cycle. The cause is not yet known. We hypothesize it may be some minor instabilities in the cell due to the higher charging voltage used, and plan to address this issue by purifying the solvent in the battery/changing to a different coin cell casing designed to tolerate higher charge potentials.
Figure 29:
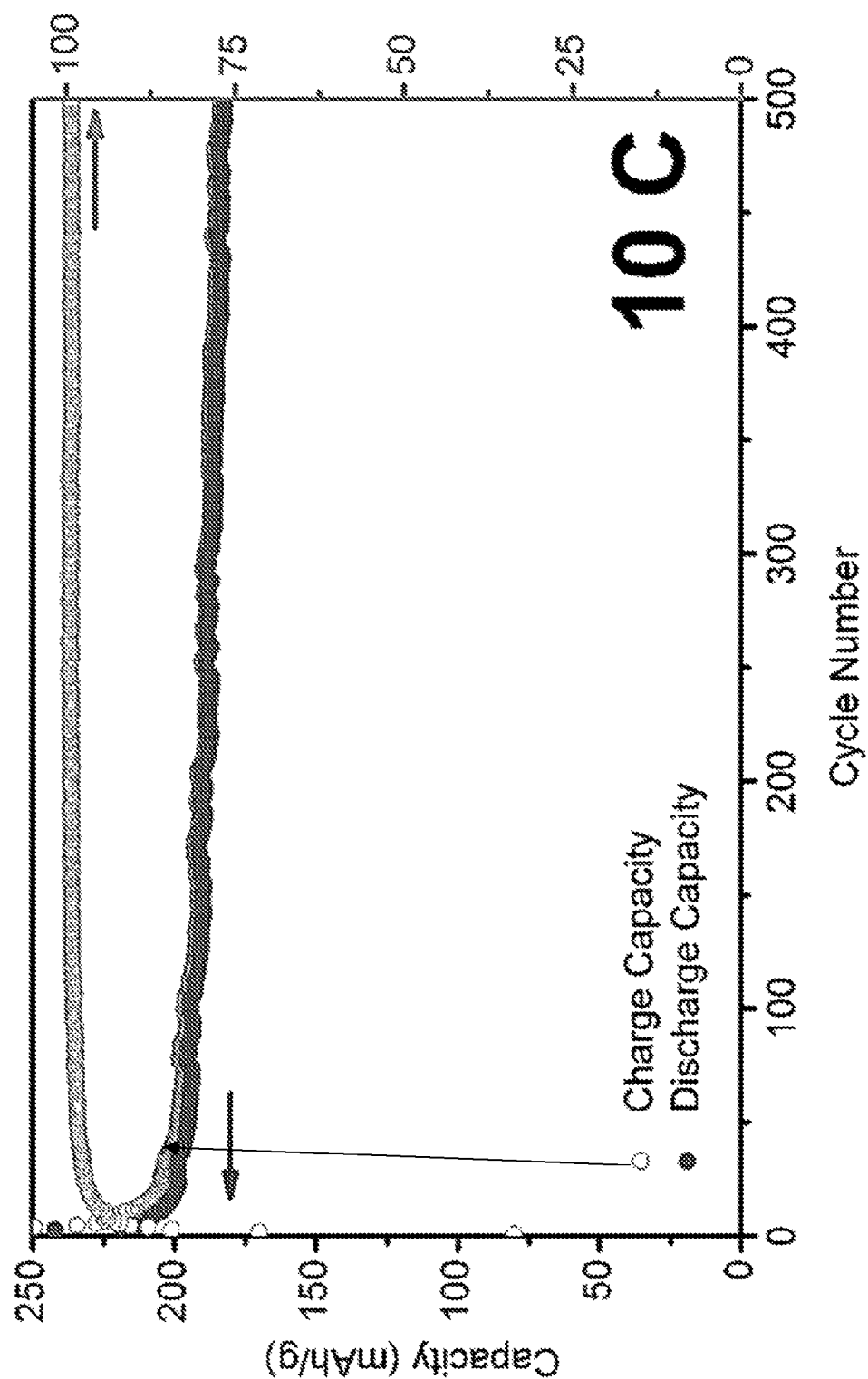
FIG. 29 shows cycling data from poly(TPh-PZ) coin cell at 10 C between 1.5 V and 4.4 V vs. $Li/Li^+$. We want to highlight the high coulombic efficiency, even at a high charge/discharge rate. Capacity drops slightly from the capacity obtained at 5 C, as would be expected, however the stability in the cell's capacity is well maintained. We note that the noise from the above plot at 5 C is not seen at the higher charge/discharge rate, leading us to believe that the noise above is not a problem with the active material itself.
Figure 30:
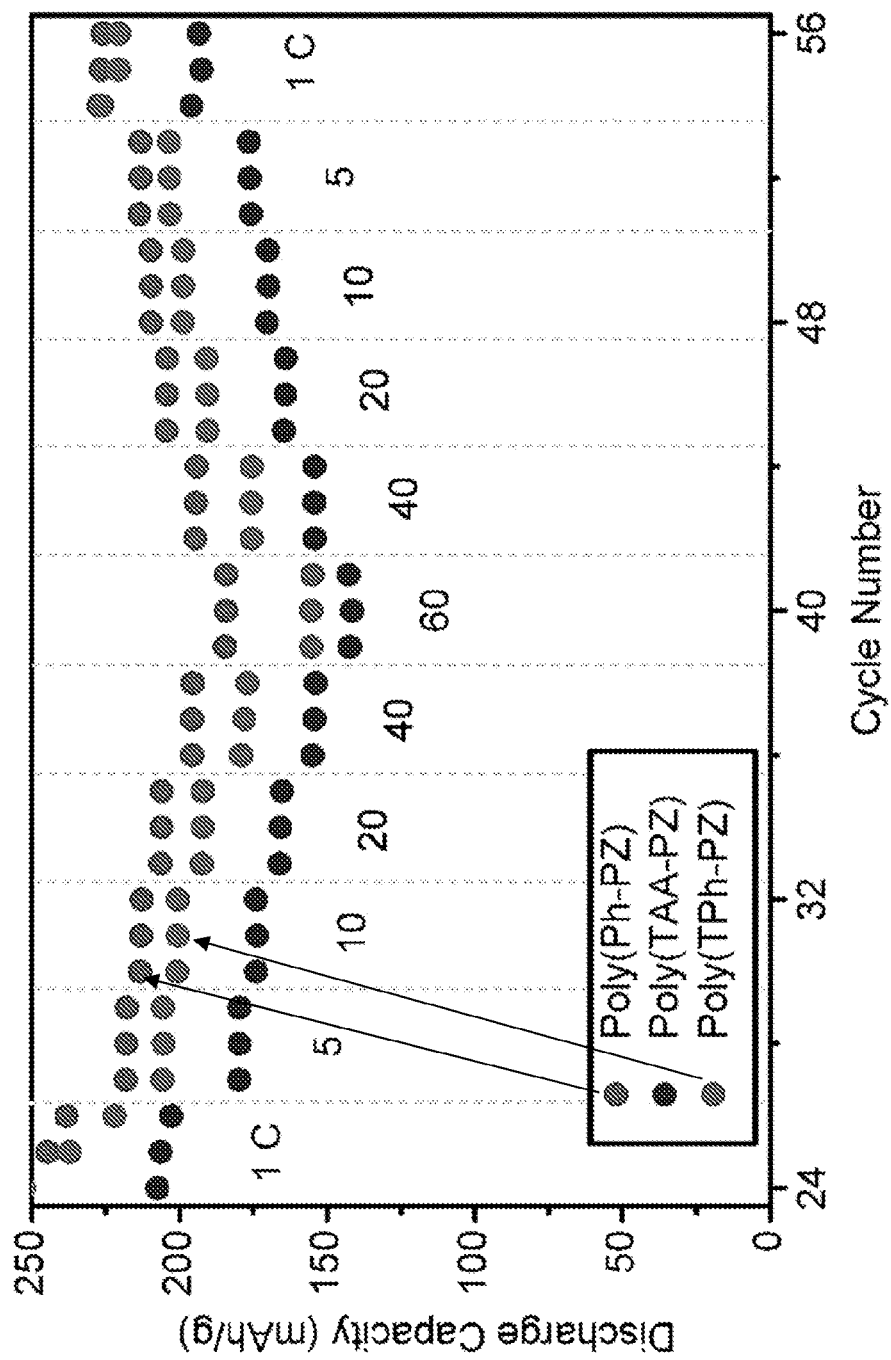
FIG. 30 shows rate performance data of poly(Ph-PZ) (blue), poly(TAA-PZ) (purple), and poly(TPh-PZ) coin cells, charged at 5 C and discharged at the rates noted above (again with the exception of the data at 1 C, which was also charged at 1 C). We highlight the improved rate performance of the linear poly(Ph-PZ) over the two cross-linked polymers, in terms of the polymer's ability to maintain its capacity at high C-rates.

With these results, poly(Ph-PZ)-10 was employed in a sodium battery. Coin cells were assembled with a sodium metal anode and poly(Ph-PZ)-10 as the cathode in 1 M $NaPF_6$ EC/DEC electrolyte. Due to a large resistance in the sodium cell, it was tested at a low C-rate. Cycling the cell at 0.5 C provided a steady discharge capacity of over 160 mAh $g^{-1}$ even after 100 cycles, comparable to the capacity obtained in a lithium cell. The large charging capacity in the first cycle and the poor coulombic efficiency are attributed to the incompatibility of carbonate-based electrolytes with sodium salts, leading to an increased resistance in the cell, as observed by impedance spectroscopy (FIG. 20). To obtain the same results achieved in the lithium cell, each of the components of the sodium coin cell would require further optimization. Still, these results are encouraging for poly(Ph-PZ)-10's ability to function in alternative ion batteries.

The performance metrics of these poly(Ph-PZ) based materials as cathodes are among the highest reported. Through arylation of the phenazine groups, the redox couples become electrochemically more reversible at significantly more positive potentials, thus creating a cathode building block with high voltage and C-rate capabilities. The branched polymer structure, poly(Ph-PZ)-10, attained by copolymerization with tris(4-bromophenyl)amine lead to a decrease in solubility while retaining excellent charge transport kinetics. As a cathode material, poly(Ph-PZ)-10 delivers 198 mAh g$^{-1}$ at 0.5 C and 121 mAh g$^{-1}$ at 120 C at an average operating voltage of 3.45 V vs Li/Li$^+$. These values translate to an energy density of 676 Wh kg$^{-1}$ and a power density of 50 kW kg$^{-1}$, respectively, when assimilated in a cell with a lithium foil anode and normalized to the amount of active material.

To further show the materials potential in a device, cells of higher active mass loading were made. At 120 C, a cell with 6:3:1 poly(Ph-PZ)-10: conductive carbon:PVDF was able to deliver a capacity of 89.5 mAh g$^{-1}$ (FIG. 20), corresponding to a power density of 21.9 kW kg$^{-1}$ when normalized to the mass of the entire cathode composite, a power density over six times that of a commercial LiNMC cathode (Table 5). This material offers an energy density competitive with current commercial lithium ion batteries, a power density comparable to commercial supercapacitors, and demonstrates the viability of organic cathodes in EES devices.

Experimental Information.

General Reagent Information. Isobutyl vinyl ether (IBVE) (99%, TCI), ethyl vinyl ether (EVE) (99%, Sigma Aldrich), 2-chloroethyl vinyl ether (Cl-EVE) (97%, TCI), n-propyl vinyl ether (nPrVE) (99%, Sigma Aldrich), and n-butyl vinyl ether (nBuVE) (98%, Sigma Aldrich), cyclohexyl vinyl ether (CyVE) (98%, Sigma Aldrich) and methacrylate (MA) (>99%, TCI) were dried over calcium hydride (CaH$_2$) (ACROS organics, 93% extra pure, 0-2 mm grain size) for 12 hours, distilled under nitrogen, and degassed by three freeze-pump-thaw cycles. 4-methoxystyrene (97%, Sigma Aldrich) was dried over CaH$_2$ for 12 hours, distilled under vacuum, and degassed by three freeze-pump-thaw cycles. Tetrabutylammonium tetrafluoroborate (TBA) (98%, TCI) was recrystallized from ethyl acetate/hexanes and dried under reduced pressure at 60° C. for 12 hours. Tetrabutylammonium hexafluorophosphate (98%, TCI) was recrystallized three times from anhydrous ethanol and dried under reduced pressure at 60° C. for 12 hours. Tetrabutylammonium Perchlorate (TBAP) (98%, TCI) was purified by recrystallization from ethyl acetate three times and dried under reduced pressure at 60° C. for 12 hours. Dichloromethane (DCM), and diethylether (Et$_2$O) were purchased from J. T. Baker and were purified by vigorous purging with argon for 2 hours, followed by passing through two packed columns of neutral alumina under argon pressure. Acetonitrile (MeCN) (HPLC Grade) was purchased from Fisher Chemical and dried over an activated 4 Å molecular sieve (Mallinckrodt Chemicals) for at least two days before use. Hexanes and ethyl acetate were purchased from Fischer Scientific and used as received. Ethanol (anhydrous, 200 proof) was purchased from Koptec. 1-Methyl-2-pyrrolidinone (NMP) (anhydrous 99.5%) was purchased from Sigma-Aldrich and used as received. Alumina (1.0, 0.3, 0.05 μm pore size) was purchased from Extec. S-1-isobutoxyethyl N,N-diethyl dithiocarbamate (1a)[1] and S-1-isobutoxylethyl S'-ethyl trithiocarbonate (1b) were synthesized according to literature procedures. Reticulated vitreous carbon was purchased from ERG Aerospace. Microcloth PSA (polishing paper) and Abrasive Paper (600 grit) were purchased from Buehler. Ordered mesoporous carbon CMK-3 was purchased from ACS materials and used as received. Super P carbon (Imerys Graphite& Carbon) and poly(vinylidene fluoride) (PVDF) (Kynar Flex) were dried overnight in a vacuum oven at 60° C. and stored in a desiccator.

General Analytical Information. All polymer samples were analyzed using a Tosoh EcoSec HLC 8320GPC system with two SuperHM-M columns in series at a flow rate of 0.350 mL/min. THE was used as the eluent and all number-average molecular weights ($M_n$), weight-average molecular weights ($M_w$), and dispersities (Đ) were determined by light scattering using a Wyatt miniDawn Treos multi-angle light scattering detector. Nuclear magnetic resonance (NMR) spectra were recorded on a Varian 400 MHz, a Varian 600 MHz, or a Bruker 500 MHz instrument. Electrolysis experiments were performed using a BASi EC Epsilon potentiostat or a DC power supply. General electrode construction and dimensions can be found in previous literature.

Cyclic Voltammetry Procedure. Benchtop cyclic voltammetry experiments were performed in a three-compartment glass cell with medium porosity glass frits separating the compartments. A homemade Ag/Ag$^+$ reference electrode and a Pt wire counter electrode were used, unless otherwise specified. All potentials are referenced to Fc$^+$/Fc, which was acquired after all measurements (0.540 V vs Ag/Ag$^+$) reference electrode. All 3-mm glassy carbon (GC) electrodes were purchased from CH Instruments. Prior to the experiment, electrodes were polished using diamond paste and MetaDi Fluid (Buehler). All cyclic voltammetry measurements were done in 0.1M TBAP in MeCN unless otherwise specified. The potentials in the CVs was corrected for iR drop using a ferrocene reference at different scan rates.

Device Testing. Device measurements were conducted in CR 2032 coin cell casings which were assembled in an argon filled glove box. The anode was lithium metal (Alfa Asear) and the working electrode was fabricated from a slurry of 30 wt % active material (~0.6 mg/cm$^2$), 30 wt % Super P carbon, 30 wt % CMK-3, and 10 wt % PVDF as the binder in NMP. The high loading cathode was fabricated with 60 wt % active material, 15 wt % Super P carbon, 15 wt % CMK-3, and 10 wt % poly(vinylidene fluoride) (PVDF) as binder. The slurries were spread onto a carbon paper current collector using the doctor's blade method with one layer of scotch tape. The coated electrode was dried for 2 h at 60° C. followed by 14 h at 110° C. in a vacuum oven. A polypropylene separator (Celgard 2300) was used as the separator between the two electrodes. The electrolyte solution was 1:1 ratio by volume of EC (ethylene carbonate) to DEC (diethyl carbonate) with 1M LiPF$_6$ (Aldrich). An Arbin BT2000 battery tester was used to perform Galvanostatic charge/discharge experiments on the coin cells with a constant charge-discharge current rate of 5 C over a voltage range of 2.8 to 4.3 V vs. Li/Li$^+$ at 25° C. in order to evaluate the cycling performance. For rate experiments, the lower voltage bound was decreased to accommodate the lower voltage plateau at higher discharge rates to a minimum value of 2.3 V at 120 C. For rate measurements, the coin cell was charged at 5 C and discharged at the labeled C-rate.

The theoretical capacities of poly(phenyl-phenazine), poly(phenyl-phenazine) 10% CL, poly(phenyl-phenazine) 50% CL, and poly(triarylamine-phenazine) where calculated using Eq. (1):

$$C_{theor} = \frac{nF}{3600\left(\frac{M_W}{1000}\right)} \quad (1)$$

Where n is the number of electrons that can be stored per a redox active unit, F is Faraday's constant (96485 C mol$^{-1}$), and M$_w$ is the molecular weight of the redox active unit.

Electrochemical Impedance Spectroscopy (EIS).

Electrochemical impedance spectroscopy measurements were carried out using a BioLogic SP-150 potentiostat on lithium metal coin cells. Impedance measurements were obtained at 2.80 V vs Li/Li$^+$ after the cells had been allowed to sit fully assembled for at least 24 hours and the cell was held at 2.8V for 300 s prior to measurement. The measurements were taken over a frequency range of 0.001-200000 Hz with an AC amplitude of 10.0 mV.

TABLE 3

Diffusion coefficients obtained from the limiting current at an ultra-microelectrode and ratio of peak anodic current/peak cathodic current for phenazine small molecules at 50 mV/s.

| Small Molecule | $D_{0\rightarrow\pm1}$ (cm$^2$/s) | $D_{\pm1\rightarrow\pm2}$ (cm$^2$/s) | $i_{pk,a}/i_{pk,c}$ (0→±1) | $i_{pk,a}/i_{pk,c}$ (±1→±2) |
|---|---|---|---|---|
| Phenazine | 6.3 × 10$^{-6}$ | 6.4 × 10$^{-6}$ | 1.01 | 0.54 |
| Phenazine +50 mM TFA | 1.1 × 10$^{-5}$ | 1.2 × 10$^{-5}$ | 1.14 | 0.80 |
| Dimethyl Phenazine | 7.1 × 10$^{-6}$ | 6.7 × 10$^{-6}$ | 0.98 | 1.02 |
| Diphenyl Phenazine | 8.0 × 10$^{-6}$ | 7.1 × 10$^{-6}$ | 0.99 | 0.89 |

A Nyquist plot for each of the polymers was made to compare the charge transfer kinetics and electric responses based on the size of the semicircle at high and middle frequencies. The low frequency data was used to obtain the PF$_6^-$ diffusion coefficients according to Eq. (2)[3,4]:

$$D = 0.5\left(\frac{RT}{AF^2\sigma C}\right)^2 \quad (2)$$

In which R is the gas constant (8.314 J mol$^{-1}$ K$^{-1}$), T is the temperature in K (298 K), A is the area of the electrode surface (1.33 cm$^2$), F is Faraday's constant (96485 C mol$^{-1}$), σ is the Warburg coefficient, and C is the molar concentration of PF$_6^-$ (1 M). The Warburg coefficient, σ, can be determined from the slope of Z$_{re}$ vs. the reciprocal square root of the low angular frequencies (ω$^{-1/2}$) based on Eq. (3):

$$Z_{re} = R_e + R_{ct} + \sigma\omega^{-1/2} \quad (3)$$

Figure 12:
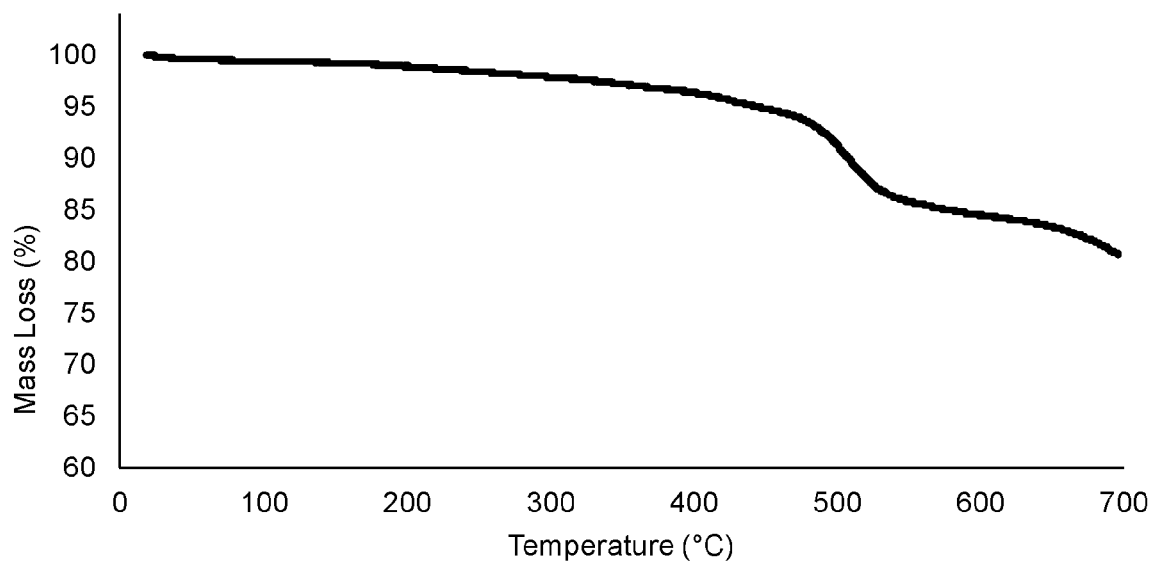
FIG. 12 shows thermogravimetric Analysis (TGA) of poly(Ph-PZ)-10.
Figure 13:
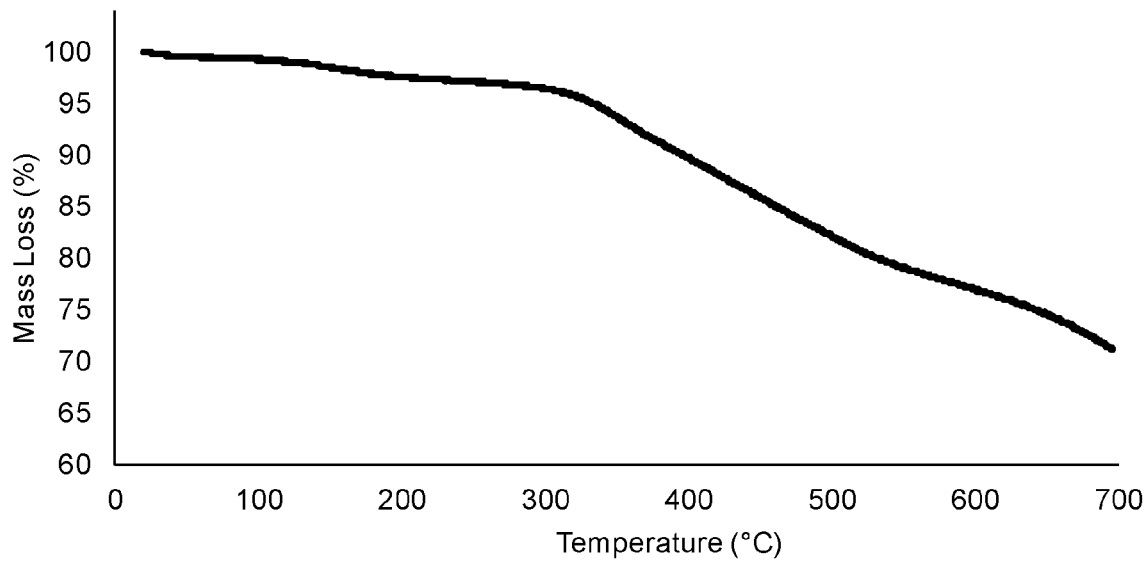
FIG. 13 shows thermogravimetric Analysis (TGA) of poly(Ph-PZ)-50.
Figure 14:
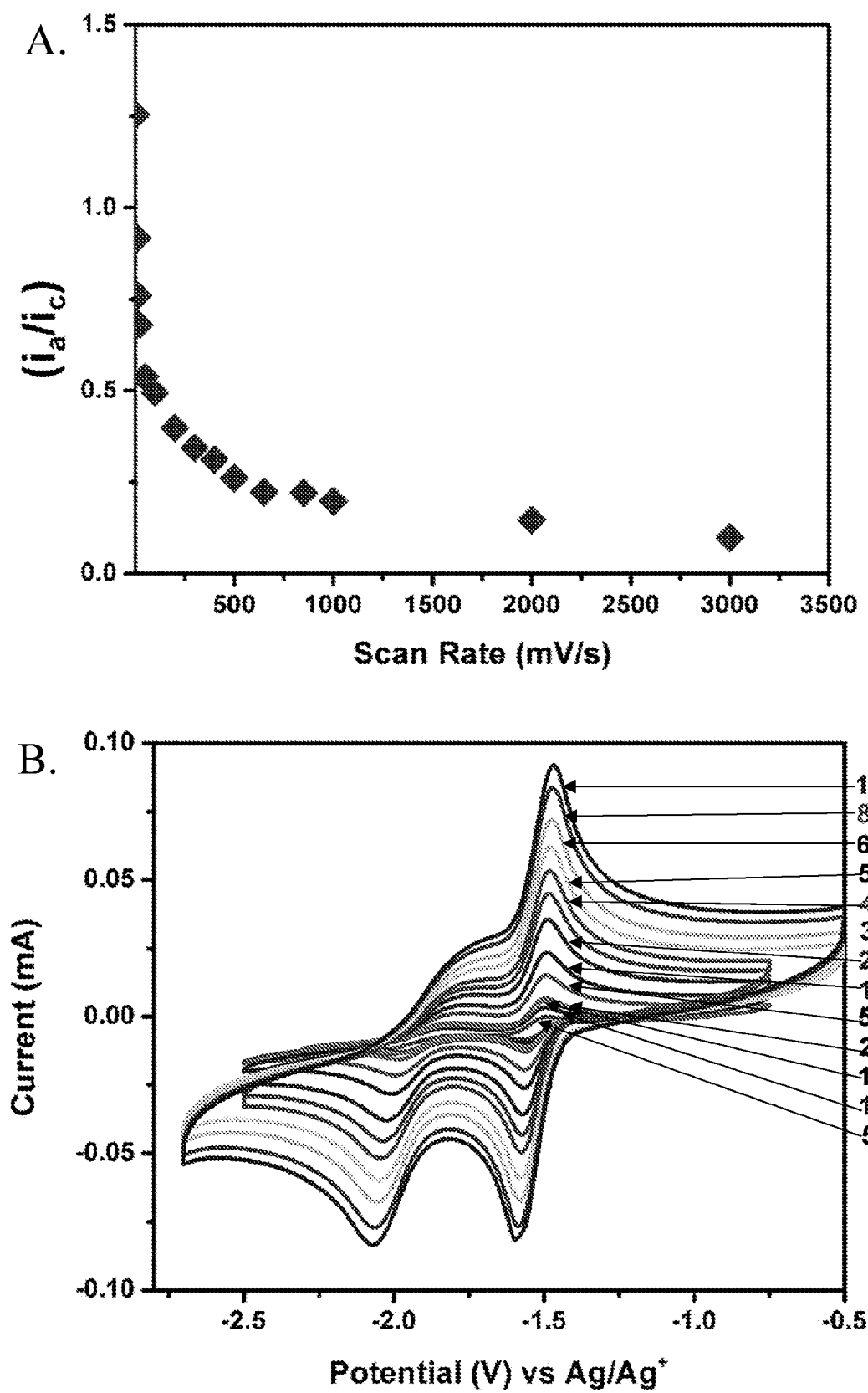
FIG. 14 shows $i_a/i_c$ of small molecules at varying scan rates. (a) 1 mM phenazine in 0.1 M TBAP in acetonitrile at various scan rates (b) plot of peak anodic current/peak cathodic current of the second redox couple ($E_{1/2}=-1.92$ V) versus scan rate. Decreasing $i_a/i_c$ with increasing scan rates chemical irreversibility.
Figure 15:
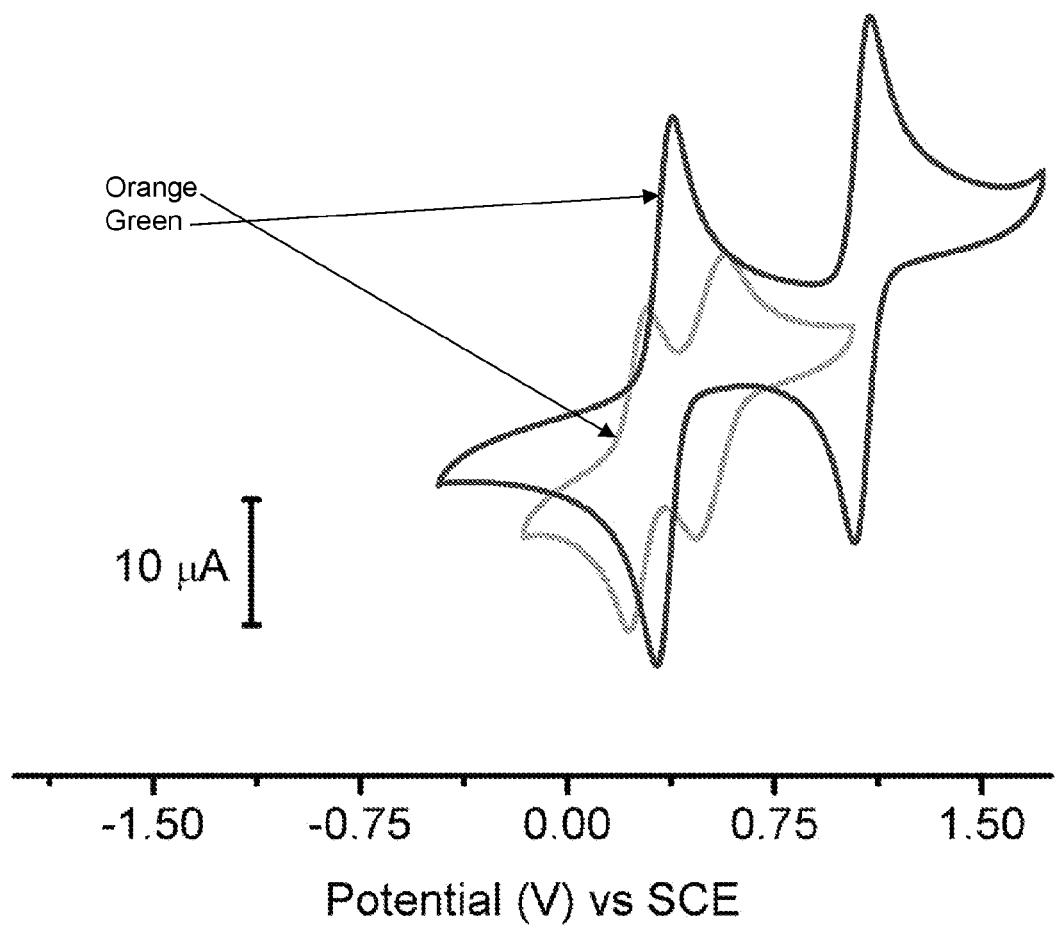
FIG. 15 shows CV traces of small molecules. 1 mM phenazine in 0.1 M TBAP in MeCN at a glassy carbon electrode with addition of 50 mM TFA to electrolyte solution (orange) and 1 mM N,N'-dimethyl-phenazine (green) at 50 mV/s.

These plots are shown in FIG. 12 and the obtained diffusion coefficients can be found in Table 3.

Slurry Preparation. Slurries were prepared for the comparison of poly(phenyl-phenazine) 10% CL in 0.1M perchlorate solutions in acetonitrile with different cations present. The slurry consisted of 1.5 mg of poly(phenyl-phenazine) 10% CL, 3 mg of Super P carbon, and 0.5 mg of PVDF dissolved in 1 mL of NMP. The mixture was sonicated until the particulates were homogeneously dispersed, about one hour. Two μL of the slurry were drop-cast on a polished glassy carbon electrode for a polymer loading of 0.042 mg/cm$^2$.

Ultramicroelectrode Studies. Phenazine, N,N'-dimethyl-phenazine, and N,N'-diphenyl-phenazine were each dissolved at a 1 mM concentration in solutions with 0.1 M TBAP supporting electrolyte in acetonitrile. To one of the phenazine solutions, 50 mM TFA was added. A 10 μm platinum electrode was used as the working electrode in a three-compartment cell with a platinum wire as the counter electrode and a Ag/Ag$^+$ reference electrode. Cyclic voltammograms were obtained at 20 mV/s and used to obtain a steady state response for the redox events for each of the small molecules due to convergent flux.

The limiting current at steady state following each redox event was used to calculate the diffusion coefficient, D, by Eq. (4):

$$D = \frac{i_L}{2\pi FdC} \quad (4)$$

Where i$_L$ is the limiting current, d is the diameter of the electrode, and C is the concentration of the analyte (1 mM), and F has the same definition as above. To determine the standard heterogeneous rate constant, k$_s$, Eq (5)[2] was employed:

$$(4D_R/\pi k_s r_0)\exp[-(1-\alpha)nf(E-E^{0'})] = \frac{i_L - i}{i} - \frac{D_R}{D_O}\exp[-nf(E-E^{0'})] \quad (5)$$

By assume the D$_o$=D$_R$=D, the equation can be simplified to Eq. (6) for reductions and Eq. (7) for oxidations:

$$\ln\left(\frac{i_L - i}{i}\right) = \alpha nf\left(E - E^{\frac{1}{2}}\right) + \ln\left(\frac{4D}{\pi k_s r_0}\right) \quad (6)$$

$$\ln\left(\frac{i_L - i}{i}\right) = (1-\alpha)nf\left(E - E^{\frac{1}{2}}\right) + \ln\left(\frac{4D}{\pi k_s r_0}\right) \quad (7)$$

where i is the current at a given potential, α is the transfer coefficient, n is the number of electrons transferred, E is the potential, E$^{1/2}$ is the potential at half the limiting current, and r$_0$ is the radius of the electrode (10 μm). A plot of $$\ln\left(\frac{i_L - i}{i}\right) \text{ vs } E - E^{1/2}$$

will give an intercept of $$\ln\left(\frac{4D}{\pi k_s r_0}\right)$$

from which the rate constant was calculated. The calculated D and k$_s$ values are found in Table 3.

TABLE 4

Fitted values from electrochemical impedance spectroscopy at 2.7 V vs. Li/Li$^+$.

| Active Material | R1 (Ω) | CPE(F·s$^{(a-1)}$) × 10$^{-6}$ | a | R$_2$ (Ω) |
|---|---|---|---|---|
| poly(Ph-PZ) | 4.07 ± 0.39 | 45.65 ± 11.86 | 0.76 ± 0.55 | 54.00 ± 0.04 |
| poly(Ph-PZ)-10 | 3.36 ± 0.37 | 25.01 ± 6.01 | 0.80 ± 0.55 | 57.27 ± 0.66 |
| poly(Ph-PZ)-50 | 2.95 ± 0.36 | 59.34 ± 15.30 | 0.78 ± 0.55 | 49.12 ± 0.48 |
| poly(TAA-PZ) | 7.95 ± 0.28 | 21.77 ± 02.36 | 0.79 ± 0.52 | 100.70 ± 0.55 |

Ultraviolet-Visible Light Spectroscopy Studies. The UV-Vis experiments were conducted on a Hewlett Packard spectrophotometer (model 8453). A semi micro rectangular quartz spectrophotometer cell with a path length of 10 mm was used for the UV-vis measurements. The absorbance was measured over a range from 190 nm to 1.10 m.

Scanning Electron Microscopy Studies. Images were obtained using a Zeiss Gemini 500 Scanning Electron Microscope. A working voltage of 1.0 keV was used for imaging along with a 20.0 μm aperture. A high efficiency secondary electron detector was mixed with the in lens detector to improve topographical imaging while maintaining a high resolution.

Energy density. Based on the rate data for poly(phenyl-phenazine) 10% CL from this work and data on a commercial LiNMC from this source, the energy density and power density of the active material and of the cathode were calculated based on Eq. (8) and Eq. (9), respectively:

$$\text{Energy density} = C_{sp} \times V \quad (8)$$

$$\text{Power Density} = C_{sp} \times V \times C\text{-rate} \quad (9)$$

Where $C_{sp}$ is the specific capacity, V is the average discharge potential versus a lithium metal anode, and C-rate is the C-rate the coin cell was discharged at.

Synthesis and Characterization.

9,10-Dihydrophenazine

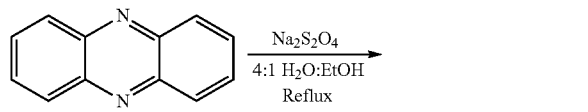

Ethanol and DI water were degassed by sparging with nitrogen for 30 min. 400 mL of water and 100 mL of ethanol were added to a 1 L round bottom. Phenazine (4.00 g, 22.2 mmol, 1 equiv) and sodium dithionite (46.6 g, 268 mmol, 12 equiv) were added and the solution was magnetically stirred. The reaction was heated to reflux and allowed to proceed for 4 hrs. Reaction is complete when no solid blue particulate remains. The reaction was allowed to cool, filtered quickly, washed with deoxygenated water, yielding (3.57 g, 88% yield) light green powder. Product was dried and stored under vacuum until use.

Poly(9,10-phenyl-phenazine)

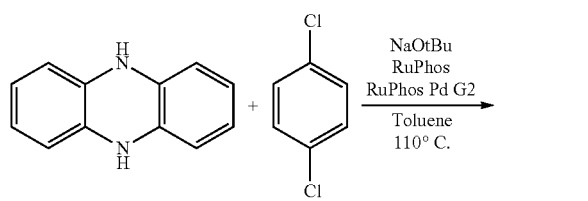

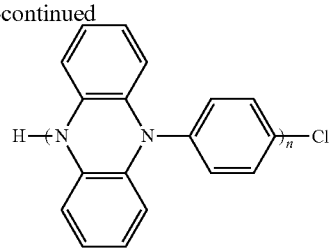

The copolymer product is shown as having specific end groups; however, one or both of the end groups may be different (e.g., the —H end group is a co-monomer unit and/or the —Cl end group is a phenazine unit). A flame dried 30 mL reaction tube was equipped with a magnetic stir bar and charged with 9,10-dihydrophenazine (273 mg, 1.50 mmol, 1 equiv), 1,4-dichlorobenzene (221 mg, 1.50 mmol, 1 equiv), RuPhos ligand (14 mg, 0.03 mmol, 0.02 equiv), RuPhos Pd G2 precatalyst (23 mg, 0.03 mmol, 0.02 equiv), and NaOtBu (346 mg, 3.6 mmol, 2.4 equiv). The reaction tube was evacuated and backfilled with $N_2$ three times and toluene (5 mL) was added via syringe. The reaction was stirred at 110° C. overnight. The mixture was allowed to cool to room temperature, and diluted into a 200 mL biphasic solution consisting of equal parts water and DCM. The insoluble polymer was filtered off and washed with an additional 100 mL of water and subsequently 100 mL of DCM. The polymer was dried under vacuum, yielding 357 mg of tan powder. IR (ATR, cm$^{-1}$): 3033, 1604, 1503, 1476, 1455, 1329, 1260, 1093, 1061, 1015, 908, 817, 723, 620, 559. Elemental Anal. Found: C, 79.63; H, 4.45; Cl, 2.71.

10% cross-linked poly(phenyl-phenazine)

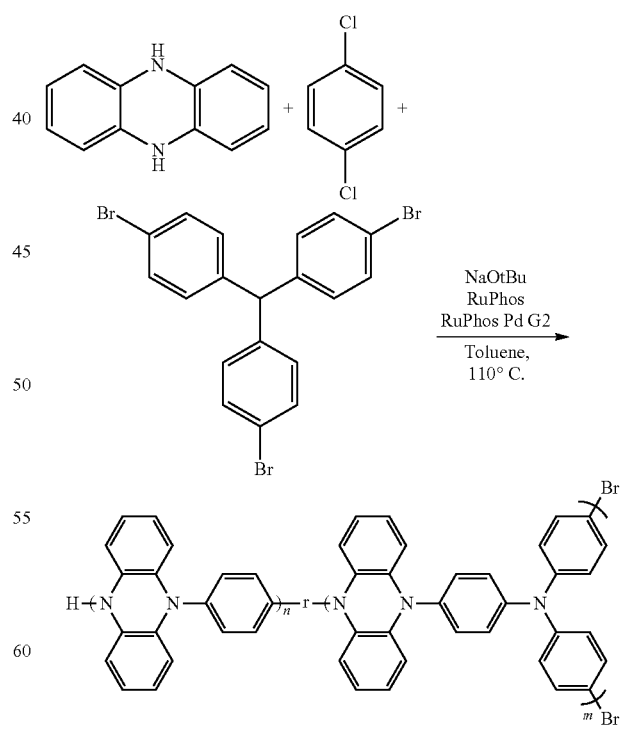

The copolymer product is shown as having specific end groups; however, one or a portion of or all of the end groups may be different (e.g., the —H end group is a co-monomer unit or cross-linking unit and/or one or more of the —Br end group(s) is a phenazine unit). A flame dried 30 mL reaction tube was equipped with a magnetic stir bar and charged with 9,10-dihydrophenazine (273 mg, 1.50 mmol, 1 equiv), 1,4-dichlorobenzene (198.5 mg, 1.35 mmol, 0.9 equiv), tris(4-bromophenyl) amine (48.2 mg, 0.1 mmol, 0.067 equiv), RuPhos ligand (14 mg, 0.03 mmol, 0.02 equiv), RuPhos Pd G2 precatalyst (23 mg, 0.03 mmol, 0.02 equiv), and NaOtBu (346 mg, 3.6 mmol, 2.4 equiv). The reaction tube was evacuated and backfilled with $N_2$ three times and toluene (5 mL) was added via syringe. The reaction was stirred at 110° C. overnight. The mixture was allowed to cool to room temperature, and diluted into a 200 mL biphasic solution consisting of equal parts water and DCM. The insoluble polymer was filtered off and washed with an additional 100 mL of water and subsequently 100 mL of DCM. The polymer was dried under vacuum, yielding 394 mg of brown powder. IR (ATR, cm$^{-1}$): 3033, 1603, 1502, 1476, 1455, 1329, 1259, 1156, 1093, 1061, 1015, 920, 817, 723, 620, 559. Elemental Anal. Found: C, 80.50; H, 4.71; Cl, 1.19.

50% cross-linked poly(phenyl-phenazine)

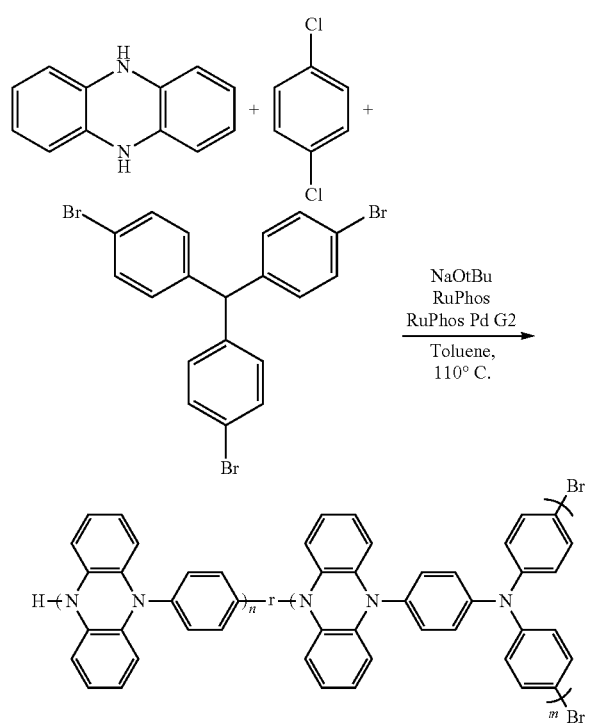

The copolymer product is shown as having specific end groups; however, one or a portion of or all of the end groups may be different (e.g., the —H end group is a co-monomer unit or cross-linking unit and/or one or more of the —Br end group(s) is a phenazine unit). A flame dried 30 mL reaction tube was equipped with a magnetic stir bar and charged with 9,10-dihydrophenazine (273 mg, 1.50 mmol, 1 equiv), 1,4-dichlorobenzene (110 mg, 0.75 mmol, 0.5 equiv), tris(4-bromophenyl) amine (241 mg, 0.5 mmol, 0.067 equiv), RuPhos ligand (14 mg, 0.03 mmol, 0.02 equiv), RuPhos Pd G2 precatalyst (23 mg, 0.03 mmol, 0.02 equiv), and NaOtBu (346 mg, 3.6 mmol, 2.4 equiv). The reaction tube was evacuated and backfilled with $N_2$ three times and toluene (5 mL) was added via syringe. The reaction was stirred at 110° C. overnight. The mixture was allowed to cool to room temperature, and diluted into a 200 mL biphasic solution consisting of equal parts water and DCM. The insoluble polymer was filtered off and washed with an additional 100 mL of water and subsequently 100 mL of DCM. The polymer was dried under vacuum, yielding 439 mg of brown powder. IR (ATR, cm$^{-1}$): 2079, 1605, 1499, 1479, 1455, 1333, 1280, 1259, 1156, 1093, 1061, 1015, 820, 730, 617, 555. Elemental Anal. Found: C, 79.96; H, 4.69; Br, 0.54; Cl, 0.67.

Poly(triarylamine-phenazine)

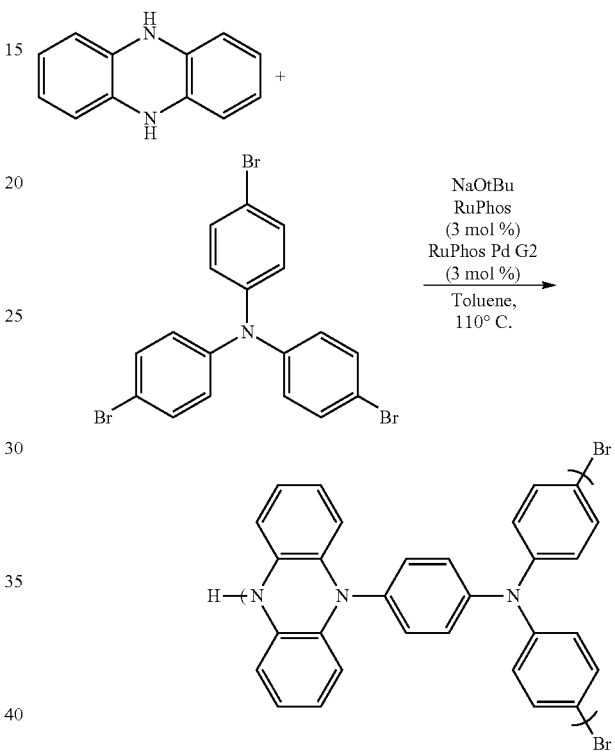

The copolymer product is shown as having specific end groups; however, one or a portion of or all of the end groups may be different (e.g., the —H end group is a cross-linking unit and/or one or more of the —Br end group(s) is a phenazine unit). A flame dried 30 mL reaction tube was equipped with a magnetic stir bar and charged with 9,10-dihydrophenazine (273 mg, 1.50 mmol, 1 equiv), tris(4-bromophenyl) amine (482 mg, 1.0 mmol, 0.067 equiv), RuPhos ligand (14 mg, 0.03 mmol, 0.02 equiv), RuPhos Pd G2 precatalyst (23 mg, 0.03 mmol, 0.02 equiv), and NaOtBu (346 mg, 3.6 mmol, 2.4 equiv). The reaction tube was evacuated and backfilled with $N_2$ three times and toluene (5 mL) was added via syringe. The reaction was stirred at 110° C. overnight. The mixture was allowed to cool to room temperature, and diluted into a 200 mL biphasic solution consisting of equal parts water and DCM. The insoluble polymer was filtered off and washed with an additional 100 mL of water and subsequently 100 mL of DCM. The polymer was dried under vacuum, yielding 414 mg of brown powder. IR (ATR, cm$^{-1}$): 3028, 1606, 1497, 1479, 1456, 1310, 1282, 1256, 1158, 1099, 1060, 1013, 822, 817, 732, 616, 553. Elemental Anal. Found: C, 76.83; H, 4.59; Br, 1.49.

TABLE 5

Diffusion coefficients of PF6− in each of the polymers determine from plots of $Z_{re}$ versus $\omega^{-1/2}$ for the low frequency EIS data.

| | $D_{PF6-}$ [cm$^2$/s] |
|---|---|
| poly(phenyl-phenazine) | $6.6 \times 10^{-10}$ |
| poly(phenyl-phenazine) 10% CL | $5.1 \times 10^{-10}$ |
| poly(phenyl-phenazine) 50% CL | $7.7 \times 10^{-11}$ |
| poly(triarylamine-phenazine) | $2.3 \times 10^{-10}$ |

TABLE 6

Energy and power density of poly(phenyl-phenazine) 10% CL and commercial LiNMC normalized to the weight of the active material and weight of the cathode.

| Cathode | Capacity [mAh/g] | C-Rate | Voltage vs Li/Li$^+$ | Wt % | Energy Density [Wh/kg active material] | Power Density [W/kg active material] | Energy density [Wh/kg] | Power Density [W/kg] |
|---|---|---|---|---|---|---|---|---|
| poly(Ph-PZ)-10 | 198 | 0.5 | 3.4 | 0.3 | 673 | 337 | 202 | 101 |
| poly(Ph-PZ)-10 | 166 | 20 | 3.4 | 0.3 | 564 | 11300 | 169 | 3390 |
| poly(Ph-PZ)-10 | 122 | 120 | 3.4 | 0.3 | 415 | 49800 | 124 | 14900 |
| poly(Ph-PZ)-10 | 167 | 1 | 3.4 | 0.6 | 567 | 567 | 340 | 340 |
| poly(Ph-PZ)-10 | 140 | 20 | 3.4 | 0.6 | 476 | 9520 | 286 | 5710 |
| poly(Ph-PZ)-10 | 86.2 | 120 | 3.4 | 0.6 | 293 | 35200 | 176 | 21100 |
| Commercial LiNMC[1] | 178 | 0.5 | 3.75 | 0.9 | 668 | 334 | 601 | 300 |
| Commercial LiNMC[1] | 129 | 5 | 3.75 | 0.9 | 484 | 2420 | 435 | 2180 |
| Commercial LiNMC[1] | 54 | 20 | 3.75 | 0.9 | 203 | 4050 | 182 | 3650 |

Example 2

This example provides a description of polymers and batteries of the present disclosure and method of making and characterization of same.

FIGS. 24 to 30 show additional examples of polymers and batteries of the present disclosure. These figures also provide characterization data related to the polymers and batteries. The polymers and batteries were made and characterized generally as described in Example 1.

Example 3

This example provides a description of polymers and batteries of the present disclosure and method of making and characterization of same.

Figure 31:
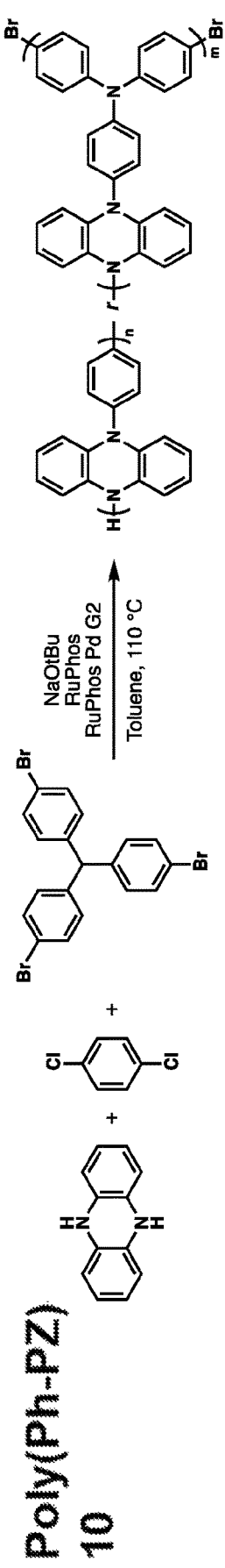
FIG. 31 shows theoretical capacities obtained by discharging to lower potentials.
Figure 31:
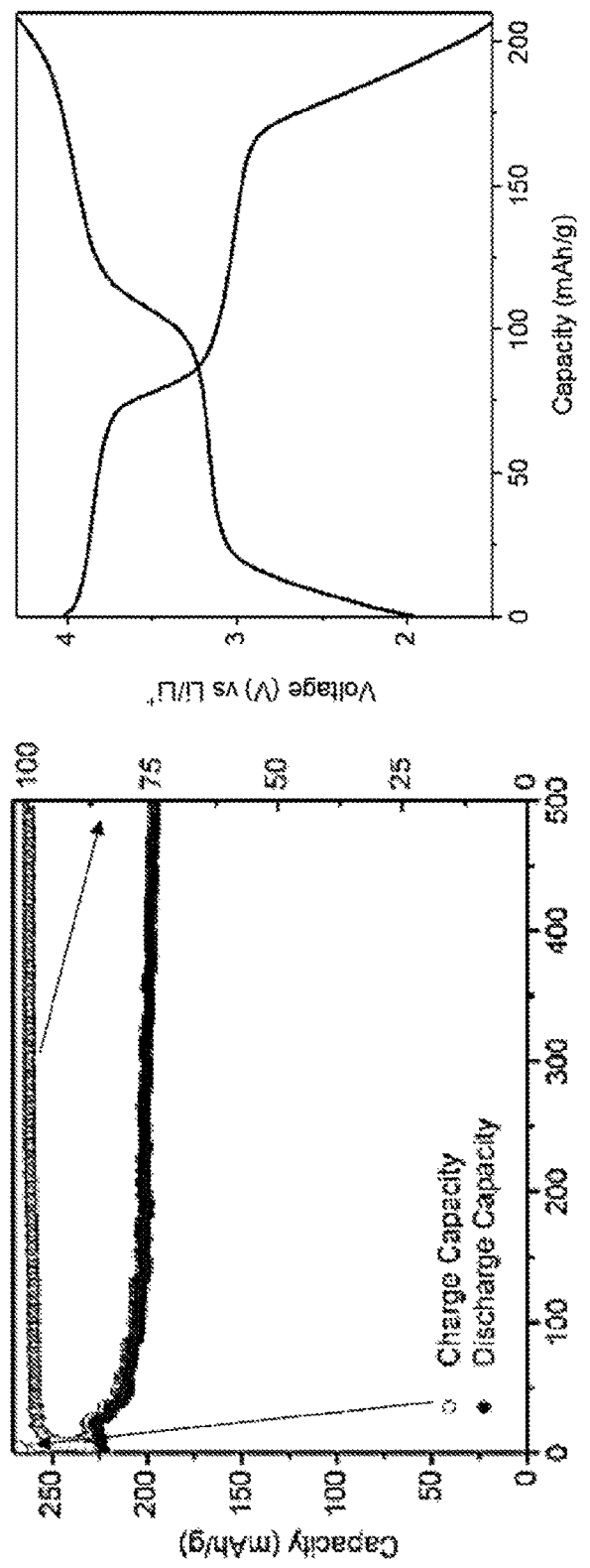
Figure 32:
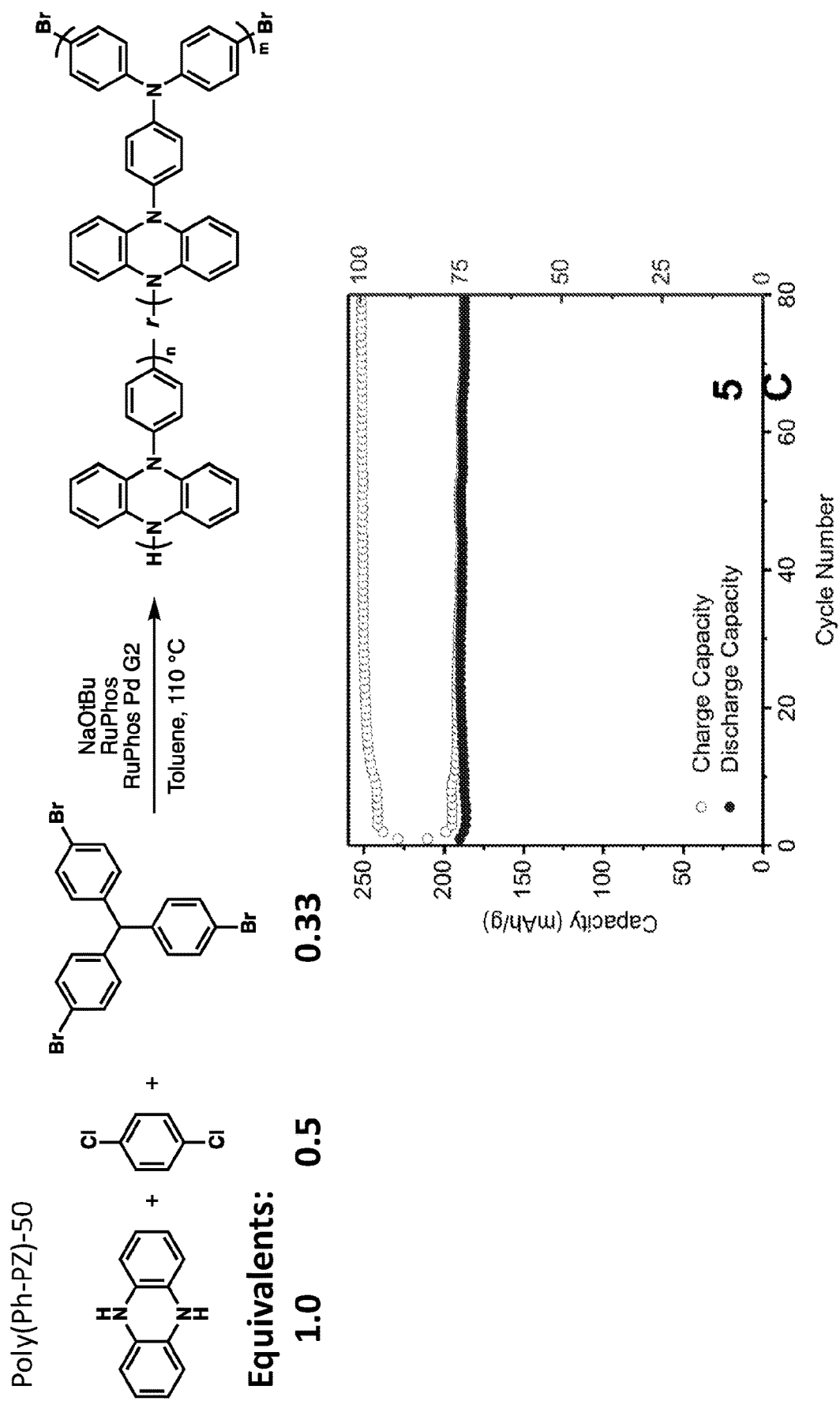
FIG. 32 shows theoretical capacities obtained by discharging to lower potentials.

FIGS. 31 and 32 show additional examples of polymers and batteries of the present disclosure. These figures also provide characterization data related to the polymers and batteries. The polymers and batteries were made and characterized generally as described in Example 1.

Example 4

This example provides a description of polymers of the present disclosure characterization of same.

Figure 33:
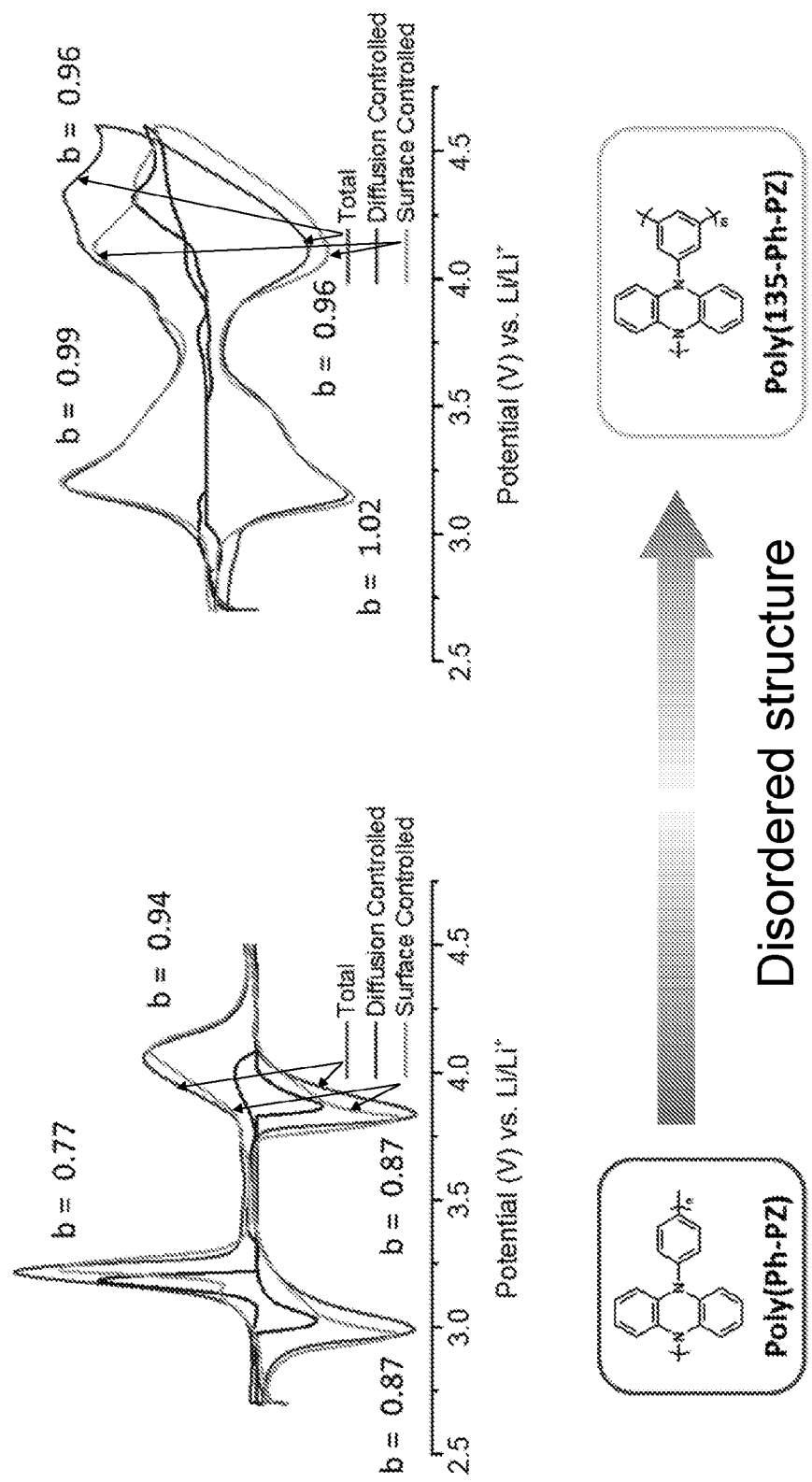
FIG. 33 shows CV data. Left is CV data for poly(Ph-PZ) and right is CV data for poly(135-Ph-PZ). Poly(135-Ph-PZ) shows pseudocapacitive energy storage. Scan rate was 0.25 $mVs^{-1}$, b values acquired from CV scans of cathode composites (0.05 to 5 $mVs^{-1}$), and k values acquired from CV scans of cathode composites (0.05 to 1 $mVs^{-1}$). Contributions were from both cathodic peaks. The pseudocapacitive storage stems from the disordered structure in poly(135-Ph-PZ).

FIG. 33 shows CV data comparing poly(Ph-PZ) and poly(135-Ph-PZ). Poly(135-Ph-PZ) shows pseudocapacitive energy storage. Without intending to be bound by any particular theory, it is considered the pseudocapacitive energy storage is due to the disordered structure of poly (135-Ph-PZ).

The electrochemical behavior of poly(Ph-PZ), a linear polymer, and poly(135Ph-PZ), a fully cross-linked polymer, were compared in terms of diffusion-controlled behavior. This was done by analyzing the current response with sweep rate, taking advantage of the fact that surface-controlled or "capacitive" current scales with sweep rate while diffusion-controlled current scales with the square root of sweep rate. By this analysis, it was found that in poly(Ph-PZ), a significant portion of current arises from diffusion-controlled processes, consistent with battery-like behavior. Meanwhile, almost all of the current from poly(135Ph-PZ) arises from surface-controlled processes, consistent with pseudo-capacitive behavior. Pseudocapacitors offer the advantages of both the high energy densities of battery materials, along with the high-power densities of capacitor type materials, due to the lack of diffusive limitations.

Figure 34:
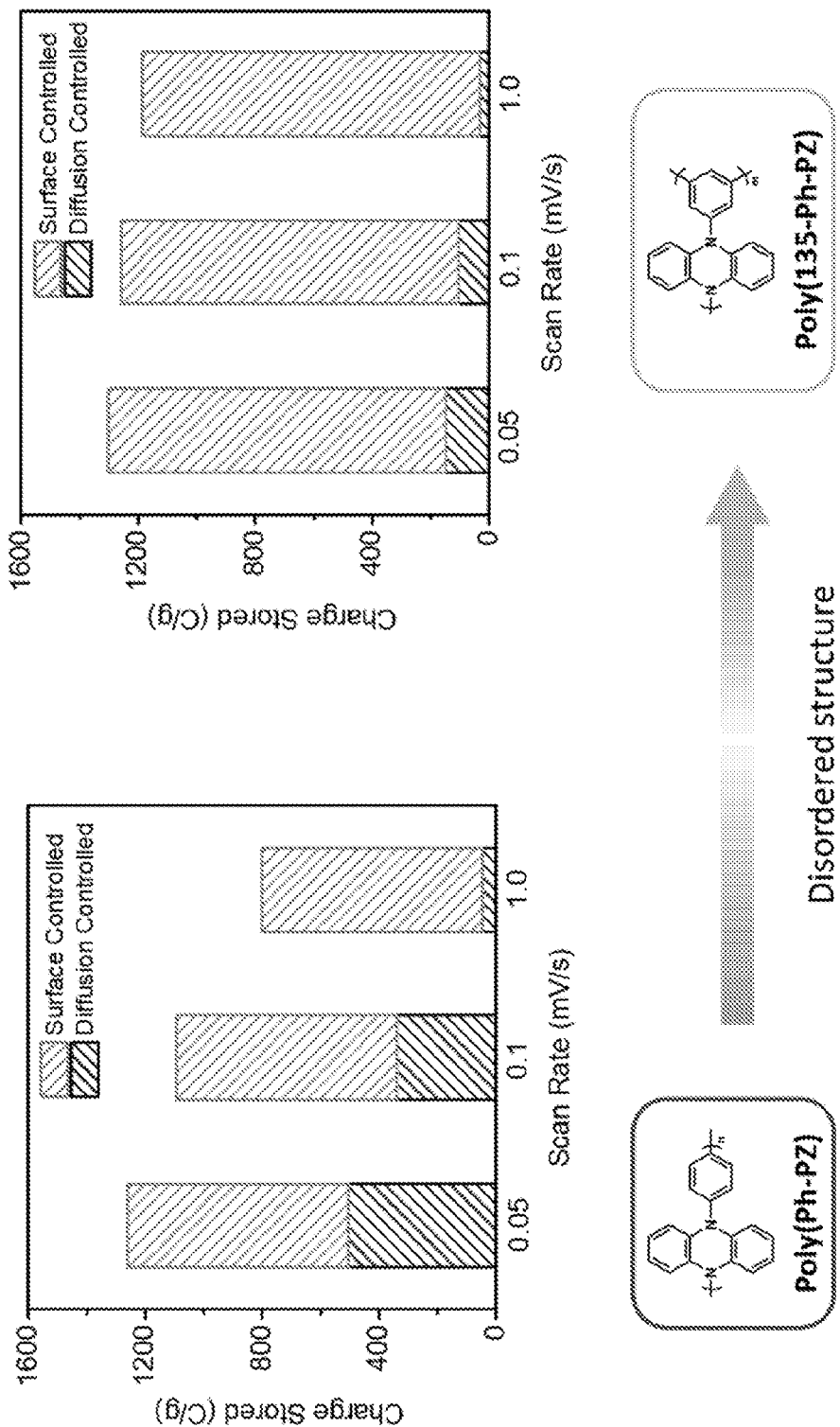
FIG. 34 shows a comparison of charge storage for poly(Ph-PZ) (left) and poly(135-Ph-PZ) (right). The pseudocapacitive storage mechanism leads to better rate performance for poly(135-Ph-PZ) relative to poly(Ph-PZ). K values were acquired from CV scans of cathode composites (0.05 to 1 $mVs^{-1}$).

While charge storage arising from diffusion-controlled processes will drop off with increasing rates of charge and discharge, charge storage from surface-controlled processes will not. As shown in the FIG. 34, this is beneficial to the rate performance of poly(135Ph-PZ). The charge stored in poly (Ph-PZ) decreases with increasing scan rate due to decreases in the charge stored in diffusion limited processes. Meanwhile, the charge stored in poly(135Ph-PZ) remains almost constant with increasing scan rate due to the large majority of the current arising from surface-controlled charge storage.

Figure 35:
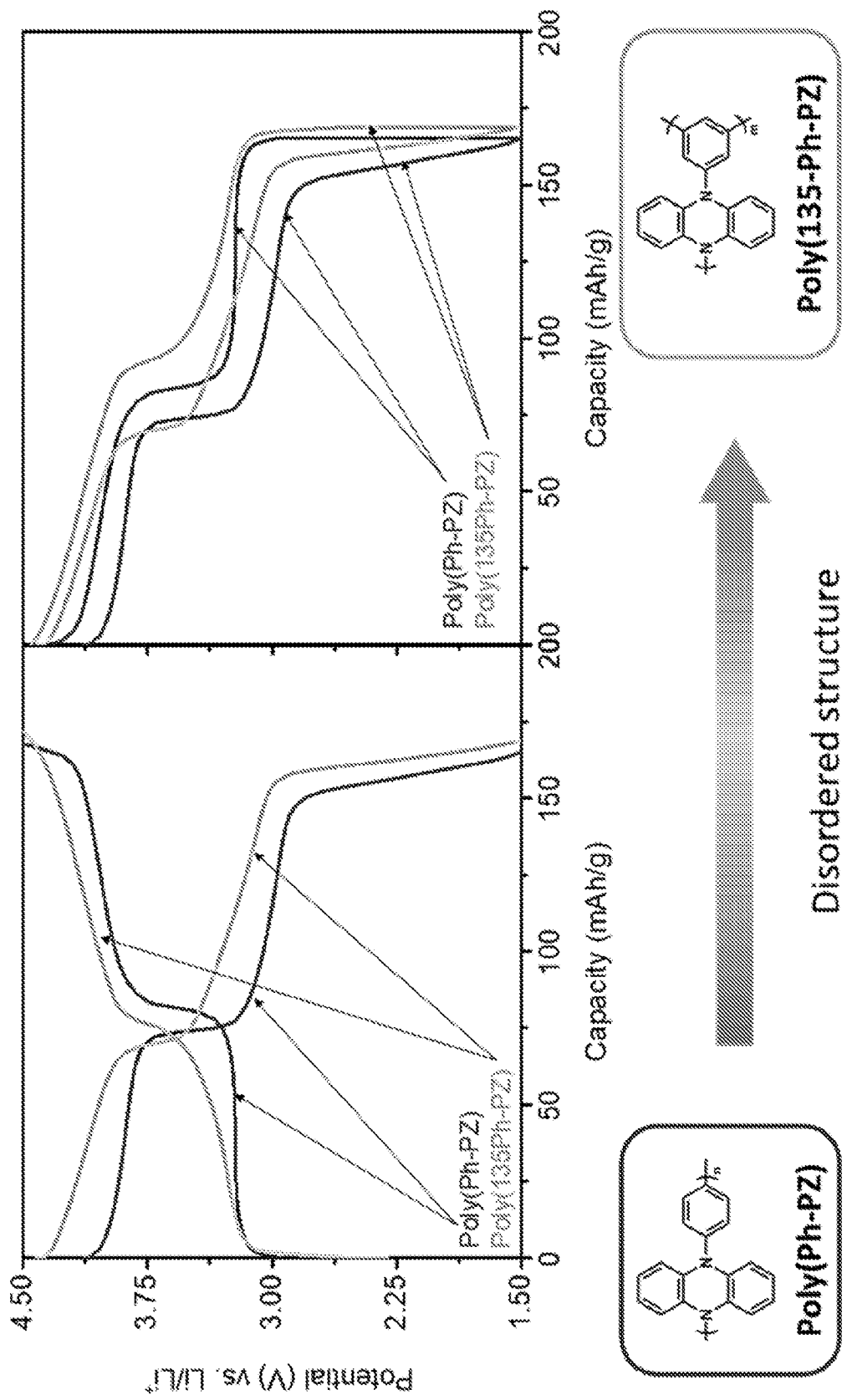
FIG. 35 shows GCDC profiles that exhibit sloping discharge plateaus and reduced polarization in poly(135-Ph-PZ).
Figure 36:
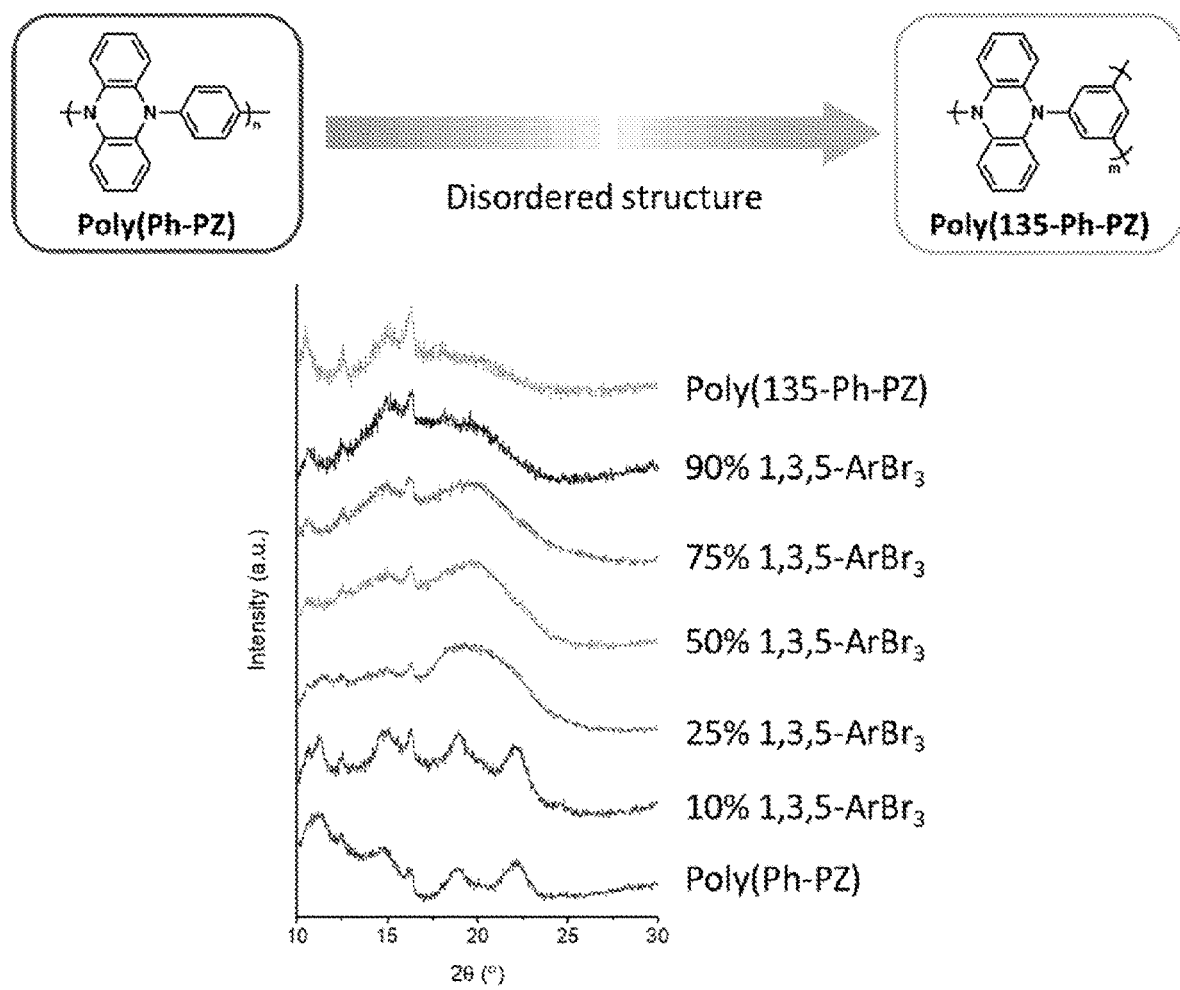
FIG. 36 shows powder X-ray diffraction spectra of poly(Ph-PZ), poly(135-Ph-PZ), and polymers synthesized using various equivalents of cross-linker according to equations 1 and 2 described herein.

The charge/discharge profiles from galvanostatic charge/discharge experiments (FIG. 35) exhibit the increased pseudocapacitive behavior of poly(135Ph-PZ). While poly (Ph-PZ) exhibited discrete redox plateaus, the plateaus of poly(135Ph-PZ) are both sloping and show reduced polarization. Both these traits are characteristic of a pseudocapacitive material.

With the increased incorporation of 1,3,5-ArBr$_3$, the short-range ordering observed in the powder XRD pattern of poly(Ph-PZ) decreases. Specifically, the two peaks observed at high angles (~18 and 23°) merge and broaden until they are no longer observed. The lowest angle peak shifts to lower 2θ values, consistent with a structural expansion. In poly(135Ph-PZ), all peaks have become so broad that the material appears to be completely amorphous and lack even short-range ordering. It is considered that the increased disorder in the polymer structure brought about by the increase in the cross-linking unit is responsible for the increase in the pseudocapacitive behavior in poly(135Ph-PZ). The diffusion-limited current observed in poly(Ph-PZ) could be a product of ion transport through the crystalline domains in poly(Ph-PZ)'s structure. By removal of these regions, ions can more easily move unimpeded through the polymer in poly(135Ph-PZ).

Figure 37:
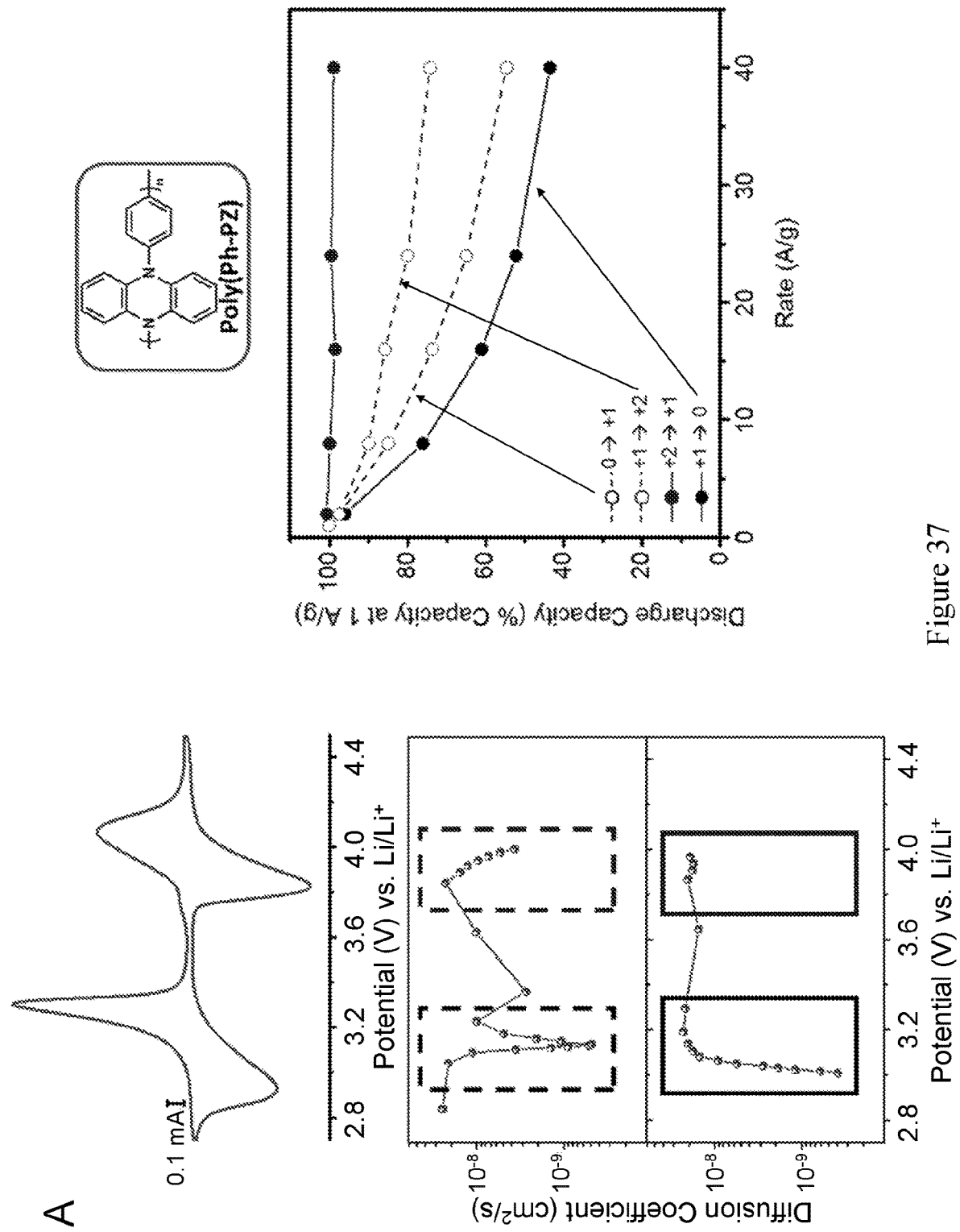
FIG. 37 shows (A and B) the cyclic voltammogram, galvanostatic intermittent titration data, and a plot of charge stored or delivered (relative to the charge stored or delivered at a rate of 1 A $g^{-1}$) from each redox event when cycled at different current rates for poly(Ph-PZ). The galvanostatic intermittent titration shows that ionic diffusion decreases in potential ranges where faradaic processes occur. Additionally, a plot displays the capacity delivered by each redox event when cycled at varying current rates. This is shown as (A) discharge capacity versus rate and (B) discharge capacity versus cycle cumber. This plot shows that capacity stored in the first redox event decreases at higher current rates.
Figure 37:
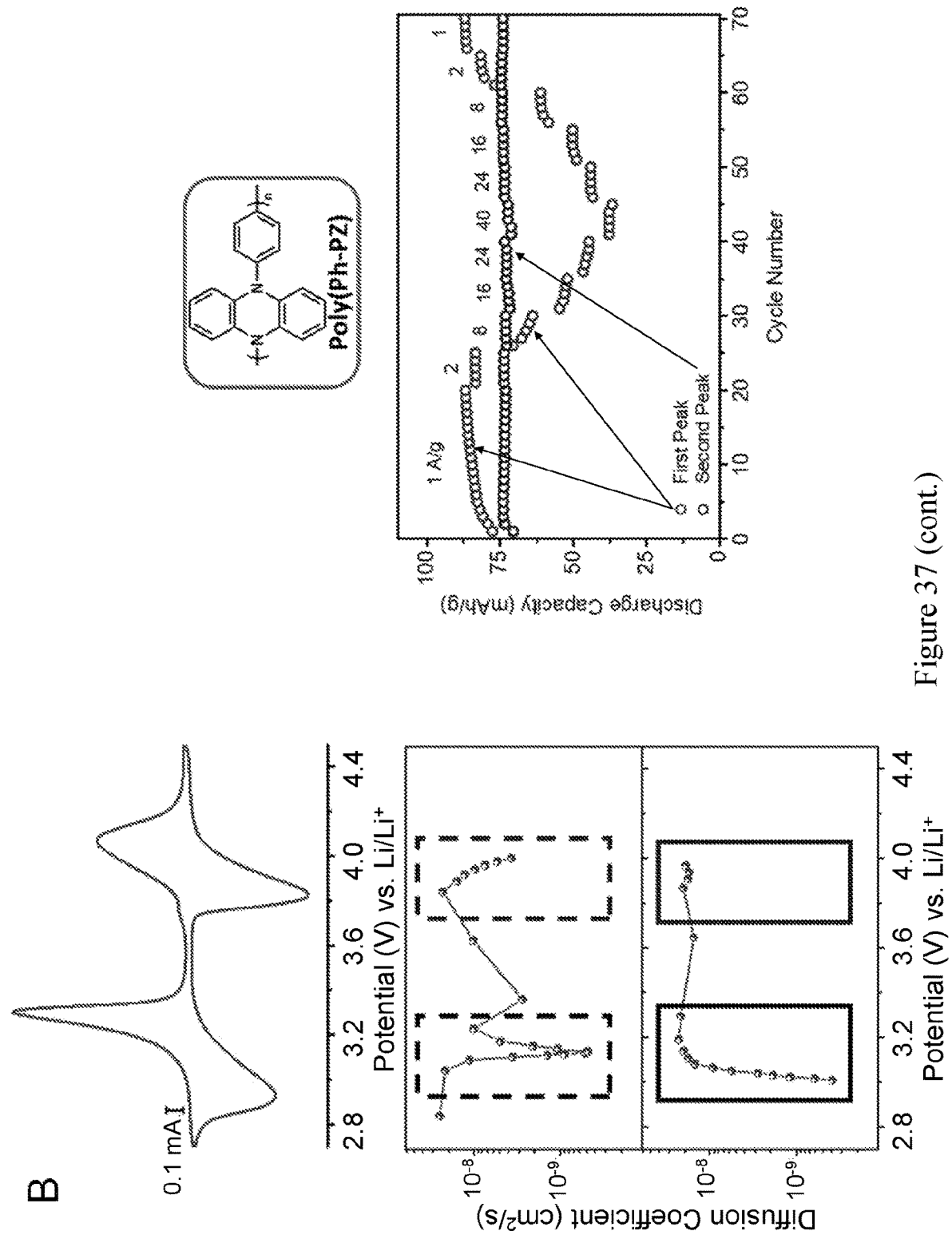
Figure 38:
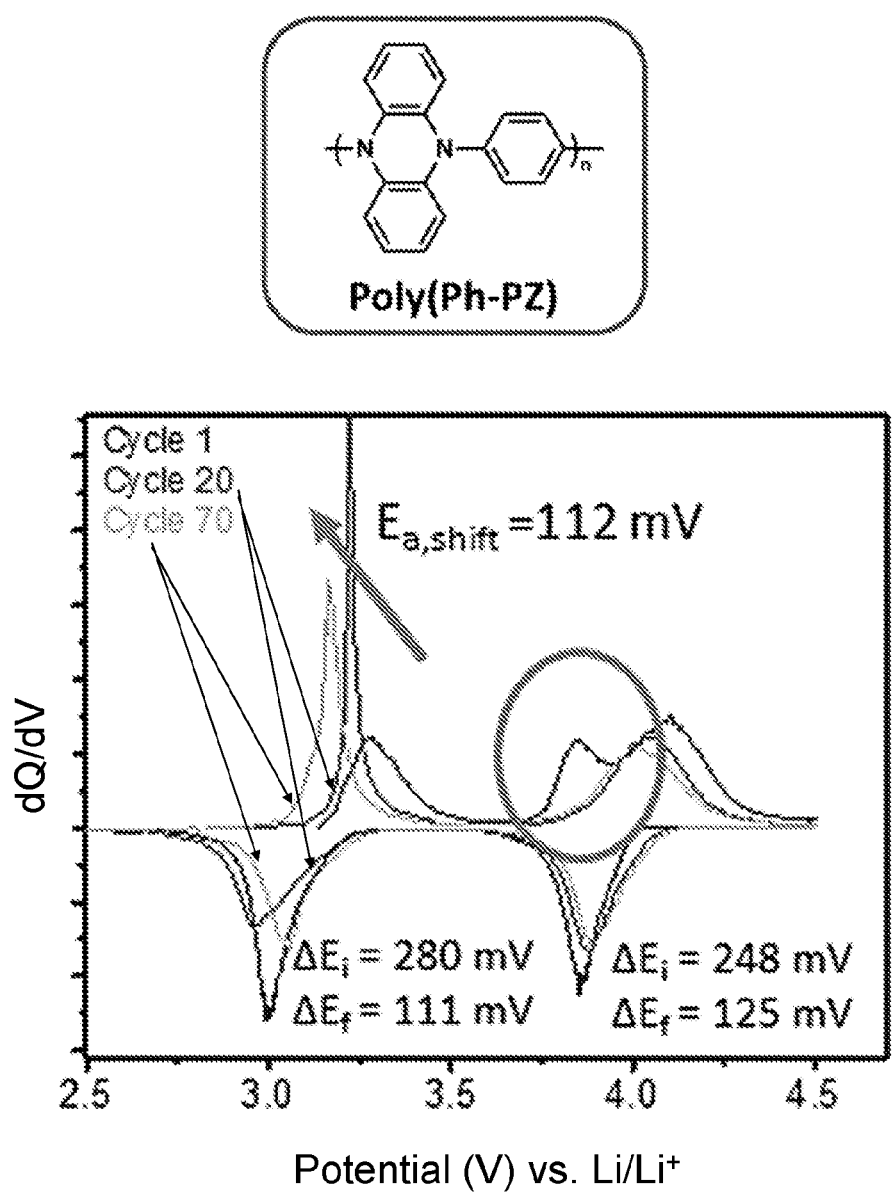
FIG. 38 shows dQ/dV vs potential plot of galvanostatic charge-discharge cycling of poly(Ph-PZ) polymer cathode and the powder x-ray diffraction pattern of the polymer composite at different states of charge (circles correspond to colored x-ray diffraction patterns at that state of charge).
Figure 38:
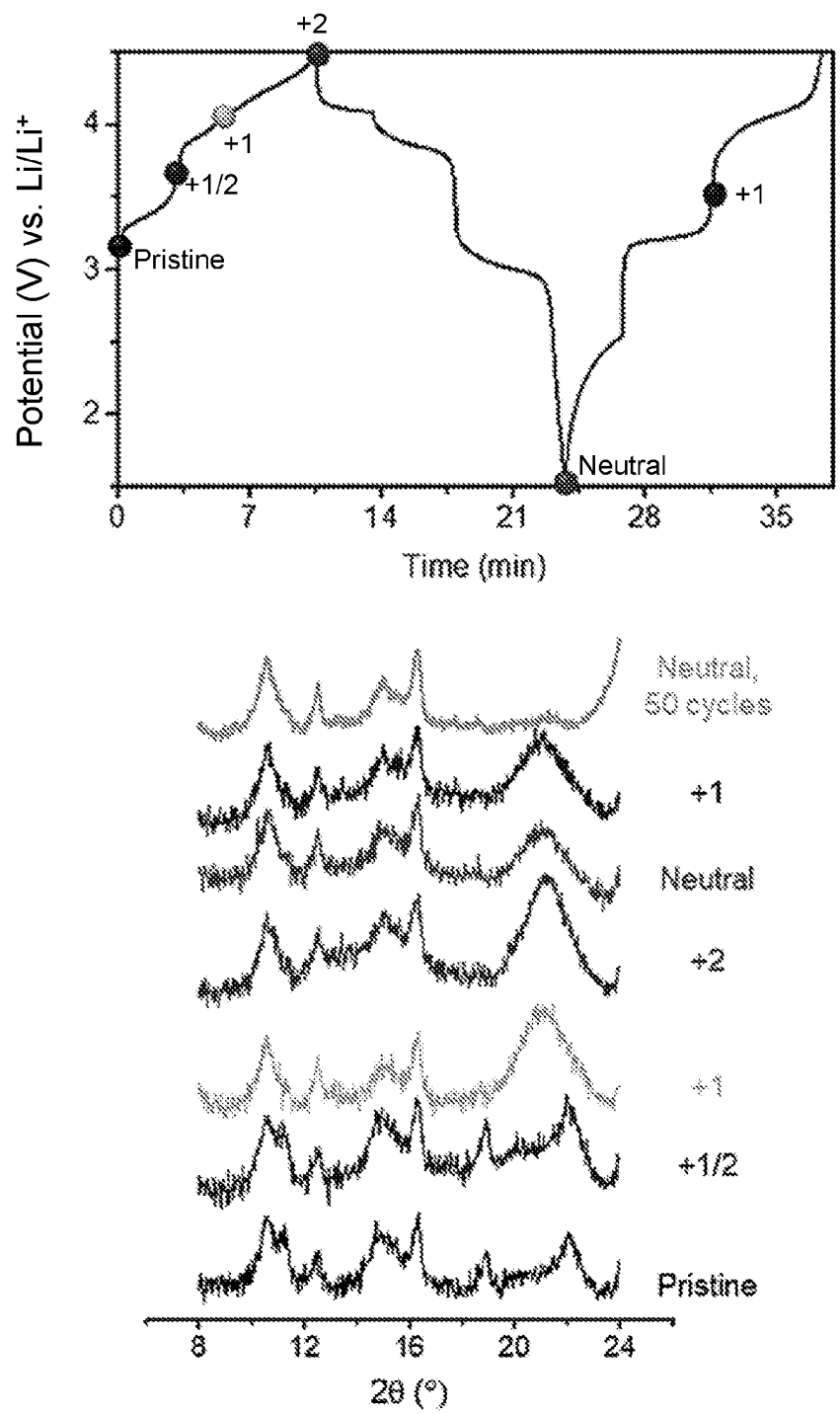

Further analysis of diffusion through poly(Ph-PZ) using galvanostatic intermittent titration technique reveals a sharp decrease in the diffusion coefficient at the redox couples (FIG. 37). FIG. 37 shows diffusion through the polymer decreases as the polymer undergoes its redox processes. These drops in the diffusion coefficients with charge and discharge correspond with the decreased capacity retention with increasing rate in battery testing. The redox processes corresponding with the polymer being discharge from the +2 state to a +1 state does not exhibit a drop in the measured diffusion coefficient in GITT. This redox couple also exhibits 100% capacity retention with increasing rate of discharge up to 40 A/g, suggesting that the drop observed in the diffusion coefficients corresponding to the other redox couples is responsible for the decreased rate performance.

Poly(Ph-PZ) exhibits a decrease in peak splitting with increased cycling. Peak splitting often corresponds to some type of phase transition accompanying the change in the charge state of a material, often induced by the exchange of solvent molecule and ions between the active material and the electrolyte solution. Further, in the first cycle, the first redox couple is found to be split into two smaller peaks. XRD was used to analyze disassembled coin cells, and it was found that for the first half of the first redox couple, the material retained its crystalline domains without any observed changes. In oxidation of the second half of this first charge to get the polymer fully into the +1 state, the two peaks at high angles merge into one, suggesting this process corresponds to a phase change and is likely the diffusion limited portion of the redox couple. For the first cycle, it required an additional overpotential to oxidize the polymer fully to the +1 state, likely associated with "breaking in" the polymer and incorporating solvent molecules and ions into the crystalline domains for the first time. Once the structure is first disturbed, it was found the polymer does not fully return to its pristine state, even with discharge. Instead, with further cycling, the merged peak at ~21° broadens out such that it is barely observed.

Figure 39:
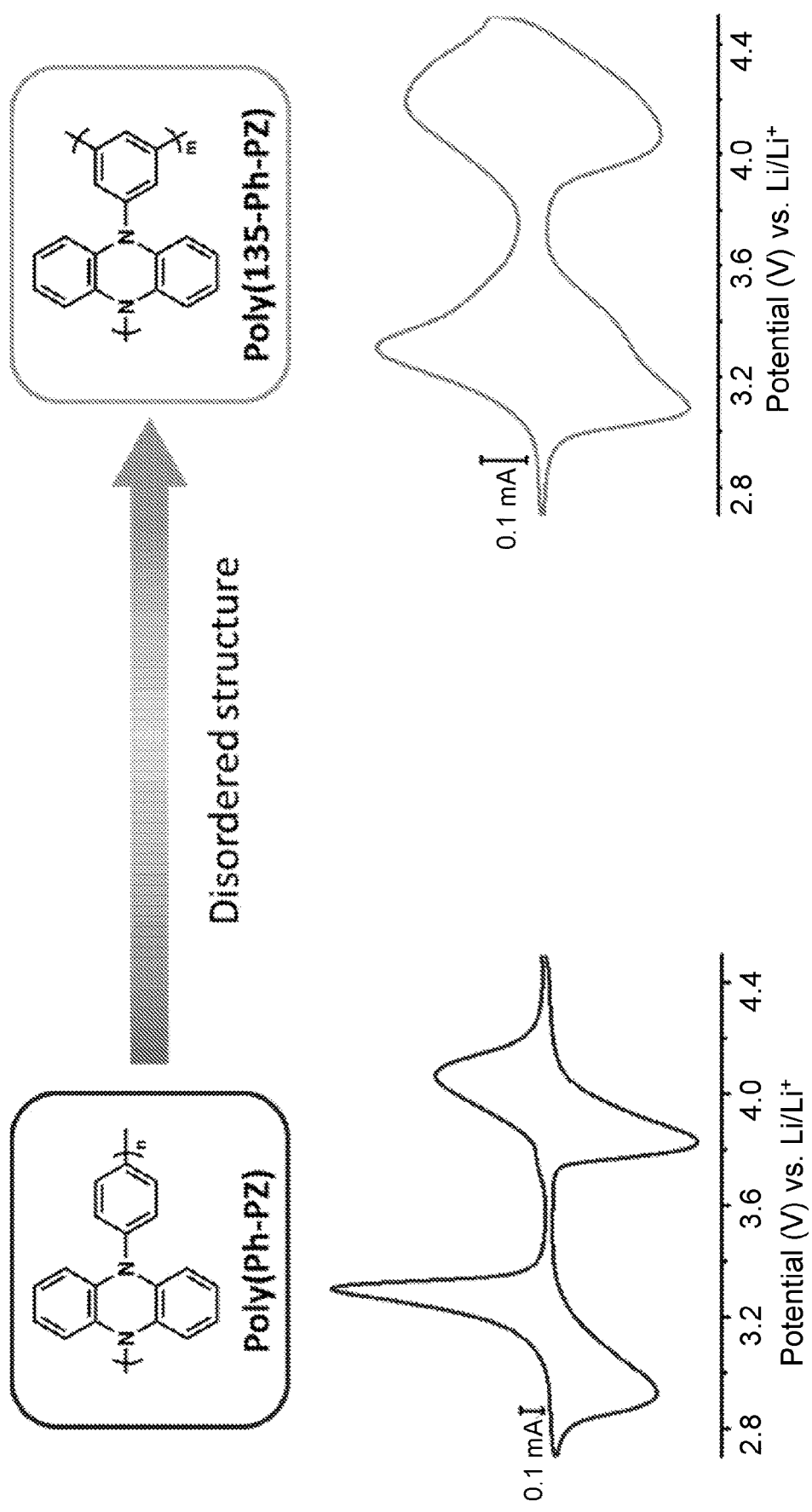
FIG. 39 shows (A) CV data for poly(Ph-PZ) and poly (135-Ph-PZ). (B) shows the corresponding diffusion coefficients for poly(Ph-PZ) and poly(135-Ph-PZ). (C) shows the cyclic voltammogram, galvanostatic intermittent titration data, and a plot of charge stored or delivered (relative to the charge stored or delivered at a rate of 1 A g$^{-1}$) from each redox event when cycled at different current rates for poly (135-Ph-PZ).
Figure 39:
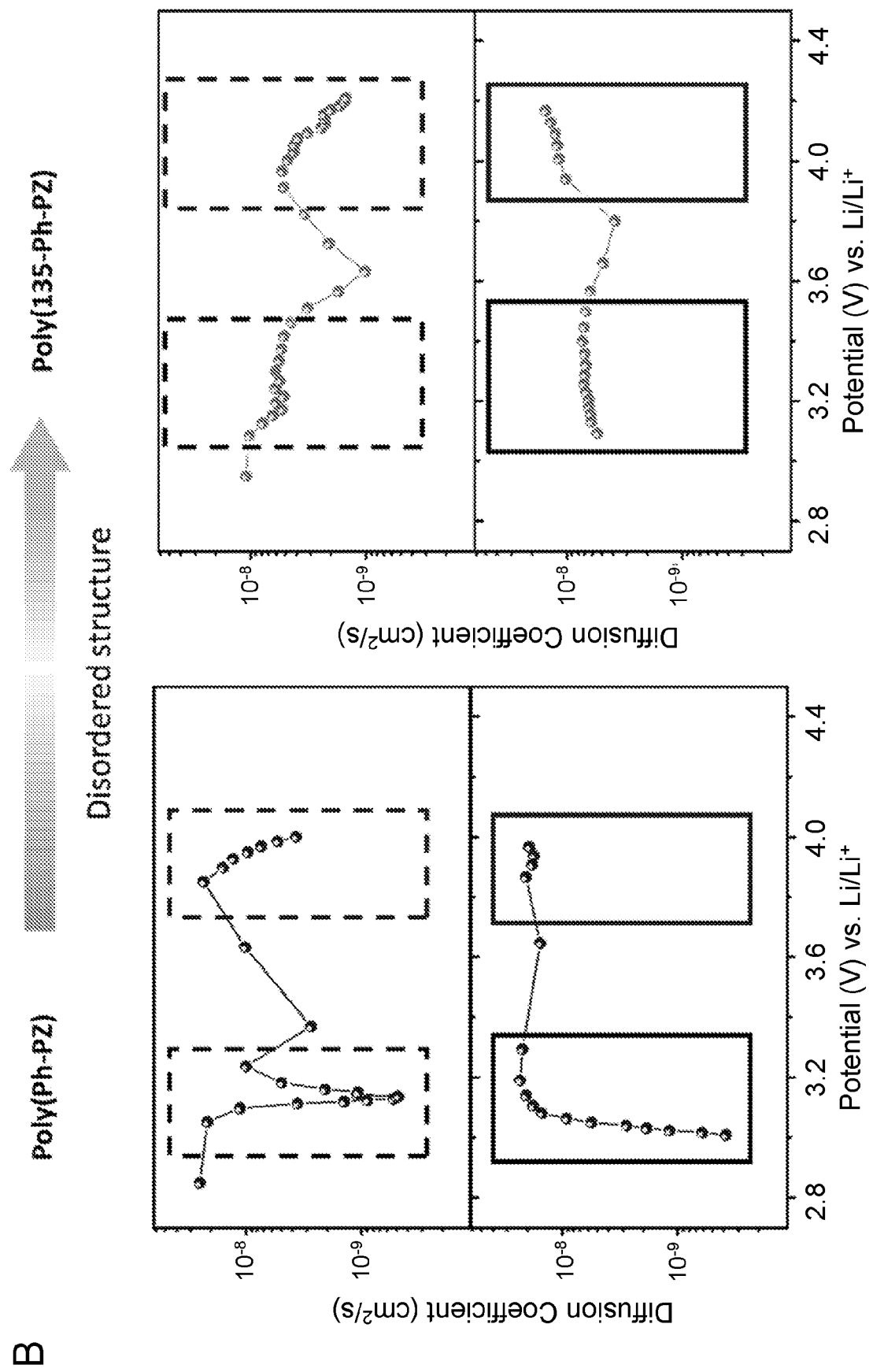
Figure 39:
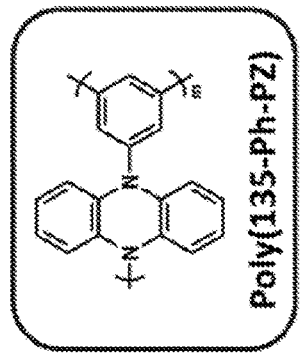
Figure 39:
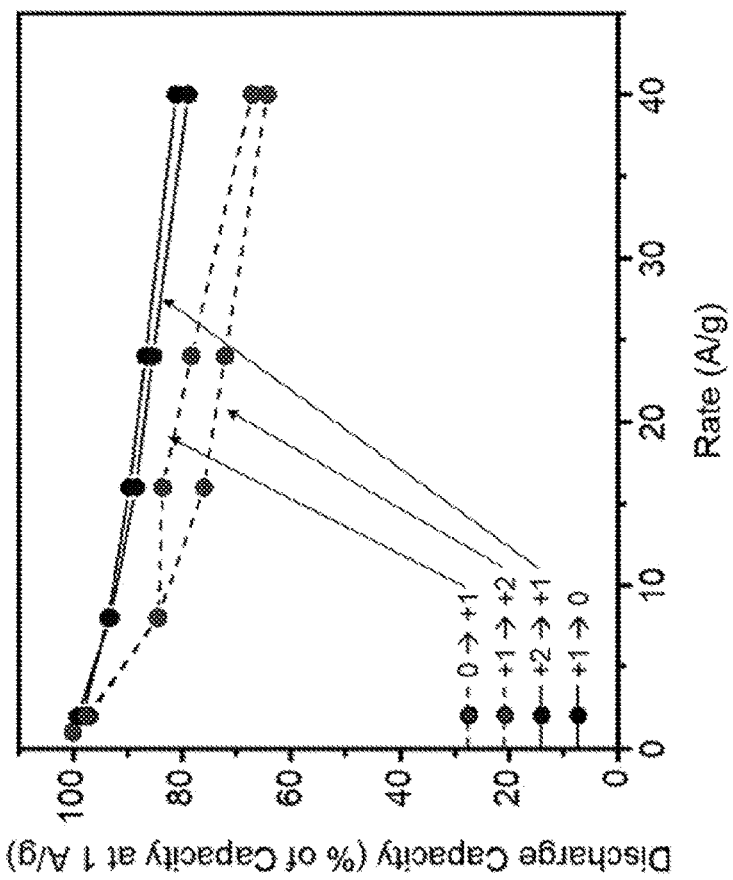
Figure 39:
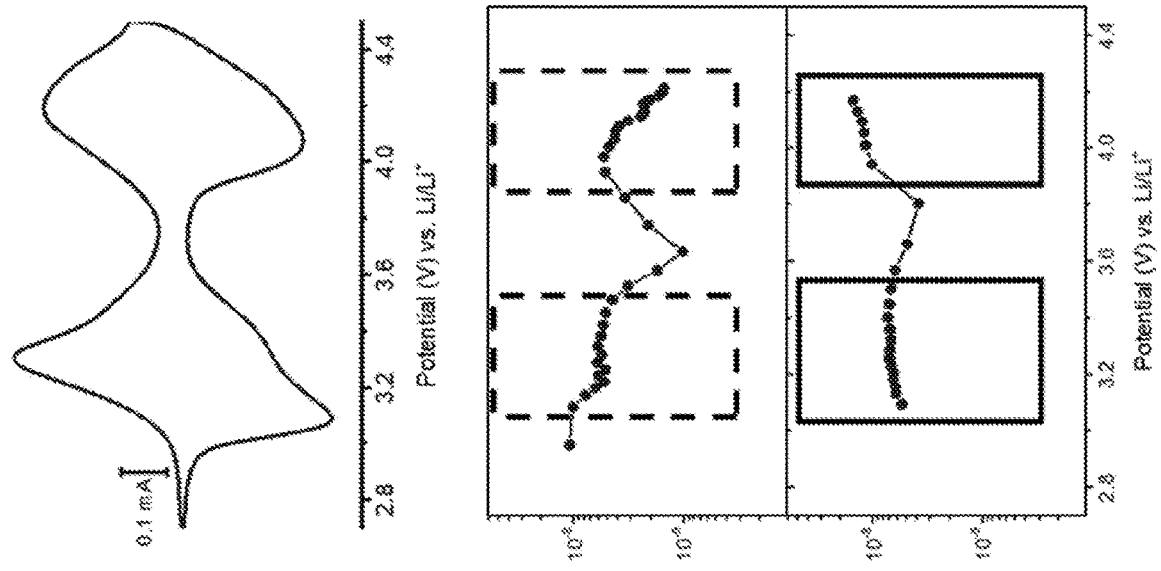

FIG. 39 shows further analysis of diffusion through poly(135Ph-PZ) using galvanostatic intermittent titration technique reveals diffusion coefficients which are nearly constant at the redox couples. This corresponds with diffusion independent of the faradaic processes occurring in the material. Despite the little to no decrease in measured ion diffusion rate with charge state, a decrease in capacity with increasing rate of discharge was observed. The small $\Delta E_{peak}$ suggests there was less of a phase transition. Broad CV may be attributed to macroscopic distribution of redox sites with electronic environments. A second redox peak shift to higher potential leading to high energy densities.

Figure 40:
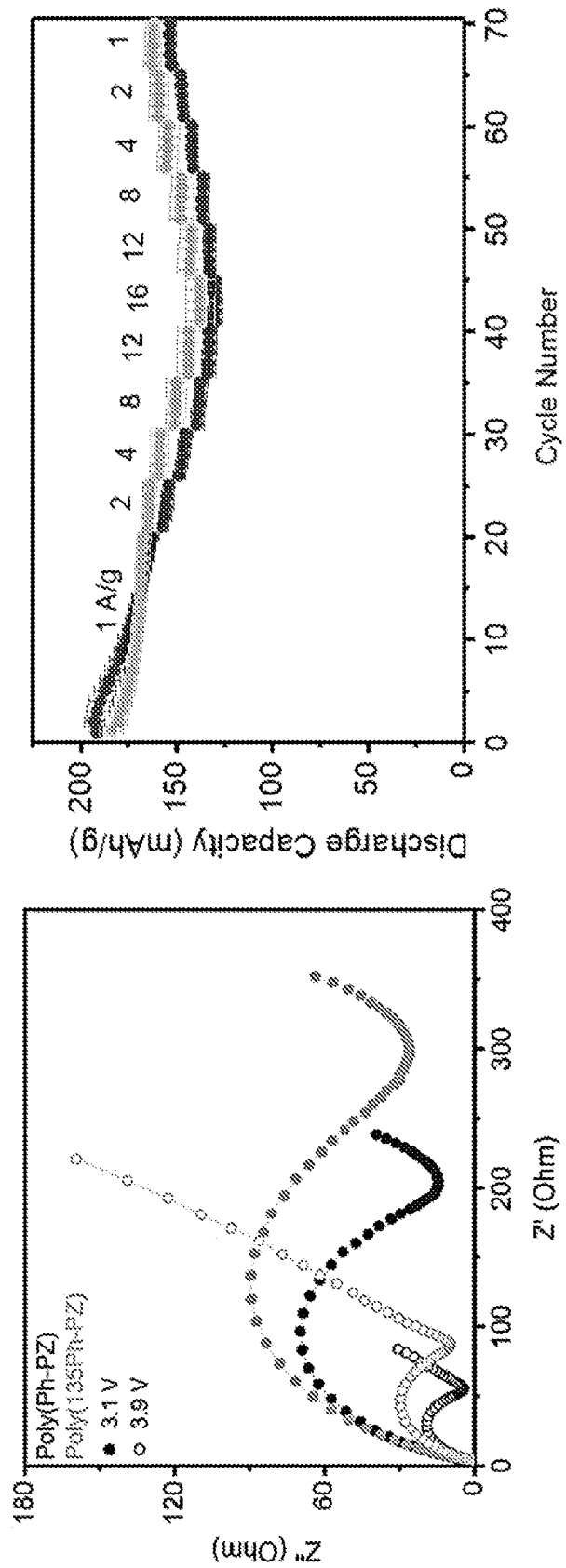
FIG. 40 shows the electrochemical impedance of poly (Ph-PZ) and poly(135-Ph-PZ) cathode composites at 3.1 V and 3.9 V vs Li$^+$/Li and the galvanostatic discharge capacities of each cathode at current rates from 1 A g$^{-1}$ to 16 A g$^{-1}$.

FIG. 40 shows poly(135Ph-PZ) exhibits increased electronic resistance compared to poly(Ph-PZ). It is considered that the decrease in capacity of poly(135Ph-PZ) with increasing rate of discharge corresponds to electronic limitations. Meanwhile, diffusion limitations are expected to be responsible for the loss of capacity with increasing rate in poly(Ph-PZ).

Figure 41:
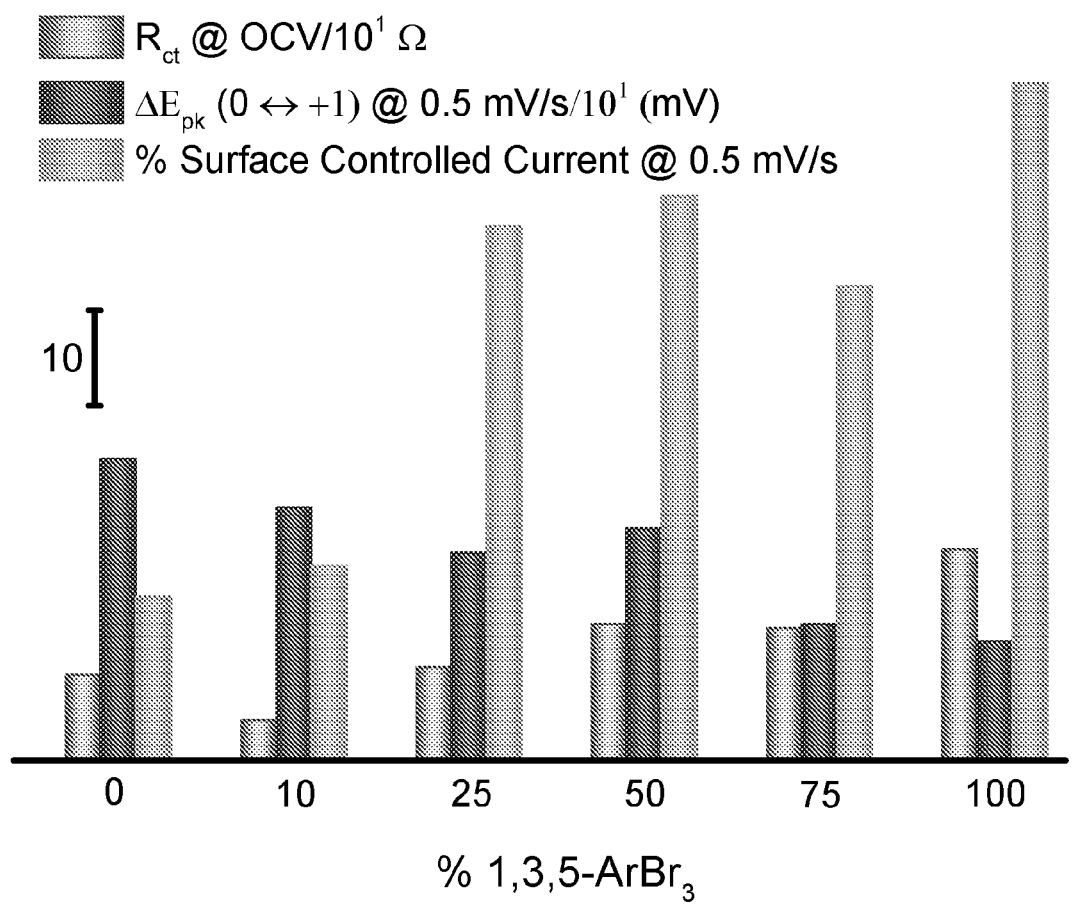
FIG. 41 shows $R_{ct}$, $\Delta E_{pk}$, and percent surface controlled current as affected by the percent of 1,3,5-ArBr$_3$. In each group of three, the bars from left to right correspond to $R_{ct}$, $\Delta E_{pk}$, and percent surface controlled current.
Figure 42:
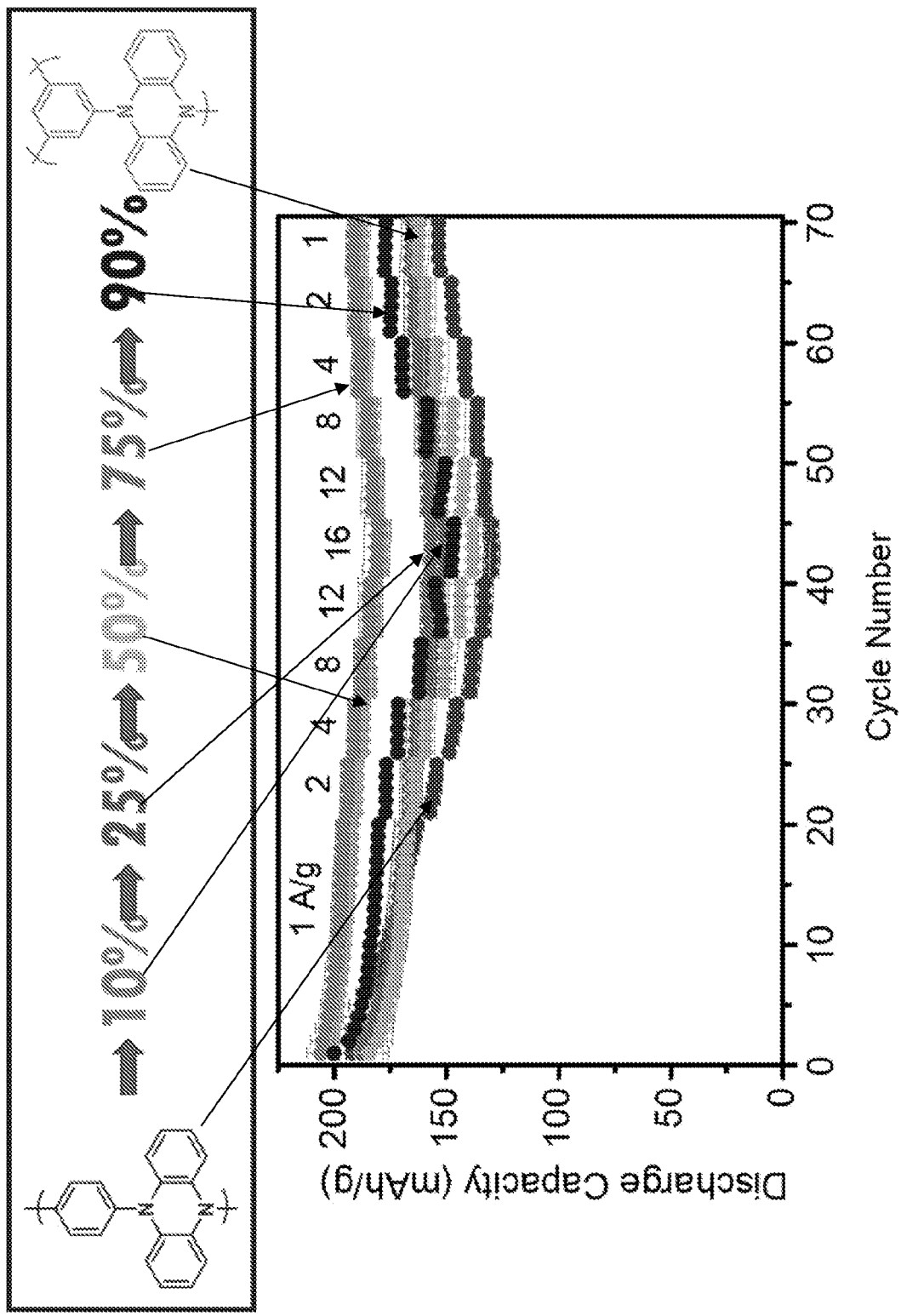
FIG. 42 shows discharge capacity of copolymers of the present disclosure with various percentages of 1,3,5,—ArBr$_3$.

Polymers with various percentages of 1,3,5-ArBr$_3$ were synthesized and tested as battery cathodes. A trend in increasing charge transfer resistance with increasing 1,3,5-ArBr$_3$ was observed, corresponding to increased electronic limitations. Meanwhile, peak splitting in the first redox couple decreased, corresponding with a decrease in structural changes upon charge and discharge in the increasingly cross-linked materials. Additionally, with increasing 1,3,5-ArBr$_3$ content, the percent of current from surface-controlled processes increased, corresponding to increasingly pseudocapacitive type charge storage. These data are presented in FIG. 41.

Around 50-75% 1,3,5-ArBr$_3$ incorporation in the polymer networks, rate performance was optimized. At this concentration of cross-linker incorporated into the polymer, the effects of increasing electronic resistance with decreasing diffusive limitations was balanced. This concentration of 1,3,5-ArBr$_3$ results in polymers with the highest energy and power densities of those presented herein.

Although the present disclosure has been described with respect to one or more particular examples, it will be understood that other examples of the present disclosure may be made without departing from the scope of the present disclosure.

The invention claimed is:
1. A phenazine polymer comprising:
a plurality of phenazine units; and
a plurality of cross-linking units or both a plurality of co-monomer units and a plurality of cross-linking units,
wherein the individual phenazine units are covalently bonded to a co-monomer unit and/or a cross-linking unit, wherein at least a portion of or all of the individual cross-linking units crosslink three or more units selected from phenazine units and/or co-monomer units, and wherein the number of phenazine units, co-monomer units, and cross-linking units is determined by the following equations:

$$a1+(b2+x3) \rightarrow \text{phenazine copolymer} \quad (1)$$

$$b+3/2x=a \quad (2),$$

$$b+(n/2)x=a \quad (10),$$

wherein 1 is the phenazine units and/or 2 is the co-monomer units and/or 3 is the cross-linking units and/or a is the amount of the phenazine units and/or b is the amount of the co-monomer units and/or x is the amount of the cross-linking units and/or N is the number of reactive sites in the cross-linking unit, and wherein the phenazine units have the following structure:

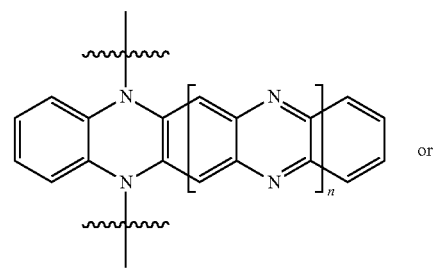

or

-continued

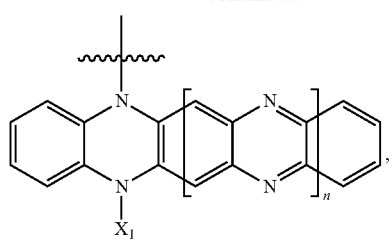

wherein n is 0 to 100 and $X_1$ is chosen from a co-monomer unit, a cross-linking unit, and —H;

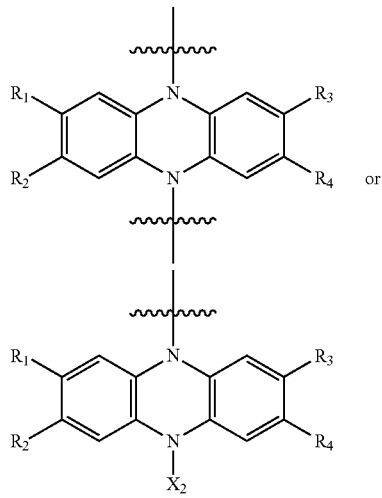

wherein $R_1$, $R_2$, $R_3$, $R_4$ are independently at each occurrence chosen from —F, —Cl, —Br, —I, and —CH=O and $X_2$ is chosen from a co-monomer unit, a cross-linking unit, and —H;

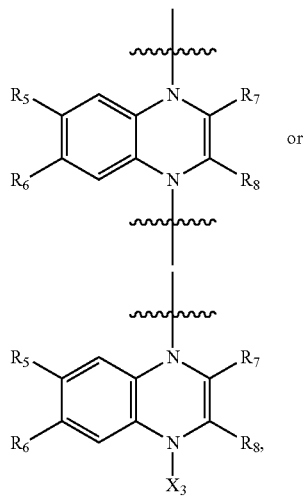

wherein $R_5$, $R_6$, $R_7$, $R_8$ are independently at each occurrence chosen from —F, —Cl, —Br, —I, and —CH=O and $X_3$ is chosen from a co-monomer unit, a cross-linking unit, and —H; or a combination thereof.

2. The phenazine polymer of claim 1, wherein the cross-linking units have the following structure:

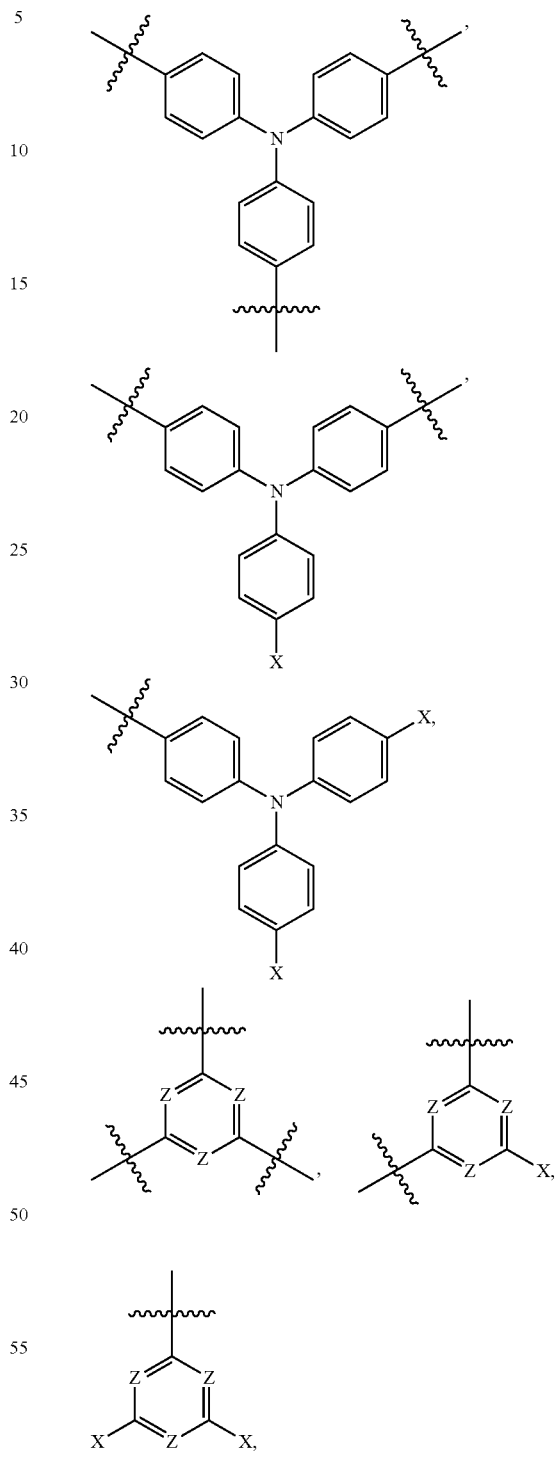

or a combination thereof, wherein Z is nitrogen or CH and X is independently at each occurrence chosen from a phenazine unit, a co-monomer unit, —H, —F, —Cl, —Br, —I, —CH=O, and —OR, wherein —OR is —OTs (tosylate), —OMs (mesylate), —OTf (triflate).

3. The phenazine polymer of claim 1, wherein the phenazine copolymer has the following structure:

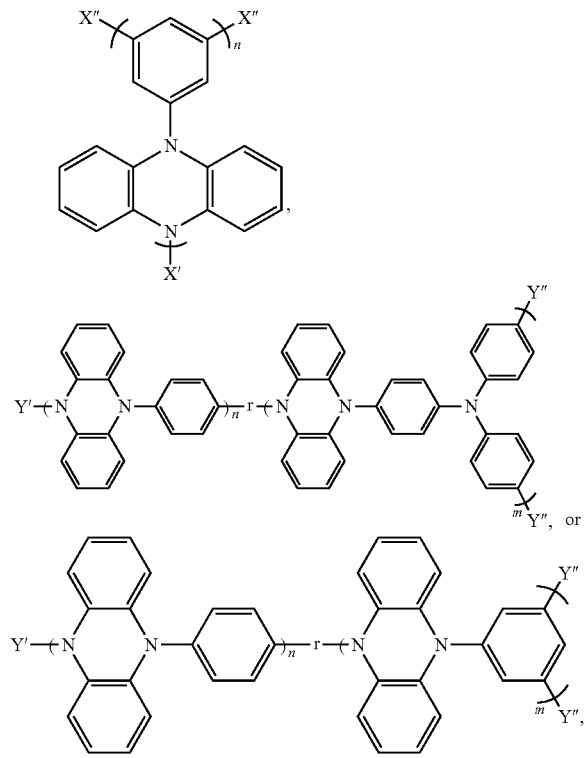

wherein X' is a cross-linking unit or —H; X" is a phenazine unit, —F, —Cl, —Br, —I, —CH=O, or —OR, wherein —OR is —OTs (tosylate), —OMs (mesylate), —OTf (triflate)); Y' is a co-monomer unit, a cross-linking unit, or —H; and Y" is a phenazine unit, —F, —Cl, —Br, —I, —CH=O, or —OR, wherein —OR is —OTs (tosylate), —OMs (mesylate), —OTf (triflate)), wherein r indicates random, wherein n is from 1 to 1000, and wherein m is from 1 to 1000.

4. The phenazine polymer of claim 1, wherein the phenazine copolymer has an amorphous, globular morphology.

5. The phenazine polymer of claim 1, wherein the phenazine copolymer has 10% or less (by weight) crystalline domains based on the total weight of the phenazine copolymer.

6. The phenazine polymer of claim 1, comprising 0-40 mol % of one or more cross-linking unit(s), wherein mol % is relative to the total moles of the phenazine copolymer.

7. The phenazine polymer of claim 6, wherein the one or more cross-linking unit(s) has/have the following structure:

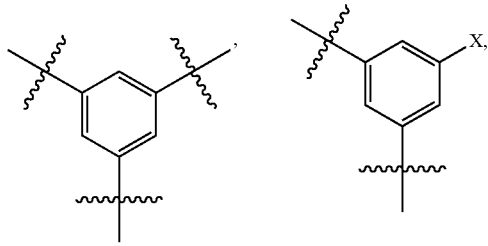

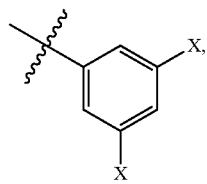

or a combination thereof,
wherein X is independently at each occurrence chosen from a phenazine unit, a co-monomer unit —H, —F, —Cl, —Br, —I, —CH=O, and —OR, wherein —OR is —OTs (tosylate), —OMs (mesylate), —OTf (triflate).

8. A cathode comprising a layer of phenazine polymer of claim 1, wherein the layer has a thickness of 1-500 microns.

9. The cathode of claim 8, further comprising one or more carbon material(s) and/or one or more binder material(s).

10. The cathode of claim 9, wherein the one or more carbon material(s) is chosen from carbon black, carbon paper, and combinations thereof.

11. The cathode of claim 9, wherein the one or more binder material(s) is polyvinylidene-fluoride.

12. The cathode of claim 8, further comprising a current collector and the phenazine polymer is present as film or a component of a film disposed on the current collector.

13. The phenazine polymer of claim 1, where at least a portion of or all of the co-monomer units have the following structure:

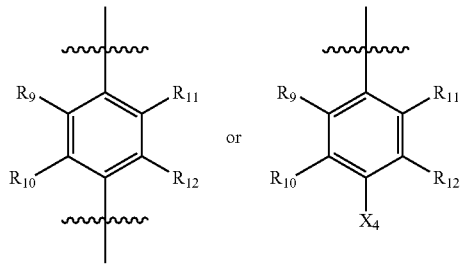

where $R_9$, $R_{10}$, $R_{11}$, $R_{12}$ are independently at each occurrence chosen from —H, —OCH$_3$, —CN, —CH$_3$, and —(CH$_2$)$_n$CH$_3$, wherein n is 1 to 12, —SCH$_3$, and $X_4$ is chosen from a phenazine unit, a cross-linking unit, —H, —F, —Cl, —Br, —I, —CH=O, and —OR, where —OR is —OTs (tosylate), —OMs (mesylate), —OTf (triflate); or

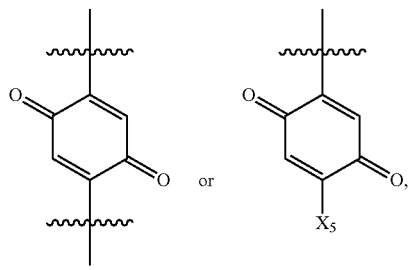

where $X_5$ is chosen from a phenazine unit, a cross-linking unit, —H, —F, —Cl, —Br, —I, —CH=O, and —OR, and the like, where —OR is —OTs (tosylate), —OMs (mesylate), —OTf (triflate); or

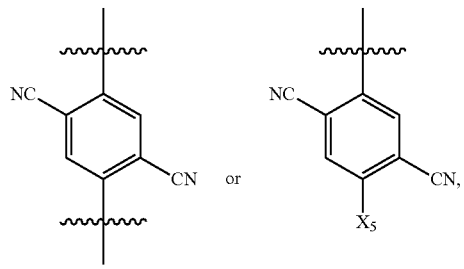

where $X_5$ is chosen from a phenazine unit, a cross-linking unit, —H, —F, —Cl, —Br, —I, —CH=O, and —OR, and the like, where —OR is —OTs (tosylate), —OMs (mesylate), —OTf (triflate); or

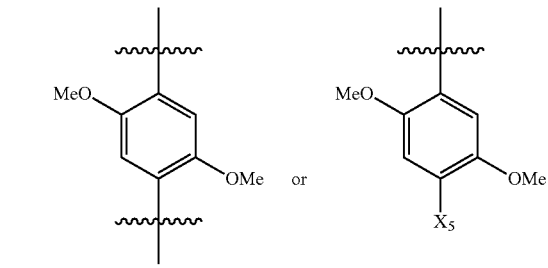

where $X_5$ is chosen from a phenazine unit, a cross-linking unit, —H, —F, —Cl, —Br, —I, —CH=O, and —OR, and the like, where —OR is —OTs (tosylate), —OMs (mesylate), —OTf (triflate);

or a combination thereof.

* * * * *